(12) United States Patent
Leahy

(10) Patent No.: US 9,670,212 B2
(45) Date of Patent: Jun. 6, 2017

(54) INHIBITORS OF PI3K-DELTA AND METHODS OF THEIR USE AND MANUFACTURE

(75) Inventor: James William Leahy, San Leandro, CA (US)

(73) Assignee: Exelixis, Inc., South San Francisco, CA (US)

(*) Notice: Subject to any disclaimer, the term of this patent is extended or adjusted under 35 U.S.C. 154(b) by 742 days.

(21) Appl. No.: 13/822,809

(22) PCT Filed: Sep. 14, 2011

(86) PCT No.: PCT/US2011/051531
§ 371 (c)(1),
(2), (4) Date: Oct. 25, 2013

(87) PCT Pub. No.: WO2012/037204
PCT Pub. Date: Mar. 22, 2012

(65) Prior Publication Data
US 2014/0045825 A1 Feb. 13, 2014
US 2014/0303151 A9 Oct. 9, 2014

Related U.S. Application Data

(60) Provisional application No. 61/382,873, filed on Sep. 14, 2010.

(51) Int. Cl.

| C07D 473/38 | (2006.01) |
|---|---|
| C07D 215/12 | (2006.01) |
| C07D 215/14 | (2006.01) |
| C07D 215/38 | (2006.01) |
| C07D 401/12 | (2006.01) |
| C07D 401/14 | (2006.01) |
| C07D 403/12 | (2006.01) |
| C07D 405/12 | (2006.01) |
| C07D 413/14 | (2006.01) |
| C07D 473/34 | (2006.01) |
| C07D 487/04 | (2006.01) |
| C07D 495/04 | (2006.01) |
| C07D 519/00 | (2006.01) |
| C07D 213/30 | (2006.01) |
| C07D 213/38 | (2006.01) |
| C07D 295/125 | (2006.01) |

(52) U.S. Cl.
CPC ........ *C07D 473/38* (2013.01); *C07D 213/30* (2013.01); *C07D 213/38* (2013.01); *C07D 215/12* (2013.01); *C07D 215/14* (2013.01); *C07D 215/38* (2013.01); *C07D 295/125* (2013.01); *C07D 401/12* (2013.01); *C07D 401/14* (2013.01); *C07D 403/12* (2013.01); *C07D 405/12* (2013.01); *C07D 413/14* (2013.01); *C07D 473/34* (2013.01); *C07D 487/04* (2013.01); *C07D 495/04* (2013.01); *C07D 519/00* (2013.01)

(58) Field of Classification Search
CPC .................................................. C07D 400/01
See application file for complete search history.

(56) References Cited

FOREIGN PATENT DOCUMENTS

| WO | 2007088999 | 8/2007 |
|---|---|---|
| WO | 2008/064018 | 5/2008 |
| WO | 2008118454 | 10/2008 |
| WO | 2008118455 | 10/2008 |
| WO | 2008118468 | 10/2008 |
| WO | WO 2008/118454 | * 10/2008 |
| WO | 2009081105 | 7/2009 |
| WO | WO 2009/081105 | * 7/2009 |
| WO | 2010036380 | 4/2010 |
| WO | 2010065923 | 6/2010 |
| WO | 2010092340 | 8/2010 |
| WO | 2011058112 | 5/2011 |

OTHER PUBLICATIONS

Pinedo et al. (2000).*
McMahon et al. (2000).*
F. Nawaz Khan, et al.: "2-Chloro-8-methyl-3-[(pyrimidin-4-yloxy)methyl]quinoline", ACTA Crystallographica Section E Structure Reports Online, vol. 66, No. 5, Apr. 2, 2010 (Apr. 2, 2010).
International Search Report for PCT/US2011/051531, mailed Dec. 23, 2011.

* cited by examiner

*Primary Examiner* — Paul V Ward
(74) *Attorney, Agent, or Firm* — Honigman Miller Schwartz & Cohn LLP; Heidi M. Berven; Jonathan P. O'Brien

(57) ABSTRACT

The invention is directed to Compounds of Formula I: and pharmaceutically acceptable salts or solvates thereof, as well as methods of making and using the compounds.

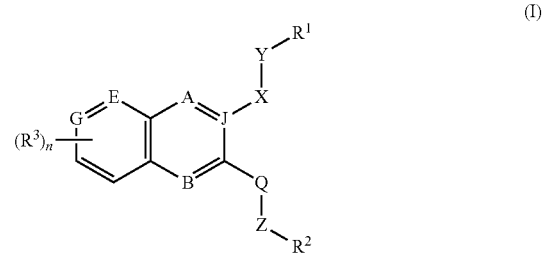

14 Claims, No Drawings

INHIBITORS OF PI3K-DELTA AND METHODS OF THEIR USE AND MANUFACTURE

CROSS-REFERENCE TO RELATED APPLICATIONS

This application is a United States National Phase filing of PCT/US2011/051531, filed Sep. 14, 2011, which claims priority to U.S. Provisional Application No. 61/382,873, filed Sep. 14, 2010, the entire contents of which are incorporated herein by reference.

FIELD OF THE INVENTION

This invention relates to the field of protein kinases and inhibitors thereof. In particular, the invention relates to inhibitors of PI3K delta, and methods of their use.

BACKGROUND OF THE INVENTION

Phosphoinositide 3-kinases (PI3Ks) are heterodimeric enzymes that utilize both lipid and protein kinase activity to regulate numerous lipid signaling pathways that are responsible for coordinating a broad range of cellular activities including cell survival, proliferation, and differentiation as well as inflammatory responses. The critical role of PI3Ks in these myriad important cellular processes make them a very attractive target for pharmaceutical intervention. The class of PI3Ks relevant to this disclosure catalyze the phosphorylation of phosphatilyl-inositol (4,5)-bisphosphate (PtIns(4, 5)P$_2$ or PIP$_2$) on the 3-hydroxyl group of the inositol ring to produce the signaling molecule phosphatilyl-inositol (3,4, 5)-triphosphate (PtIns(3,4,5)P$_3$ or PIP$_3$).

After extensive studies on the physiological role of the PI3K delta isoform in disease, PI3K delta is implicated in a large number of immunological, inflammatory and cell regulation dysfunctions. Initial studies have focused its role in immune and inflammatory pathologies. PI3K delta plays a significant role in the development, differentiation, proliferation and effector function of B-cells and T-cells. PI3K delta knock-in mice (D910A/D910A) have shown impaired or diminished proliferative T-cell responses and chemokine production when stimulated with T-cell receptor specific antigens. Moreover, these PI3K delta expressing animals demonstrate poor T-cell independent antibody responses concomitant with poor development of germinal centers in the spleen, lymph nodes and Peyer's patches and lymphoid hyperplasia after immunization. Inhibition of PI3K delta function also leads to dysfunctional homing by T-cells to sites of inflammation. PI3K delta activity has also been implicated in Treg cell control. PI3K delta$^{(D910A/D910A)}$ mice have Treg cells that fail to: 1.) suppress the proliferation of CD4$^+$ CD25$^-$ T-cells in vitro as well as Treg cells from wild-type animals; 2.) produce detectable levels of the anti-inflammatory cytokine IL-10; and 3.) protect against experimental colitis.

The effects of PI3K delta on B-cells are no less significant. Mice lacking p110 delta catalytic activity have reduced numbers of B1 and marginal zone (MZ) B cells, reduced levels of serum immunoglulins, and respond poorly to immunization with a thymus-independent antigen and are defective in their primary and secondary responses to thymus dependent antigens. Inhibition of PI3K delta via use of PI3K delta selective inhibitors have shown inhibition of B-cell receptor-induced B cell proliferation, and increased class-switch recombination. and defects in B-cell chemotaxis.

Experimental observations that PI3K delta may play a significant role in mediating the proinflammatory role of non-lymphoid hematopoetic cells have come from studies involving hematopoietic immune cells such as neutrophils, macrophages, dendritic cells, mast cells and eosinophils. For example, PI3K delta is required for neutrophil spreading and polarization, regulation of neutrophil migration, mast cell degranulation and among many others. A review of the important roles of PI3K delta in innate and adaptive immune responses, has generated intense investigation of the role of PI3K delta in immune diseases such as allergy, asthma, autoimmune diseases, and inflammation.

While a significant portion of the published scientific literature has focused on immune diseases, such as inflammation, autoimmune disease and the like, an attractive and productive area for investigation includes the role of PI3K delta in cancer. Experimental models have already provided for putative roles of PI3K alpha and PI3K beta in malignant cellular processes, including: (i) overexpression is capable of inducing transformation in experimental models; (ii) involvement in cell proliferation and tumor angiogenesis; (iii) involvement in Ras-induces transformation and oncogenesis (iv) activating mutations in the helical and kinase domains in breast and colon tumors; and (v) transformation induced by PTEN inactivation in vitro and in vivo As with PI3K alpha and PI3K beta, PI3K delta also induces oncogenic transformation in culture. When PI3K delta is introduced into chicken embryo fibroblasts (CEFs) with an avian retroviral vector, distinct foci form within ten days. When D910A kinase inactive PI3K delta is introduced into CEFs, no focus formation is observed indicating that transformation requires an active catalytic domain. As was observed for an oncogenic variant of PI3K alpha (H1047R), CEFs infected with PI3K delta showed constitutive activation of Akt at a level similar to PI3K alpha, even in serum starved conditions. For at least the reasons provided above, there is a need for selective PI3K delta inhibitors that can be used to prevent, treat or ameliorate PI3K delta mediated diseases, particularly in the fields of cancer, inflammation and autoimmune diseases.

SUMMARY OF THE INVENTION

The following only summarizes certain aspects of the invention and is not intended to be limiting in nature. These aspects and other aspects and embodiments are described more fully below. All references cited in this specification are hereby incorporated by reference in their entirety. In the event of a discrepancy between the express disclosure of this specification and the references incorporated by reference, the express disclosure of this specification shall control.

We recognized the important role of PI3K, particularly PI3K delta, in biological processes and disease states and, therefore, realized that inhibitors of these protein kinases would be desirable. Accordingly, the invention provides compounds that inhibit, regulate, and/or modulate PI3K delta that are useful in the treatment of various cancers, autoimmune diseases, inflammatory diseases in mammals. This invention also provides methods of making the compounds, methods of using such compounds in the treatment diseases, particularly hyperproliferative diseases, in mammals, especially humans, and to pharmaceutical compositions containing such compounds.

A first aspect of the invention provides a compound of Formula I:

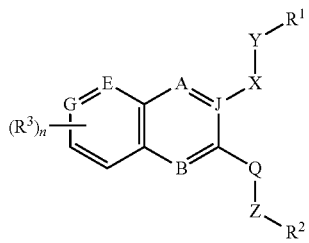

or a stereoisomer or mixture of stereoisomers thereof, optionally as a pharmaceutically acceptable salt thereof, wherein:

A is N, C—H, or C—OH;
B is C—H or N;
E is absent or is C—$R^4$;
G is S C—H, or C—$R^3$;
J is C or N when A is C—H or C—OH, or J is C when A is N;
X is absent or is NH or is optionally substituted N—($C_1$-$C_6$)alkyl;
Y is absent or is optionally substituted ($C_1$-$C_6$)alkylene wherein up to two carbon atoms of the ($C_1$-$C_6$)alkylene are replaced by O, NH, N—($C_1$-$C_6$)alkyl, —NH—(C=O)—, —N($C_1$-$C_6$)alkyl-(C=O)—, or —(C=O)—;
Q is absent or is ($C_1$-$C_6$)alkylene;
Z is absent or is NH, N($C_1$-$C_6$)alkyl, NH($C_1$-$C_6$)alkylene, —NH—(C=O)—, —N($C_1$-$C_6$)alkyl-(C=O)—, S, SO, $SO_2$, or O;
$R^1$ is halo, hydroxy, cyano, optionally substituted aryl, optionally substituted heteroaryl, optionally substituted heterocycloalkyl, optionally substituted ($C_1$-$C_6$)alkyl, optionally substituted ($C_1$-$C_6$)alkoxy, ($C_1$-$C_6$)alkyl-OH, $NH_2$, —NH—($C_1$-$C_6$)alkyl, —NH—(($C_1$-$C_6$)alkyl)$_2$, —NH—(C=O)—$R^5$, —(C=O)NR$^6$R$^7$, or —NH—($SO_2$)—$R^8$;
$R^2$ is $NH_2$, optionally substituted cycloalkyl, optionally substituted heterocycloalkyl, or optionally substituted heteroaryl,
$R^3$ at each occurrence is independently halo, cyano, optionally substituted ($C_1$-$C_6$)alkyl, or ($C_1$-$C_6$)alkoxy;
$R^4$ is H or optionally substituted ($C_1$-$C_6$)alkyl;
$R^5$ is H, optionally substituted ($C_1$-$C_6$)alkyl, optionally substituted cycloalkyl, optionally substituted heterocycloalkyl, optionally substituted aryl, or optionally substituted heteroaryl;
$R^6$ and $R^7$ are each independently H, optionally substituted ($C_1$-$C_6$)alkyl, optionally substituted cycloalkyl, optionally substituted heterocycloalkyl, optionally substituted aryl, optionally substituted heteroaryl, or $R^6$ and $R^7$, together with the atoms to which they are attached, can be taken together to form an optionally substituted 3, 4, 5, 6, or 7-membered ring;
$R^8$ is optionally substituted ($C_1$-$C_6$)alkyl, optionally substituted cycloalkyl, optionally substituted heterocycloalkyl, optionally substituted aryl, or optionally substituted heteroaryl.

In a second aspect, the invention provides a pharmaceutical composition which comprises 1) a compound of Formula I or a single stereoisomer or mixture of isomers thereof, optionally as a pharmaceutically acceptable salt thereof and 2) a pharmaceutically acceptable carrier, excipient, or diluent.

In a third aspect, the invention provides a method of inhibiting the in vivo activity of PI3K delta, the method comprising administering to a patient an effective PI3K delta-inhibiting amount of a Compound of Formula I or a single stereoisomer or mixture of stereoisomers thereof, optionally as a pharmaceutically acceptable salt or solvate thereof or pharmaceutical composition thereof.

In a fourth aspect, the invention provides a method for treating a disease, disorder, or syndrome which method comprises administering to a patient a therapeutically effective amount of a compound of Formula I or a single stereoisomer or mixture of isomers thereof, optionally as a pharmaceutically acceptable salt or solvate thereof, or a pharmaceutical composition comprising a therapeutically effective amount of a compound of Formula I or a single stereoisomer or mixture of isomers thereof, optionally as a pharmaceutically acceptable salt or solvate thereof, and a pharmaceutically acceptable carrier, excipient, or diluent.

In a fifth aspect, the invention provides a process for making a compound of Formula II-B, comprising:

(a) converting a compound of formula II-1 to a compound of formula II-2 via reduction to the alcohol and conversion of the alcohol to the halide, wherein $X^1$ is halo;

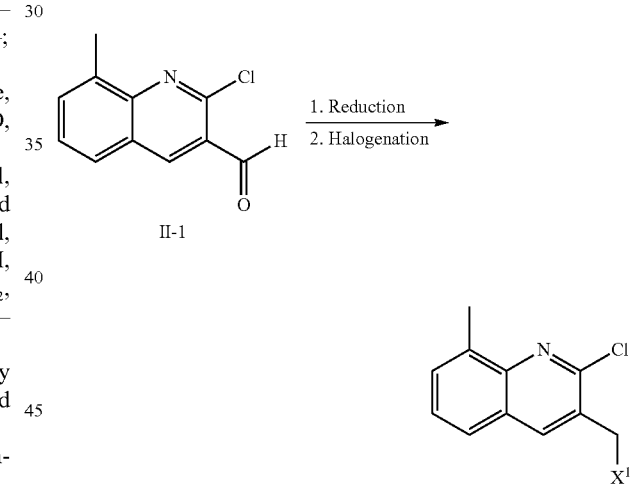

(b) converting a compound of formula II-2 to a compound of formula II-3 via azide formation and subsequent reduction;

(c) converting a compound of formula II-3 to a compound of formula II-4 via reaction with $R^2$—$X^2$, wherein $X^2$ is halo

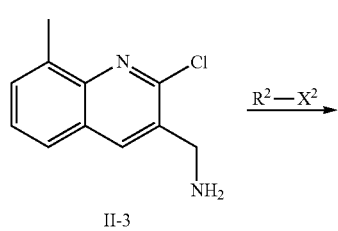

II-3

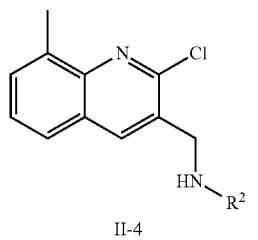

II-4

(d) converting a compound of formula II-4 to a compound of formula II-B via reaction with $CH_3NH—Y—R^1$;

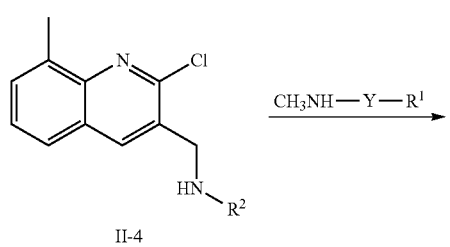

II-B

In a sixth aspect, the invention provides a process for making a compound of Formula II-A, comprising:

(a) converting the carboxylic acid of formula II-5 to an amide of formula II-6;

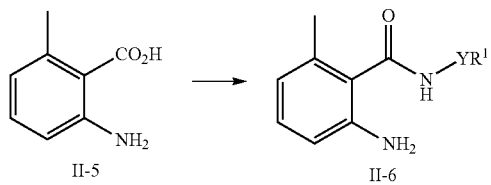

(b) converting a compound of formula II-6 to a compound of formula II-7 via treatment with 2-haloacetyl chloride, wherein $X^1$ is halo;

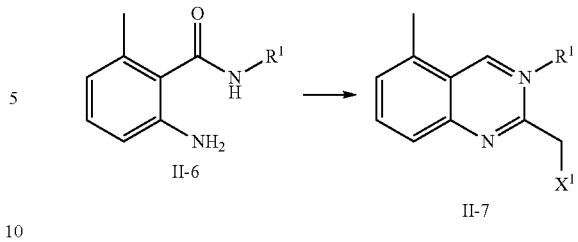

(c) converting a compound of formula II-7 to a compound of formula II-8 via azide formation and subsequent reduction;

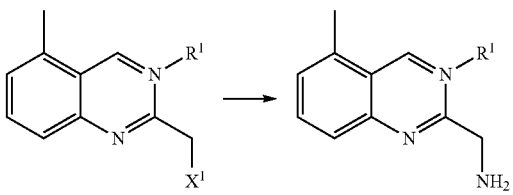

(d) converting a compound of formula II-8 to a compound of formula II-A via reaction with $R2\text{-}CO_2H$;

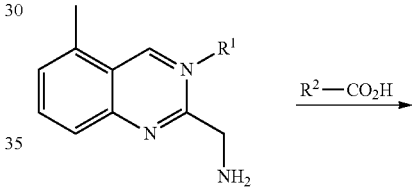

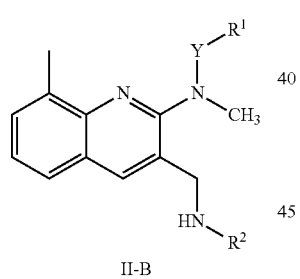

II-A

DETAILED DESCRIPTION OF THE INVENTION

The following abbreviations and terms have the indicated meanings throughout:

| Abbreviation | Meaning |
| --- | --- |
| AcOH | acetic acid |
| br | broad |
| ° C. | degrees Celsius |
| conc | concentrated |
| d | doublet |
| dd | doublet of doublet |
| dt | doublet of triplet |
| DCM | dichloromethane |

| Abbreviation | Meaning |
| --- | --- |
| DIEA or DIPEA | N,N-di-isopropyl-N-ethylamine |
| DMA | N,N-dimethylacetamide |
| DME | 1,2-dimethoxyethane |
| DMF | N,N-dimethylformamide |
| DMSO | dimethyl sulfoxide |
| dppf | 1,1'-bis(diphenylphosphano)ferrocene |
| EI | Electron Impact ionization |
| equiv | equivalents |
| g | gram(s) |
| GC/MS | gas chromatography/mass spectrometry |
| h or hr | hour(s) |
| HATU | 2-(1H-7-azabenzotriazol-1-yl)-1,1,3,3-tetramethyl uronium hexafluorophosphate |
| HPLC | high pressure liquid chromatography |
| L | liter(s) |
| LC/MS | liquid chromatography/mass spectrometry |
| M | molar or molarity |
| m | Multiplet |
| MeOH | methanol |
| mg | milligram(s) |
| MHz | megahertz (frequency) |
| min | minute(s) |
| mL | milliliter(s) |
| μL | microliter(s) |
| μM | micromolar |
| μmol | micromole(s) |
| mM | Millimolar |
| mmol | millimole(s) |
| mol | mole(s) |
| MS | mass spectral analysis |
| Ms | mesyl |
| N | normal or normality |
| nM | Nanomolar |
| NMR | nuclear magnetic resonance spectroscopy |
| q | Quartet |
| quant | quantitative |
| rt | Room temperature |
| s | Singlet |
| t or tr | Triplet |
| THF | tetrahydrofuran |
| Ts | tosyl |

The symbol "—" means a single bond, "═" means a double bond, "≡" means a triple bond, "╌╌╌" means a single or double bond. The symbol "∼" refers to a group on a double-bond as occupying either position on the terminus of a double bond to which the symbol is attached; that is, the geometry, E- or Z—, of the double bond is ambiguous. When a group is depicted removed from its parent Formula, the "~" symbol will be used at the end of the bond which was theoretically cleaved in order to separate the group from its parent structural Formula.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual Formula as having a hydrogen or hydrogens as substitution (expressly defined hydrogen), for example, —CH₂CH₂—. It is understood by one of ordinary skill in the art that the aforementioned descriptive techniques are common in the chemical arts to provide brevity and simplicity to description of otherwise complex structures.

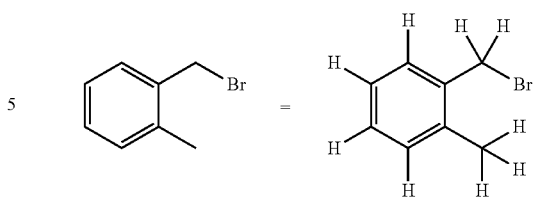

If a group "R" is depicted as "floating" on a ring system, as for example in the Formula:

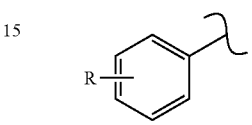

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused or bridged ring system, as for example in the Formula e:

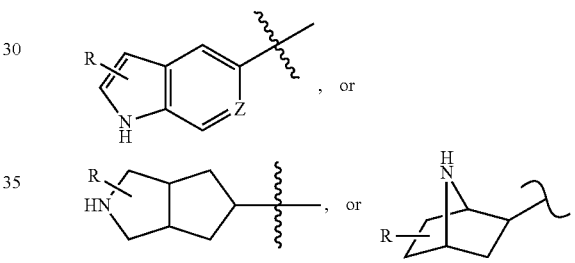

then, unless otherwise defined, a substituent "R" may reside on any atom of the fused or bridged ring system, assuming replacement of a depicted hydrogen (for example the —NH— in the Formula above), implied hydrogen (for example as in the Formula above, where the hydrogens are not shown but understood to be present), or expressly defined hydrogen (for example where in the Formula above, "Z" equals ═CH—) from one of the ring atoms, so long as a stable structure is formed. In the example depicted, the "R" group may reside on either the 5-membered or the 6-membered ring of the fused or bridged ring system.

When a group "R" is depicted as existing on a ring system containing saturated carbons, as for example in the Formula:

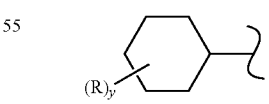

where, in this example, "y" can be more than one, assuming each replaces a currently depicted, implied, or expressly defined hydrogen on the ring; then, unless otherwise defined, where the resulting structure is stable, two "R's" may reside on the same carbon. In another example, two R's on the same carbon, including that carbon, may form a ring, thus creating a spirocyclic ring structure with the depicted ring as for example in the Formula:

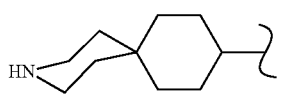

"Acyl" means a —C(O)R radical where R is alkyl, haloalkyl, alkenyl, cycloalkyl, cycloalkylalkyl, aryl, aralkyl, heteroaryl, heteroaralkyl, heterocycloalkyl, or heterocycloalkylalkyl, as defined herein, e.g., acetyl, trifluoromethylcarbonyl, or 2-methoxyethylcarbonyl, and the like.

"Acylamino" means a —NRR' radical where R is hydrogen, hydroxy, alkyl, or alkoxy and R' is acyl, as defined herein.

"Acyloxy" means an —OR radical where R is acyl, as defined herein, e.g. cyanomethylcarbonyloxy, and the like.

"Administration" and variants thereof (e.g., "administering" a compound) in reference to a compound of the invention means introducing the compound of the compound into the system of the animal in need of treatment. When a compound of the invention or prodrug thereof is provided in combination with one or more other active agents (e.g., surgery, radiation, and chemotherapy, etc.), "administration" and its variants are each understood to include concurrent and sequential introduction of the compound or prodrug thereof and other agents.

"Alkenyl" means a means a linear monovalent hydrocarbon radical of two to six carbon atoms or a branched monovalent hydrocarbon radical of three to 6 carbon atoms which radical contains at least one double bond, e.g., ethenyl, propenyl, 1-but-3-enyl, and 1-pent-3-enyl, and the like.

"Alkoxy" means an —OR group where R is alkyl group as defined herein. Examples include methoxy, ethoxy, propoxy, isopropoxy, and the like.

"Alkoxyalkyl" means an alkyl group, as defined herein, substituted with at least one, specifically one, two, or three, alkoxy groups as defined herein. Representative examples include methoxymethyl and the like.

"Alkoxycarbonyl" means a —C(O)R group where R is alkoxy, as defined herein.

"Alkyl" means a linear saturated monovalent hydrocarbon radical of one to six carbon atoms or a branched saturated monovalent hydrocarbon radical of three to 6 carbon atoms, e.g., methyl, ethyl, propyl, 2-propyl, butyl (including all isomeric forms), or pentyl (including all isomeric forms), and the like.

"Alkylamino" means an —NHR group where R is alkyl, as defined herein.

"Alkylaminoalkyl" means an alkyl group substituted with one or two alkylamino groups, as defined herein.

"Alkylaminoalkyloxy" means an —OR group where R is alkylaminoalkyl, as defined herein.

"Alkylcarbonyl" means a —C(O)R group where R is alkyl, as defined herein.

"Alkylene" means an optionally substituted straight or branched chain divalent hydrocarbon radical, preferably having from one to ten carbon atoms, unless specified otherwise. Examples of "alkylene" as used herein include, but are not limited to, methylene, ethylene, n-propylene, n-butylene, and the like.

"Alkylsulfonyl" means an —S(O)$_2$R group where R is alkyl, as defined herein.

"Alkylsulfonylalkyl" means an alkyl group, as defined herein, substituted with at least one, preferably one or two, alkylsulfonyl groups, as defined herein.

"Alkynyl" means a linear monovalent hydrocarbon radical of two to six carbon atoms or a branched monovalent hydrocarbon radical of three to 6 carbon atoms which radical contains at least one triple bond, e.g., ethynyl, propynyl, butynyl, pentyn-2-yl and the like.

"Amino" means —NH$_2$.

"Aminoalkyl" means an alkyl group substituted with at least one, specifically one, two or three, amino groups.

"Aminoalkyloxy" means an —OR group where R is aminoalkyl, as defined herein.

"Aminocarbonyl" means a —C(O)NH$_2$ group.

"Alkylaminocarbonyl" means a —C(O)NHR group where R is alkyl as defined herein.

"Aryl" means a monovalent six- to fourteen-membered, mono- or bi-carbocyclic ring, wherein the monocyclic ring is aromatic and at least one of the rings in the bicyclic ring is aromatic. Unless stated otherwise, the valency of the group may be located on any atom of any ring within the radical, valency rules permitting. Representative examples include phenyl, naphthyl, and indanyl, and the like.

"Arylalkyl" means an alkyl radical, as defined herein, substituted with one or two aryl groups, as defined herein, e.g., benzyl and phenethyl, and the like.

"Arylalkyloxy" means an —OR group where R is arylalkyl, as defined herein.

"Cyanoalkyl" means an alkyl group, as defined herein, substituted with one or two cyano groups.

"Cycloalkyl" means a monocyclic or fused or bridged bicyclic or tricyclic, saturated or partially unsaturated (but not aromatic), monovalent hydrocarbon radical of three to ten carbon ring atoms. Unless stated otherwise, the valency of the group may be located on any atom of any ring within the radical, valency rules permitting. One or two ring carbon atoms may be replaced by a —C(O)—, —C(S)—, or —C(=NH)— group. More specifically, the term cycloalkyl includes, but is not limited to, cyclopropyl, cyclobutyl, cyclopentyl, cyclohexyl, cyclohexyl, cyclohex-3-enyl, or (1r,3r,5R,7R)-tricyclo[3.3.1.1$^{3,7}$]decan-2-yl, and the like.

"Cycloalkylalkyl" means an alkyl group substituted with at least one, specifically one or two, cycloalkyl group(s) as defined herein.

"Dialkylamino" means a —NRR' radical where R and R' are alkyl as defined herein, or an N-oxide derivative, or a protected derivative thereof, e.g., dimethylamino, diethylamino, N,N-methylpropylamino or N,N-methylethylamino, and the like.

"Dialkylaminoalkyl" means an alkyl group substituted with one or two dialkylamino groups, as defined herein.

"Dialkylaminoalkyloxy" means an —OR group where R is dialkylaminoalkyl, as defined herein. Representative examples include 2-(N,N-diethylamino)-ethyloxy, and the like.

"Dialkylaminocarbonyl" means a —C(O)NRR' group where R and R' are alkyl as defined herein.

"Halogen" or "halo" refers to fluorine, chlorine, bromine and iodine.

"Haloalkoxy" means an —OR' group where R' is haloalkyl as defined herein, e.g., trifluoromethoxy or 2,2,2-trifluoroethoxy, and the like.

"Haloalkyl" mean an alkyl group substituted with one or more halogens, specifically 1, 2, 3, 4, 5, or 6 halo atoms, e.g., trifluoromethyl, 2-chloroethyl, and 2,2-difluoroethyl, and the like.

"Heteroaryl" means a monocyclic or fused or bridged bicyclic monovalent radical of 5 to 14 ring atoms containing one or more, specifically one, two, three, or four ring heteroatoms where each heteroatom is independently —O—, —S(O)$_n$— (n is 0, 1, or 2), —NH—, —N=, or N-oxide, with the remaining ring atoms being carbon, wherein the ring comprising a monocyclic radical is aromatic and wherein at least one of the fused rings comprising the bicyclic radical is aromatic. One or two ring carbon atoms of any nonaromatic rings comprising a bicyclic radical may be replaced by a —C(O)—, —C(S)—, or —C(=NH)— group. Unless stated otherwise, the valency may be located on any atom of any ring of the heteroaryl group, valency rules permitting. More specifically, the term heteroaryl includes, but is not limited to, 1,2,4-triazolyl, 1,3,5-triazolyl, phthalimidyl, pyridinyl, pyrrolyl, imidazolyl, thienyl, furanyl, indolyl, 2,3-dihydro-1H-indolyl (including, for example, 2,3-dihydro-1H-indol-2-yl or 2,3-dihydro-1H-indol-5-yl, and the like), isoindolyl, indolinyl, isoindolinyl, benzimidazolyl, benzodioxol-4-yl, benzofuranyl, cinnolinyl, indolizinyl, naphthyridin-3-yl, phthalazin-3-yl, phthalazin-4-yl, pteridinyl, purinyl, quinazolinyl, quinoxalinyl, tetrazoyl, pyrazolyl, pyrazinyl, pyrimidinyl, pyridazinyl, oxazolyl, isooxazolyl, oxadiazolyl, benzoxazolyl, quinolinyl, isoquinolinyl, tetrahydroisoquinolinyl (including, for example, tetrahydroisoquinolin-4-yl or tetrahydroisoquinolin-6-yl, and the like), pyrrolo[3,2-c]pyridinyl (including, for example, pyrrolo[3,2-c]pyridin-2-yl or pyrrolo[3,2-c]pyridin-7-yl, and the like), benzopyranyl, 2,3-dihydrobenzofuranyl, benzo[d][1,3]dioxolyl, 2,3-dihydrobenzo[b][1,4] dioxinyl, thiazolyl, isothiazolyl, thiadiazolyl, benzothiazolyl, benzothienyl, and the derivatives thereof, or N-oxide or a protected derivative thereof. The term "5- or 6-membered heteroaryl" describes a subset of the term "heteroaryl."

"Heteroarylalkyl" means an alkyl group, as defined herein, substituted with at least one, specifically one or two heteroaryl group(s), as defined herein.

"Heterocycloalkyl" means a saturated or partially unsaturated (but not aromatic) monovalent monocyclic group of 3 to 8 ring atoms or a saturated or partially unsaturated (but not aromatic) monovalent fused or bridged, bicyclic or tricyclic group of 5 to 12 ring atoms in which one or more, specifically one, two, three, or four ring heteroatoms where each heteroatom is independently O, S(O)$_n$ (n is 0, 1, or 2), —N=, or —NH—, the remaining ring atoms being carbon. One or two ring carbon atoms may be replaced by a —C(O)—, —C(S)—, or —C(=NH)— group. Unless otherwise stated, the valency of the group may be located on any atom of any ring within the radical, valency rules permitting. When the point of valency is located on a nitrogen atom, R$^y$ is absent. More specifically the term heterocycloalkyl includes, but is not limited to, azetidinyl, pyrrolidinyl, 2-oxopyrrolidinyl, 2,5-dihydro-1H-pyrrolyl, piperidinyl, 4-piperidonyl, morpholinyl, piperazinyl, 2-oxopiperazinyl, tetrahydropyranyl, 2-oxopiperidinyl, thiomorpholinyl, thiamorpholinyl, perhydroazepinyl, pyrazolidinyl, imidazolinyl, imidazolidinyl, dihydropyridinyl, tetrahydropyridinyl, oxazolinyl, oxazolidinyl, isoxazolidinyl, thiazolinyl, thiazolidinyl, quinuclidinyl, isothiazolidinyl, octahydrocyclopenta[c]pyrrolyl, octahydroindolyl, octahydroisoindolyl, decahydroisoquinolyl, tetrahydrofuryl, tetrahydropyranyl, (3aR,6aS)-5-methyloctahydrocyclopenta[c]pyrrolyl, and (3aS,6aR)-5-methyl-1,2,3,3a,4,6a-hexahydrocyclopenta[c]pyrrolyl, and the derivatives thereof and N-oxide or a protected derivative thereof.

"Heterocycloalkylalkyl" means an alkyl radical, as defined herein, substituted with one or two heterocycloalkyl groups, as defined herein, e.g., morpholinylmethyl, N-pyrrolidinylethyl, and 3-(N-azetidinyl)propyl, and the like.

"Heterocycloalkyloxy" means an —OR group where R is heterocycloalkyl, as defined herein.

"Hydroxyalkyl" means an alkyl group, as defined herein, substituted with at least one, preferably 1, 2, 3, or 4, hydroxy groups.

"Phenylalkyl" means an alkyl group, as defined herein, substituted with one or two phenyl groups.

"Phenylalkyloxy" means an —OR group where R is phenylalkyl, as defined herein.

"Optional" or "optionally" means that the subsequently described event or circumstance may or may not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term, unless stated otherwise. A list of exemplary optional substitutions is presented below in the definition of "substituted."

"Optionally substituted aryl" means an aryl group, as defined herein, optionally substituted with one, two, or three substituents independently acyl, acylamino, acyloxy, alkyl, haloalkyl, alkenyl, alkoxy, alkenyloxy, halo, hydroxy, alkoxycarbonyl, alkenyloxycarbonyl, amino, alkylamino, dialkylamino, nitro, aminocarbonyl, alkylaminocarbonyl, dialkylaminocarbonyl, carboxy, cyano, alkylthio, alkylsulfinyl, alkylsulfonyl, aminosulfonyl, alkylaminosulfonyl, dialkylaminosulfonyl, alkylsulfonylamino, or aminoalkoxy; or aryl is pentafluorophenyl. Within the optional substituents on "aryl", the alkyl and alkenyl, either alone or as part of another group (including, for example, the alkyl in alkoxycarbonyl), are independently optionally substituted with one, two, three, four, or five halo.

"Optionally substituted arylalkyl" means an alkyl group, as defined herein, substituted with optionally substituted aryl, as defined herein.

"Optionally substituted cycloalkyl" means a cycloalkyl group, as defined herein, substituted with one, two, or three groups independently acyl, acyloxy, acylamino, alkyl, haloalkyl, alkenyl, alkoxy, alkenyloxy, alkoxycarbonyl, alkenyloxycarbonyl, alkylthio, alkylsulfinyl, alkylsulfonyl, aminosulfonyl, alkylaminosulfonyl, dialkylaminosulfonyl, alkylsulfonylamino, halo, hydroxy, amino, alkylamino, dialkylamino, aminocarbonyl, alkylaminocarbonyl, dialkylaminocarbonyl, nitro, alkoxyalkyloxy, aminoalkoxy, alkylaminoalkoxy, dialkylaminoalkoxy, carboxy, or cyano. Within the above optional substitutents on "cycloalkyl", the alkyl and alkenyl, either alone or as part of another substituent on the cycloalkyl ring, are independently optionally substituted with one, two, three, four, or five halo, e.g. haloalkyl, haloalkoxy, haloalkenyloxy, or haloalkylsulfonyl.

"Optionally substituted cycloalkylalkyl" means an alkyl group substituted with at least one, specifically one or two, optionally substituted cycloalkyl groups, as defined herein.

"Optionally substituted heteroaryl" means a heteroaryl group optionally substituted with one, two, or three substituents independently acyl, acylamino, acyloxy, alkyl, haloalkyl, alkenyl, alkoxy, alkenyloxy, halo, hydroxy, alkoxycarbonyl, alkenyloxycarbonyl, amino, alkylamino, dialkylamino, nitro, aminocarbonyl, alkylaminocarbonyl, dialkylaminocarbonyl, carboxy, cyano, alkylthio, alkylsulfinyl, alkylsulfonyl, aminosulfonyl, alkylaminosulfonyl, dialkylaminosulfonyl, alkylsulfonylamino, aminoalkoxy, alkylaminoalkoxy, or dialkylaminoalkoxy. Within the optional substituents on "heteroaryl", the alkyl and alkenyl, either alone or as part of another group (including, for example, the alkyl in alkoxycarbonyl), are independently optionally substituted with one, two, three, four, or five halo.

"Optionally substituted heteroarylalkyl" means an alkyl group, as defined herein, substituted with at least one, specifically one or two, optionally substituted heteroaryl group(s), as defined herein.

"Optionally substituted heterocycloalkyl" means a heterocycloalkyl group, as defined herein, optionally substituted with one, two, or three substituents independently acyl, acylamino, acyloxy, haloalkyl, alkyl, alkenyl, alkoxy, alkenyloxy, halo, hydroxy, alkoxycarbonyl, alkenyloxycarbonyl, amino, alkylamino, dialkylamino, nitro, aminocarbonyl, alkylaminocarbonyl, dialkylaminocarbonyl, carboxy, cyano, alkylthio, alkylsulfinyl, alkylsulfonyl, aminosulfonyl, alkylaminosulfonyl, dialkylaminosulfonyl, alkylsulfonylamino, aminoalkoxy, or phenylalkyl. Within the optional substituents on "heterocycloalkyl", the alkyl and alkenyl, either alone or as part of another group (including, for example, the alkyl in alkoxycarbonyl), are independently optionally substituted with one, two, three, four, or five halo.

"Optionally substituted heterocycloalkylalkyl" means an alkyl group, as defined herein, substituted with at least one, specifically one or two, optionally substituted heterocycloalkyl group(s) as defined herein.

"Optionally substituted phenyl" means a phenyl group optionally substituted with one, two, or three substituents independently acyl, acylamino, acyloxy, alkyl, haloalkyl, alkenyl, alkoxy, alkenyloxy, halo, hydroxy, alkoxycarbonyl, alkenyloxycarbonyl, amino, alkylamino, dialkylamino, nitro, aminocarbonyl, alkylaminocarbonyl, dialkylaminocarbonyl, carboxy, cyano, alkylthio, alkylsulfinyl, alkylsulfonyl, aminosulfonyl, alkylaminosulfonyl, dialkylaminosulfonyl, alkylsulfonylamino, or aminoalkoxy, or aryl is pentafluorophenyl. Within the optional substituents on "phenyl", the alkyl and alkenyl, either alone or as part of another group (including, for example, the alkyl in alkoxycarbonyl), are independently optionally substituted with one, two, three, four, or five halo.

"Optionally substituted phenylalkyl" means an alkyl group, as defined herein, substituted with one or two optionally substituted phenyl groups, as defined herein.

"Optionally substituted phenylsulfonyl" means an —S(O)$_2$R group where R is optionally substituted phenyl, as defined herein.

"Oxo" means an oxygen which is attached via a double bond.

"Yield" for each of the reactions described herein is expressed as a percentage of the theoretical yield.

"Patient" for the purposes of the present invention includes humans and other animals, particularly mammals, and other organisms. Thus the methods are applicable to both human therapy and veterinary applications. In a specific embodiment the patient is a mammal, and in a more specific embodiment the patient is human.

A "pharmaceutically acceptable salt" of a compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in Remington's Pharmaceutical Sciences, 17$^{th}$ ed., Mack Publishing Company, Easton, Pa., 1985, which is incorporated herein by reference or S. M. Berge, et al., "Pharmaceutical Salts," J. Pharm. Sci., 1977; 66:1-19 both of which are incorporated herein by reference.

Examples of pharmaceutically acceptable acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, and salicylic acid and the like.

Examples of a pharmaceutically acceptable base addition salts include those formed when an acidic proton present in the parent compound is replaced by a metal ion, such as sodium, potassium, lithium, ammonium, calcium, magnesium, iron, zinc, copper, manganese, aluminum salts and the like. Specific salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins. Examples of organic bases include isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, N-methylglucamine, polyamine resins, and the like. Exemplary organic bases are isopropylamine, diethylamine, ethanolamine, trimethylamine, dicyclohexylamine, choline, and caffeine. "Platin(s)," and "platin-containing agent(s)" include, for example, cisplatin, carboplatin, and oxaliplatin.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to their knowledge and to this disclosure.

"Preventing" or "prevention" of a disease, disorder, or syndrome includes inhibiting the disease from occurring in a human, i.e. causing the clinical symptoms of the disease, disorder, or syndrome not to develop in an animal that may be exposed to or predisposed to the disease, disorder, or syndrome but does not yet experience or display symptoms of the disease, disorder, or syndrome.

"Treating" or "treatment" of a disease, disorder, or syndrome, as used herein, includes (i) inhibiting the disease, disorder, or syndrome, i.e., arresting its development; and (ii) relieving the disease, disorder, or syndrome, i.e., causing regression of the disease, disorder, or syndrome. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

Embodiments of the Invention

The following paragraphs present a number of embodiments of compounds of the invention. In each instance the embodiment includes both the recited compounds, as well as a single stereoisomer or mixture of stereoisomers thereof, as well as a pharmaceutically acceptable salt thereof.

Thus, as provided above, in one aspect, the invention provides a compound of Formula I.

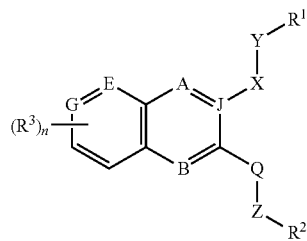

In one embodiment, the compound of Formula I is a compound of Formula I-a or I-b.

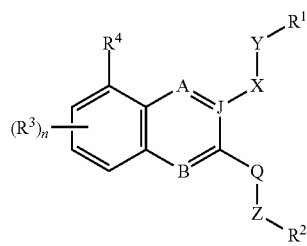
I-a

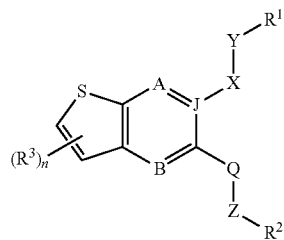
I-b

In another embodiment, the compound of Formula I is a compound of Formula I-c.

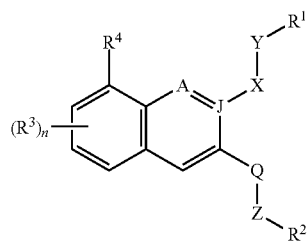
I-c

In another embodiment, the compound of Formula I is a compound of Formula I-d.

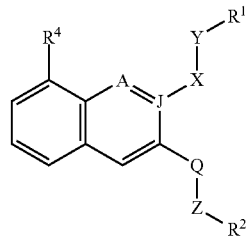
I-d

In another embodiment, the compound of Formula I is a compound of I-e.

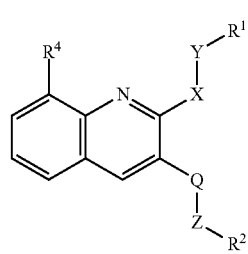
I-e

In another embodiment, in the compound of Formula I, I-a, I-b, I-c, O-d, or I-e, $R^4$ is H or methyl.

In another embodiment, in the compound of Formula I, I-a, I-b, I-c, I-d, or I-e, Q is absent or is $(C_1-C_4)$alkylene and Z is absent or is NH, $N(C_1-C_6)$alkyl, —NH—(C=O)—, —N($C_1-C_6$)alkyl-(C=O)—, O, or S.

In another embodiment, the compound of Formula I is a compound of Formula I-f or I-g, wherein $R^9$ is H or $CH_3$.

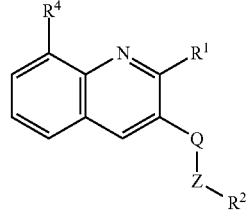
I-f

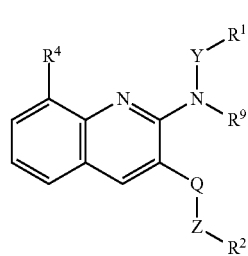
I-g

In another embodiment, in the compound of Formula I-g, Y is optionally substituted $(C_1-C_6)$alkylene, wherein up to two carbon atoms of the $(C_1-C_6)$alkylene are replaced by NH, $N(C_1-C_6)$alkyl, —NH—(C=O)—, —N($C_1-C_6$)alkyl-(C=O)—, or —(C=O)—.

In another embodiment, in the compound of Formula I-f or I-g, Q is $CH_2$ or $CH(CH_3)$.

In another embodiment, in the compound of Formula I-f or I-g, Z is absent or is —NH—, —NH—(C=O)—, or S.

In another embodiment, in the compound of Formula I-f or I-g, $R^1$ is halo, —OH, —$NH_2$, or cyano, or is ($C_1$-$C_6$)alkyl, ($C_1$-$C_6$)alkoxy, pyrrolidinyl, piperidinyl, piperizinyl, octahydro-pyridopyrazinyl, pyrazolyl, triazolyl, tetrazolyl, phenyl, pyridyl, imidazolyl, diazepinyl, morpholinyl, —$SO_2$—($C_1$-$C_6$)alkyl, —$SO_2$-aryl, —NH—($C_1$-$C_6$)alkyl, —NH—(($C_1$-$C_6$)alkyl)$_2$, octahydroisoquinolinyl, dihydroisoquinolinyl, benzimidazolyl, furanyl, pyrazinyl, thiazolyl, diazabicyclo[2.2.1]hept-2-yl, pyranyl, tetrahydropyranyl, any of which may be optionally substituted.

In another embodiment, in the compound of Formula I, I-a, I-b, I-c, I-d, I-e, I-f or I-g, le is bromo, —OH, —$NH_2$, cyano, —$CH_3$, —$OCH_3$, $SO_2$—$CH_3$,

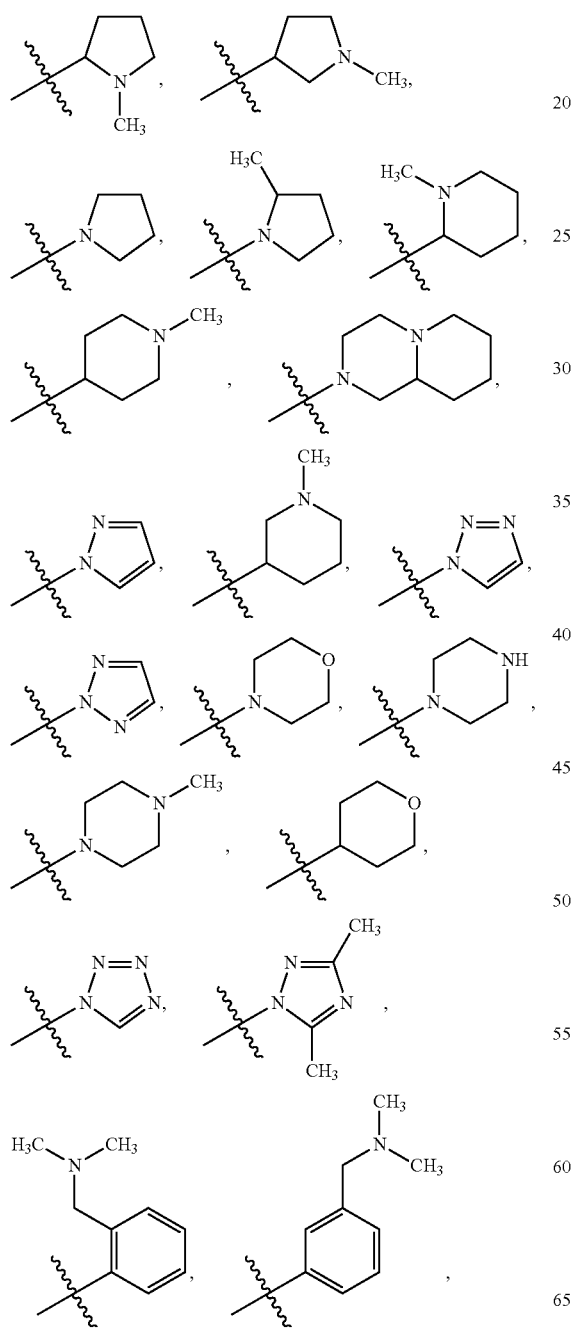

-continued

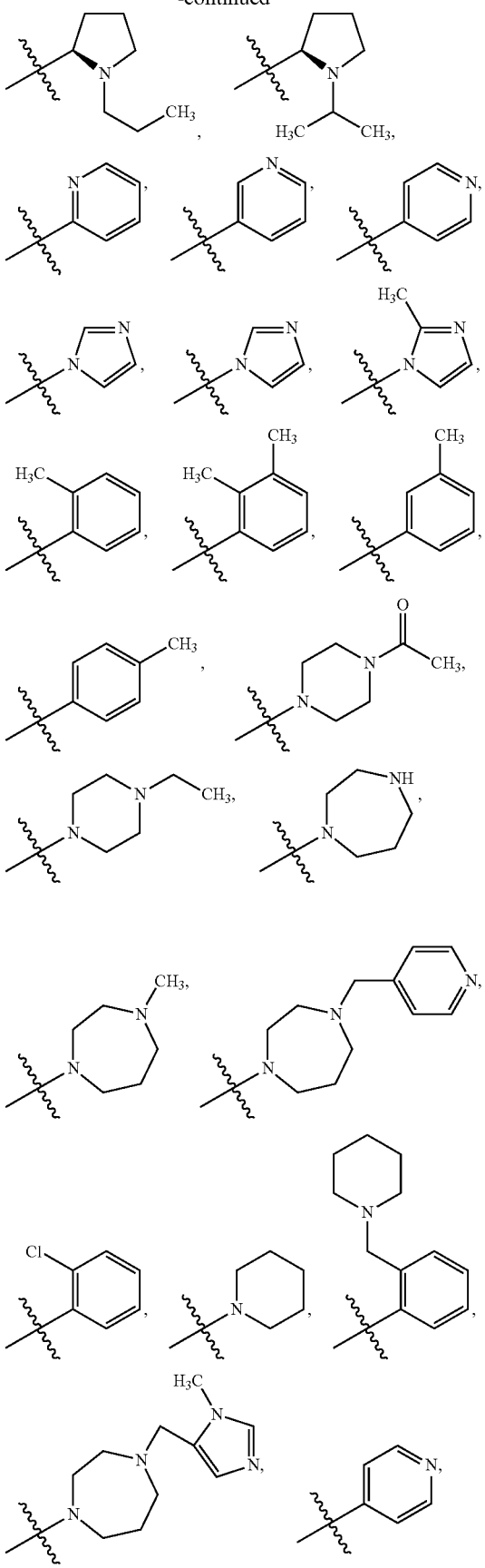

-continued
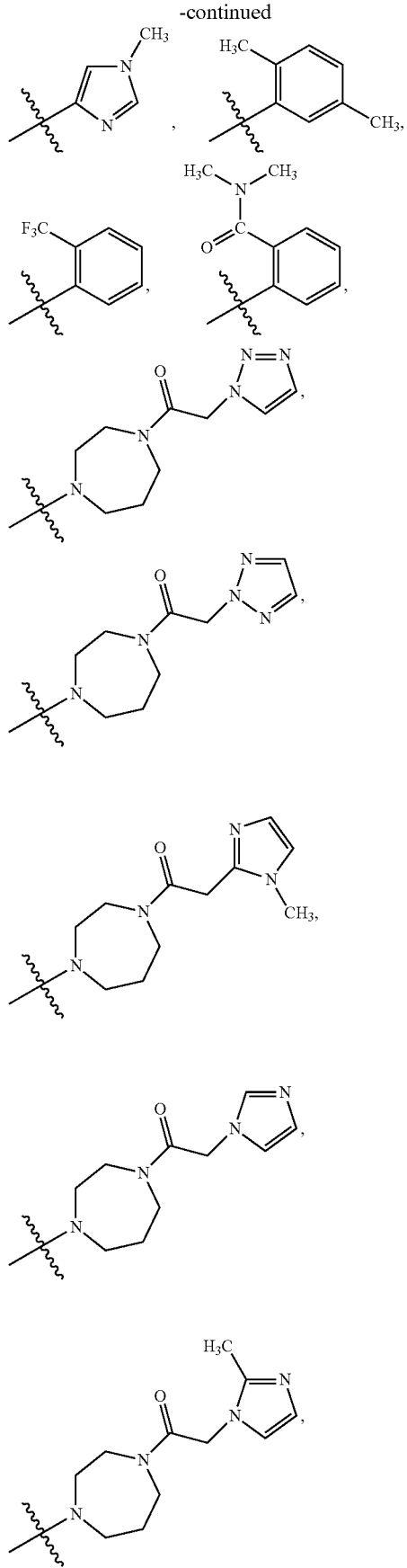
-continued
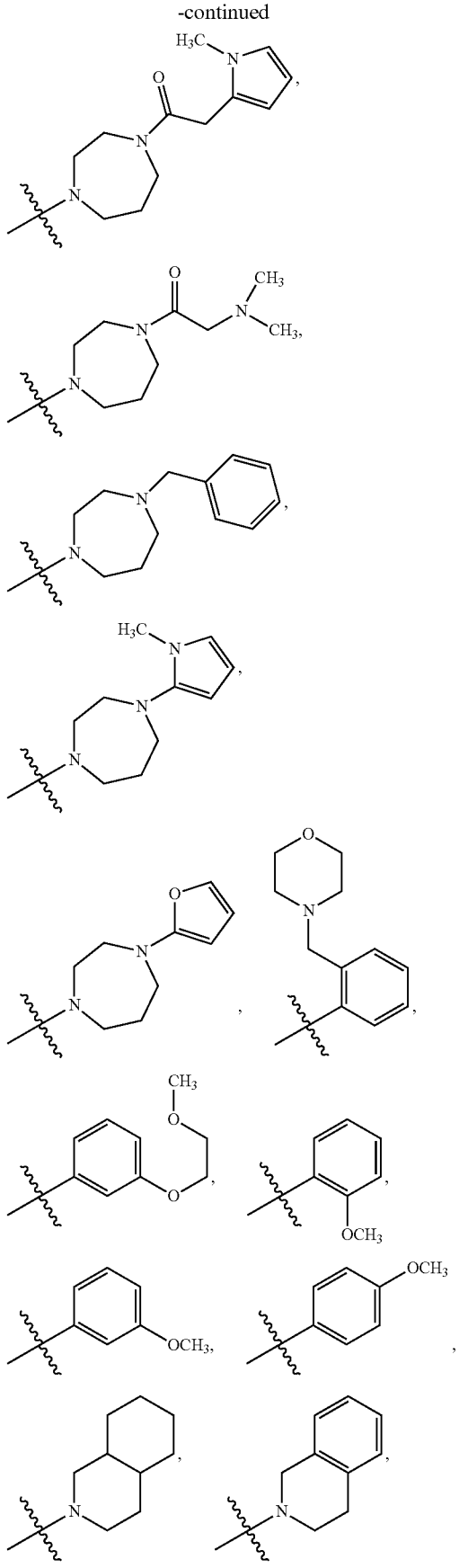

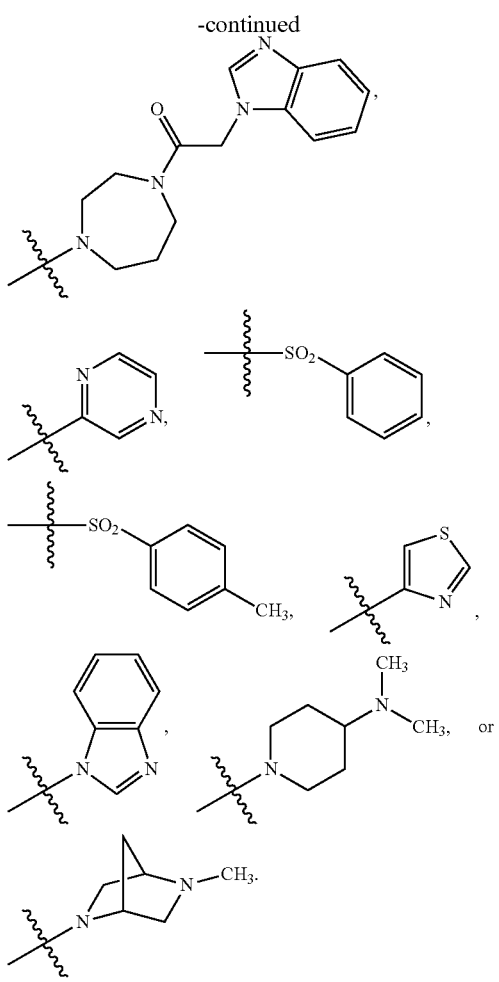
In another embodiment, in the compound of Formula I, I-a, I-b, I-c, I-d, I-e, I-f or I-g, $R^2$ is $NH_2$, purinyl, pyrazinyl, pyrazolopyrimidinyl, benzodioxinyl, phenyl, morpholinyl, oxadiazolyl, cyclopropyl, or pyridinyl, any of which may be optionally substituted.
In another embodiment, in the compound of Formula I, I-a, I-b, I-c, I-d, I-e, I-f or I-g, $R^2$ is $NH_2$,
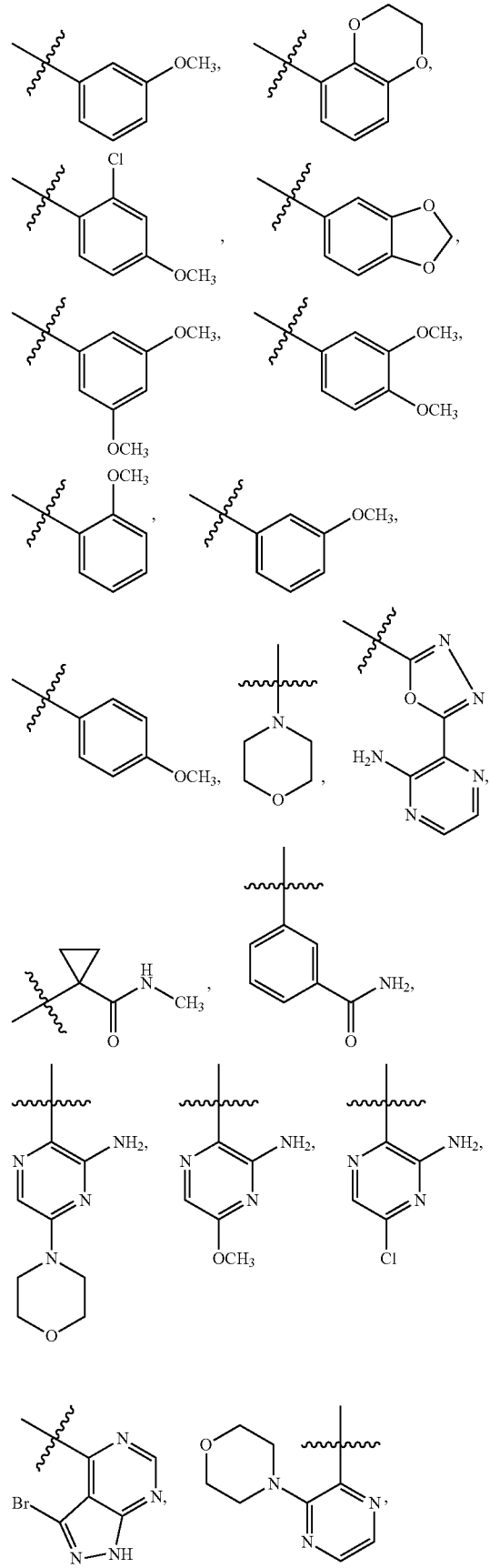
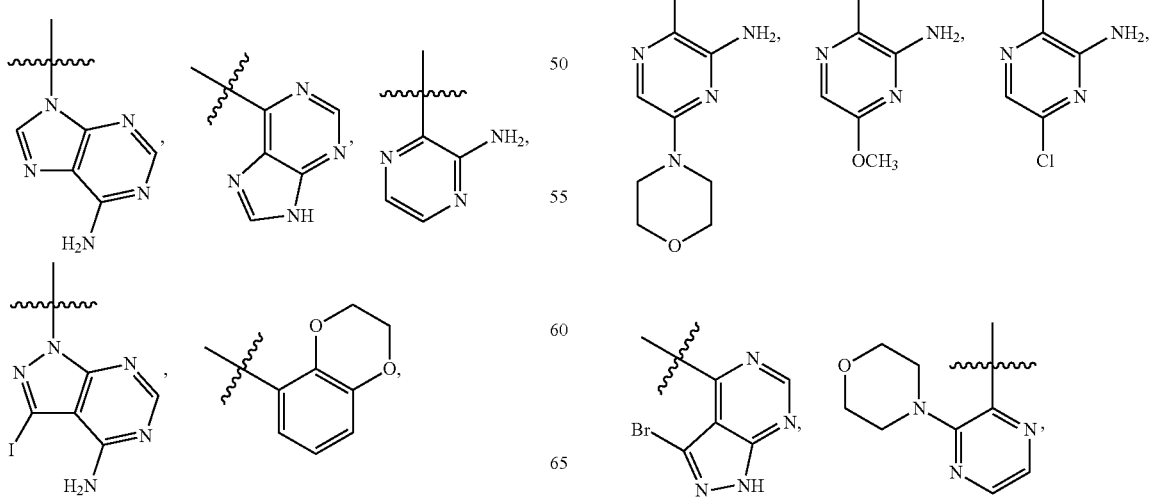

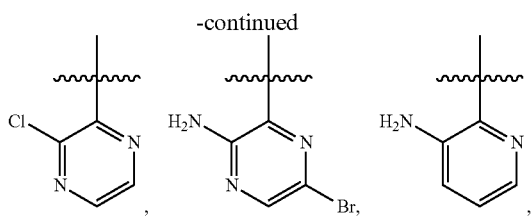

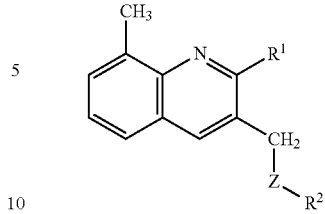
II-A1

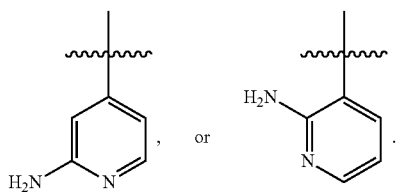

In another aspect, the provides a compound of Formula I which is a compound of Formula II.

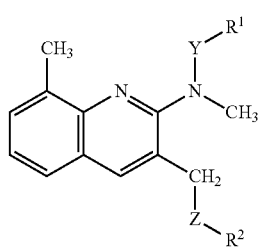
II-B1

II

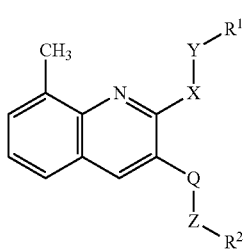

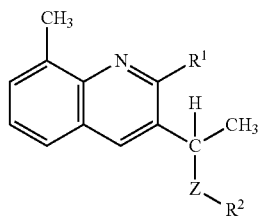
II-A2

In another aspect, the provides a compound of Formula I which is a compound of Formula II-A or II-B, wherein Ra is hydrogen or $C_1$-$C_6$-alkyl.

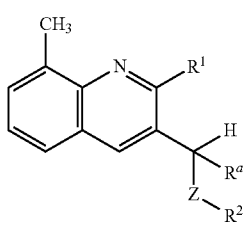
II-A

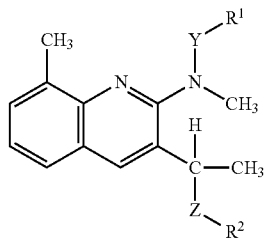
II-B2

II-B

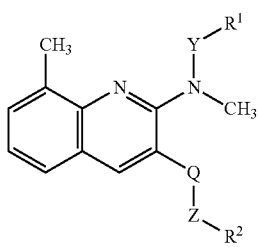

In one embodiment, the compound of Formula II is a compound of Formula II-A1, II-B1, II-A2, or II-B2.

In another embodiment, in the compound of Formula II, II-A, II, B, A1, II-B1, II-A2, or II-B2, Z is absent or is O, S, —NH— or —NH(C=O)— and $R^1$ and $R^2$ are as defined above.

Representative Compounds

Representative compounds of Formula I are depicted below. The examples are merely illustrative and do not limit the scope of the invention in any way. Compounds of the invention are named according to systematic application of the nomenclature rules agreed upon by the International Union of Pure and Applied Chemistry (IUPAC), International Union of Biochemistry and Molecular Biology (IUBMB), and the Chemical Abstracts Service (CAS). Specifically, names in Table 1 were generated using ACD/Labs naming software 8.00 release, product version 8.08 or higher.

TABLE 1

| Compound | Structure | Name |
|---|---|---|
| 1 | 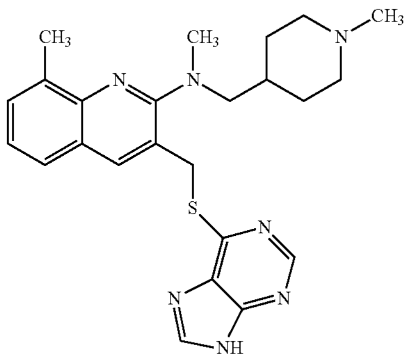 [SMILES: Cc1cccc2cc(CSc3ncnc4[nH]cnc34)c(N(C)CC3CCN(C)CC3)nc12] | N,8-dimethyl-N-[(1-methylpiperidin-4-yl)methyl]-3-[(9H-purin-6-ylthio)methyl]quinolin-2-amine |
| 2 | 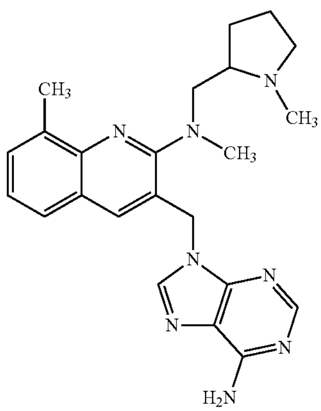 [SMILES: Cc1cccc2cc(Cn3cnc4c(N)ncnc43)c(N(C)CC3CCCN3C)nc12] | 3-[(6-amino-9H-purin-9-yl)methyl]-N,8-dimethyl-N-[(1-methylpyrrolidin-2-yl)methyl]quinolin-2-amine |
| 3 | 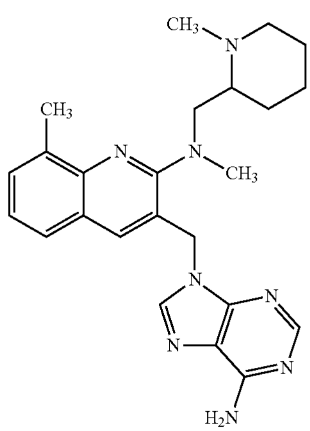 [SMILES: Cc1cccc2cc(Cn3cnc4c(N)ncnc43)c(N(C)CC3CCCCN3C)nc12] | 3-[(6-amino-9H-purin-9-yl)methyl]-N,8-dimethyl-N-[(1-methylpiperidin-2-yl)methyl]quinolin-2-amine |
| 4 | 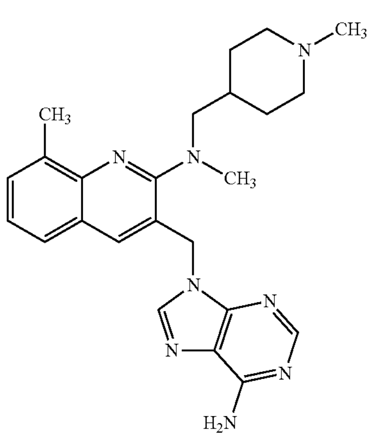 [SMILES: Cc1cccc2cc(Cn3cnc4c(N)ncnc43)c(N(C)CC3CCN(C)CC3)nc12] | 3-[(6-amino-9H-purin-9-yl)methyl]-N,8-dimethyl-N-[(1-methylpiperidin-4-yl)methyl]quinolin-2-amine |

TABLE 1-continued

| Compound | Structure | Name |
|---|---|---|
| 5 | 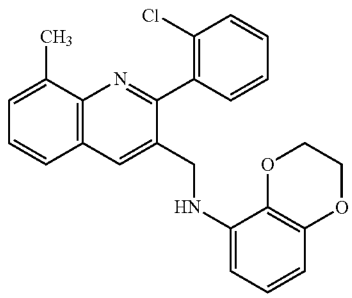 [SMILES: Cc1cccc2cc(CNc3cccc4c3OCCO4)c(-c3ccccc3Cl)nc12] | N-{[(2-(2-chlorophenyl)-8-methylquinolin-3-yl]methyl}-2,3-dihydro-1,4-benzodioxin-5-amine |
| 6 | 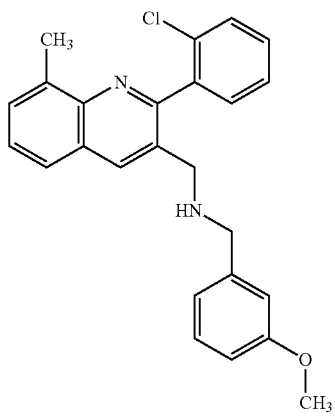 [SMILES: COc1cccc(CNCc2cc3cccc(C)c3nc2-c2ccccc2Cl)c1] | 1-[2-(2-chlorophenyl)-8-methylquinolin-3-yl]-N-{[3-(methyloxy)phenyl]methyl}methanamine |
| 7 | 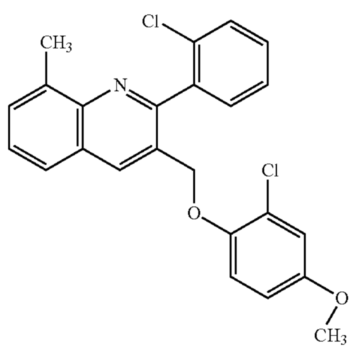 [SMILES: COc1ccc(OCc2cc3cccc(C)c3nc2-c2ccccc2Cl)c(Cl)c1] | 3-({[2-chloro-4-(methyloxy)phenyl]oxy}methyl)-2-(2-chlorophenyl)-8-methylquinoline |
| 8 | 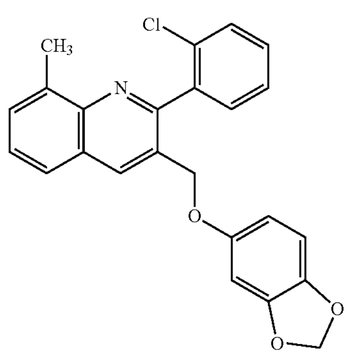 [SMILES: Cc1cccc2cc(COc3ccc4c(c3)OCO4)c(-c3ccccc3Cl)nc12] | 3-[(1,3-benzodioxol-5-yloxy)methyl]-2-(2-chlorophenyl)-8-methylquinoline |

TABLE 1-continued

| Compound | Structure | Name |
|---|---|---|
| 9 | 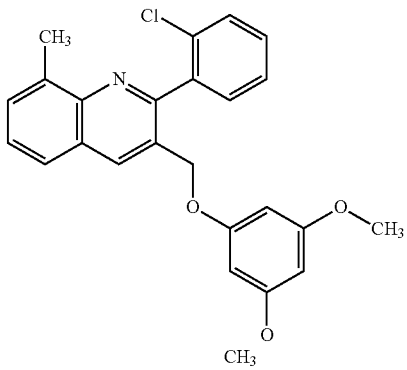 | N-{[2-(2-chlorophenyl)-8-methylquinolin-3-yl]methyl}-3,5-bis(methyloxy)aniline |
| 10 | 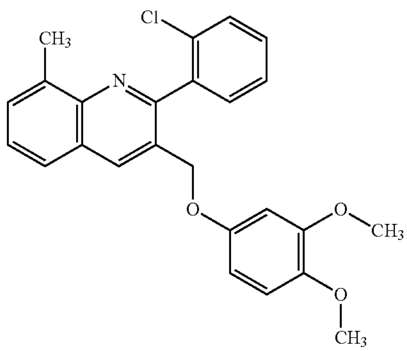 [SMILES: COc1ccc(OCc2cc3cccc(C)c3nc2-c2ccccc2Cl)cc1OC] | N-{[2-(2-chlorophenyl)-8-methylquinolin-3-yl]methyl}-3,4-bis(methyloxy)aniline |
| 11 | 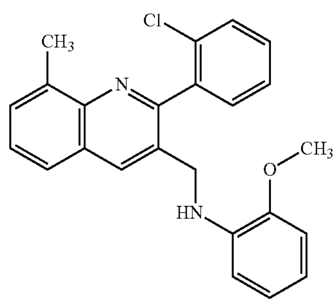 [SMILES: COc1ccccc1NCc1cc2cccc(C)c2nc1-c1ccccc1Cl] | N-{[2-(2-chlorophenyl)-8-methylquinolin-3-yl]methyl}-2-(methyloxy)aniline |
| 12 | 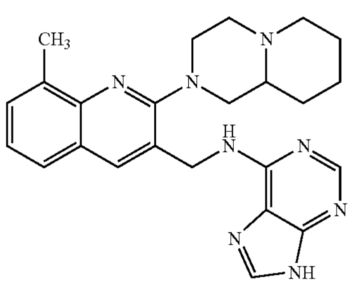 [SMILES: Cc1cccc2cc(CNc3ncnc4[nH]cnc34)c(N3CCN4CCCCC4C3)nc12] | N-{[8-methyl-2-(octahydro-2H-pyrido[1,2-a]pyrazin-2-yl)quinolin-3-yl]methyl}-9H-purin-6-amine |

TABLE 1-continued

| Compound | Structure | Name |
|---|---|---|
| 13 | 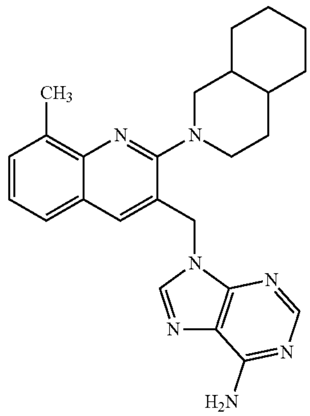 [SMILES: Cc1cccc2cc(Cn3cnc4c(N)ncnc43)c(N3CCC4CCCCC4C3)nc12] | 9-{[8-methyl-2-(octahydroisoquinolin-2(1H)-yl)quinolin-3-yl]methyl}-9H-purin-6-amine |
| 14 | 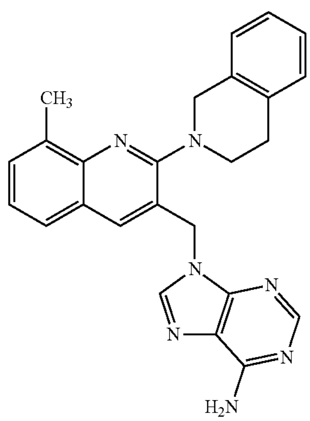 [SMILES: Cc1cccc2cc(Cn3cnc4c(N)ncnc43)c(N3CCc4ccccc4C3)nc12] | 9-{[2-(3,4-dihydroisoquinolin-2(1H)-yl)-8-methylquinolin-3-yl]methyl}-9H-purin-6-amine |
| 15 | 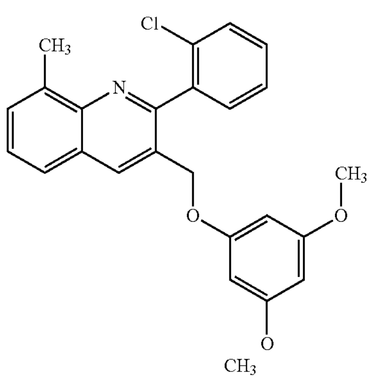 | 3-({[3,5-bis(methyloxy)phenyl]oxy}methyl)-2-(2-chlorophenyl)-8-methylquinoline |
| 16 | 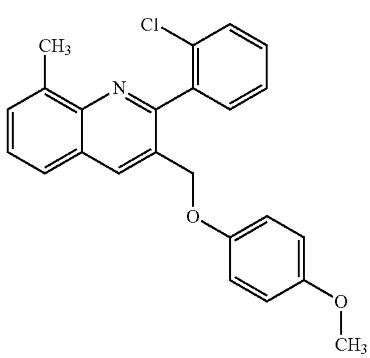 [SMILES: COc1ccc(OCc2cc3cccc(C)c3nc2-c2ccccc2Cl)cc1] | 2-(2-chlorophenyl)-8-methyl-3-({[4-(methyloxy)phenyl]oxy}methyl)quinoline |

TABLE 1-continued

| Compound | Structure | Name |
|---|---|---|
| 17 | 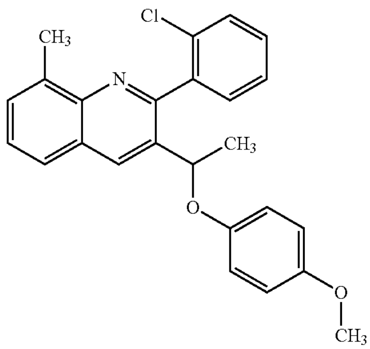 [SMILES: COc1ccc(OC(C)c2cc3cccc(C)c3nc2-c2ccccc2Cl)cc1] | 2-(2-chlorophenyl)-8-methyl-3-(1-{[4-(methyloxy)phenyl]oxy}ethyl)quinoline |
| 18 | 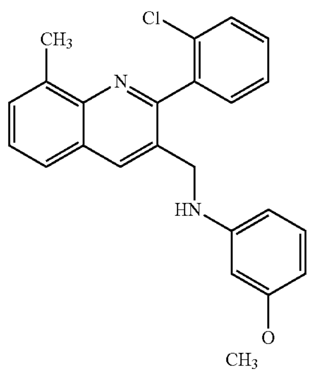 | N-{[2-(2-chlorophenyl)-8-methylquinolin-3-yl]methyl}-3-(methyloxy)aniline |
| 19 | 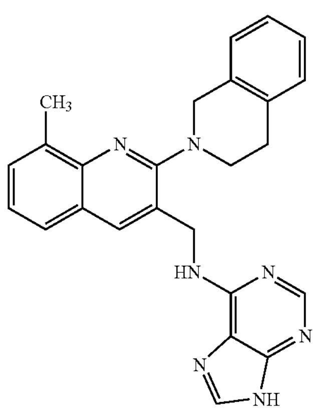 [SMILES: Cc1cccc2cc(CNc3ncnc4[nH]cnc34)c(N3CCc4ccccc4C3)nc12] | N-{[2-(3,4-dihydroisoquinolin-2(1H)-yl)-8-methylquinolin-3-yl]methyl}-9H-purin-6-amine |
| 20 | 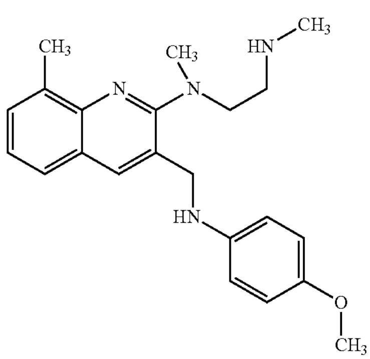 [SMILES: CNCCN(C)c1nc2c(C)cccc2cc1CNc1ccc(OC)cc1] | N,N'-dimethyl-N-[8-methyl-3-({[4-(methyloxy)phenyl]amino}methyl)quinolin-2-yl]ethane-1,2-diamine |

TABLE 1-continued

| Compound | Structure | Name |
|---|---|---|
| 21 | 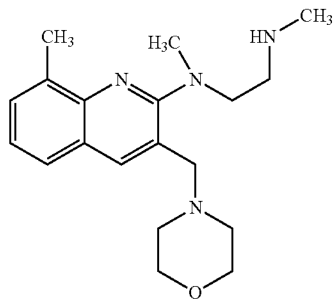 [SMILES: CNCCN(C)c1nc2c(C)cccc2cc1CN1CCOCC1] | N,N'-dimethyl-N-[8-methyl-3-(morpholin-4-ylmethyl)quinolin-2-yl]ethane-1,2-diamine |
| 22 | 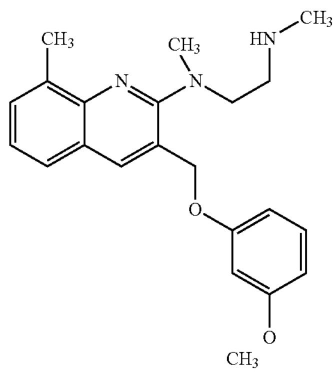 | N,N'-dimethyl-N-[8-methyl-3-({[3-(methyloxy)phenyl]oxy}methyl)quinolin-2-yl]ethane-1,2-diamine |
| 23 | 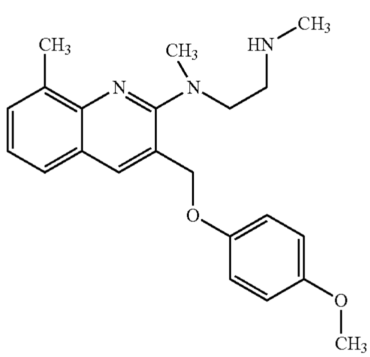 [SMILES: CNCCN(C)c1nc2c(C)cccc2cc1COc1ccc(OC)cc1] | N,N'-dimethyl-N-[8-methyl-3-({[4-(methyloxy)phenyl]oxy}methyl)quinolin-2-yl]ethane-1,2-diamine |
| 24 | 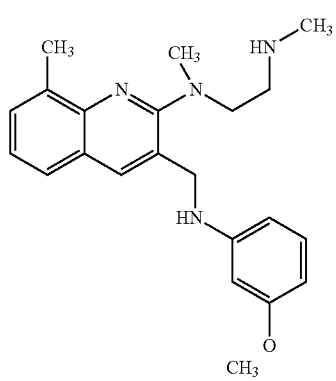 | N,N'-dimethyl-N-[8-methyl-3-({[3-(methyloxy)phenyl]amino}methyl)quinolin-2-yl]ethane-1,2-diamine |

TABLE 1-continued

| Compound | Structure | Name |
|---|---|---|
| 25 | 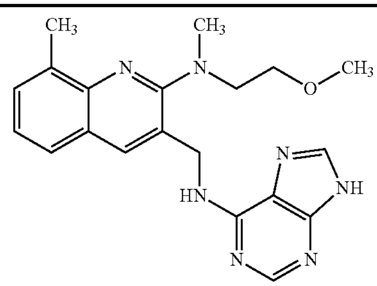 | N,8-dimethyl-N-[2-(methyloxy)ethyl]-3-[(9H-purin-6-ylamino)methyl]quinolin-2-amine |
| 26 | 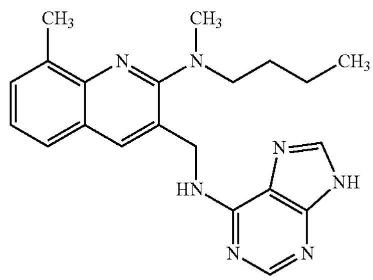 [SMILES: CCCCN(C)c1nc2c(C)cccc2cc1CNc1ncnc2[nH]cnc12] | N-butyl-N,8-dimethyl-3-[(9H-purin-6-ylamino)methyl]quinolin-2-amine |
| 27 | 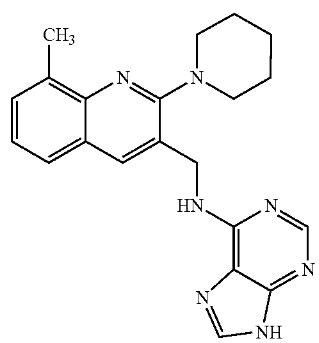 [SMILES: Cc1cccc2cc(CNc3ncnc4[nH]cnc34)c(N3CCCCC3)nc12] | N-[(8-methyl-2-piperidin-1-ylquinolin-3-yl)methyl]-9H-purin-6-amine |
| 28 | 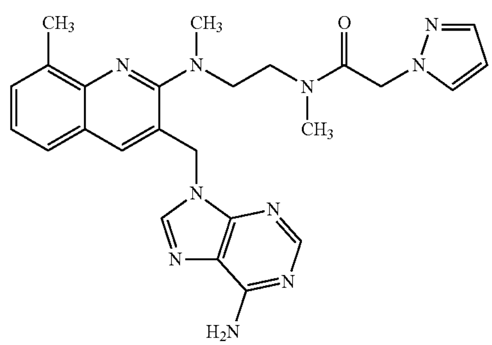 [SMILES: Cc1cccc2cc(Cn3cnc4c(N)ncnc43)c(N(C)CCN(C)C(=O)Cn3cccn3)nc12] | N-{2-[{3-[(6-amino-9H-purin-9-yl)methyl]-8-methylquinolin-2-yl}(methyl)amino]ethyl}-N-methyl-2-(1H-pyrazol-1-yl)acetamide |
| 29 | 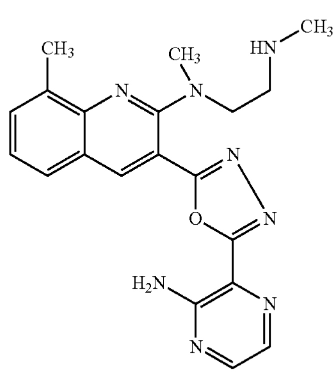 [SMILES: CNCCN(C)c1nc2c(C)cccc2cc1-c1nnc(-c2nccnc2N)o1] | N-{3-[5-(3-aminopyrazin-2-yl)-1,3,4-oxadiazol-2-yl]-8-methylquinolin-2-yl}-N,N'-dimethylethane-1,2-diamine |

TABLE 1-continued
| Compound | Structure | Name |
|---|---|---|
| 30 | 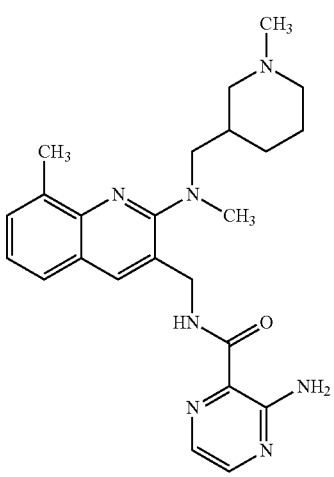 [SMILES: Cc1cccc2cc(CNC(=O)c3nccnc3N)c(N(C)CC3CCCN(C)C3)nc12] | 3-amino-N-[(8-methyl-2-{methyl[(1-methylpiperidin-3-yl)methyl]amino}quinolin-3-yl)methyl]pyrazine-2-carboxamide |
| 31 | 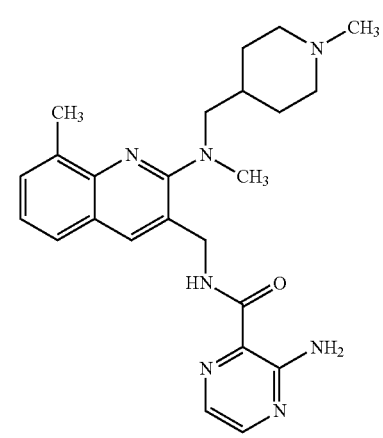 [SMILES: Cc1cccc2cc(CNC(=O)c3nccnc3N)c(N(C)CC3CCN(C)CC3)nc12] | 3-amino-N-[(8-methyl-2-{methyl[(1-methylpiperidin-4-yl)methyl]amino}quinolin-3-yl)methyl]pyrazine-2-carboxamide |
| 32 | 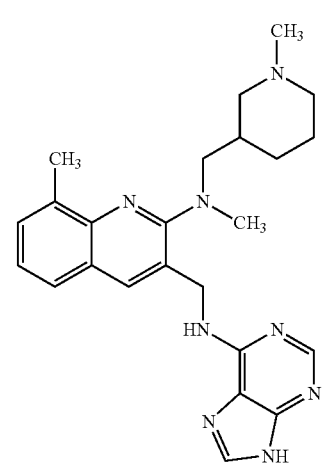 [SMILES: Cc1cccc2cc(CNc3ncnc4[nH]cnc34)c(N(C)CC3CCCN(C)C3)nc12] | N,8-dimethyl-N-[(1-methylpiperidin-3-yl)methyl]-3-[(9H-purin-6-ylamino)methyl]quinolin-2-amine |

TABLE 1-continued

| Compound | Structure | Name |
|---|---|---|
| 33 | 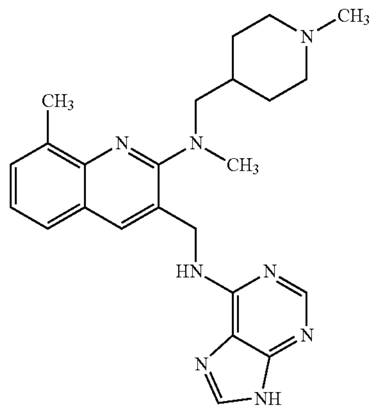 [SMILES: Cc1cccc2cc(CNc3ncnc4[nH]cnc34)c(N(C)CC3CCN(C)CC3)nc12] | N,8-dimethyl-N-[(1-methylpiperidin-4-yl)methyl]-3-[(9H-purin-6-ylamino)methyl]quinolin-2-amine |
| 34 | 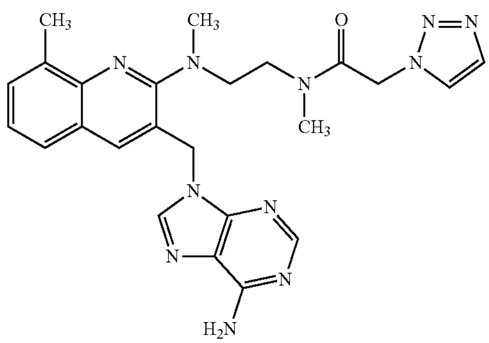 [SMILES: Cc1cccc2cc(Cn3cnc4c(N)ncnc43)c(N(C)CCN(C)C(=O)Cn3ccnn3)nc12] | N-{2-[{3-[(6-amino-9H-purin-9-yl)methyl]-8-methylquinolin-2-yl}(methyl)amino]ethyl}-N-methyl-2-(1H-1,2,3-triazol-1-yl)acetamide |
| 35 | 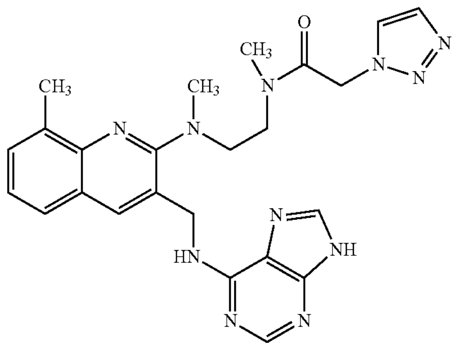 [SMILES: Cc1cccc2cc(CNc3ncnc4[nH]cnc34)c(N(C)CCN(C)C(=O)Cn3ccnn3)nc12] | N-methyl-N-[2-(methyl{8-methyl-3-[(9H-purin-6-ylamino)methyl]quinolin-2-yl}amino)ethyl]-2-(1H-1,2,3-triazol-1-yl)acetamide |
| 36 | 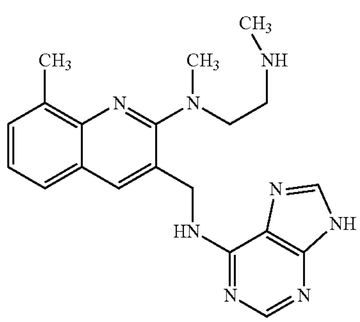 [SMILES: CNCCN(C)c1nc2c(C)cccc2cc1CNc1ncnc2[nH]cnc12] | N,N'-dimethyl-N-{8-methyl-3-[(9H-purin-6-ylamino)methyl]quinolin-2-yl}ethane-1,2-diamine |

TABLE 1-continued

| Compound | Structure | Name |
|---|---|---|
| 37 | 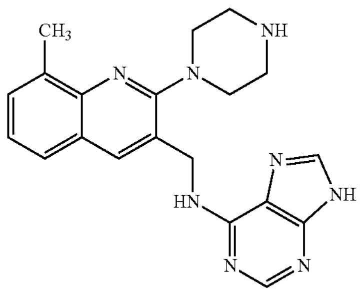 [SMILES: Cc1cccc2cc(CNc3ncnc4[nH]cnc34)c(N3CCNCC3)nc12] | N-[(8-methyl-2-piperazin-1-ylquinolin-3-yl)methyl]-9H-purin-6-amine |
| 38 | 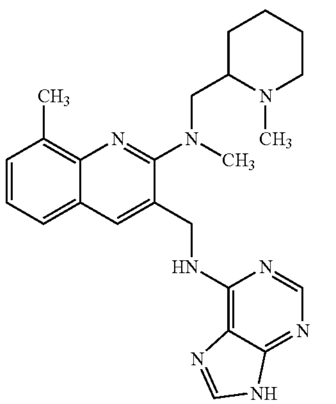 [SMILES: Cc1cccc2cc(CNc3ncnc4[nH]cnc34)c(N(C)CC3CCCCN3C)nc12] | N,8-dimethyl-N-[(1-methylpiperidin-2-yl)methyl]-3-[(9H-purin-6-ylamino)methyl]quinolin-2-amine |
| 39 | 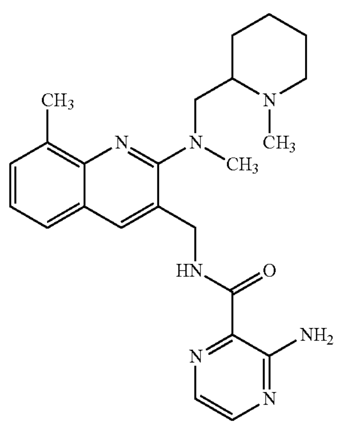 [SMILES: Cc1cccc2cc(CNC(=O)c3nccnc3N)c(N(C)CC3CCCCN3C)nc12] | 3-amino-N-[(8-methyl-2-{methyl[(1-methylpiperidin-2-yl)methyl]amino}quinolin-3-yl)methyl]pyrazine-2-carboxamide |
| 40 | 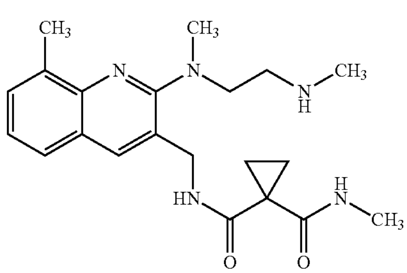 [SMILES: CNCCN(C)c1nc2c(C)cccc2cc1CNC(=O)C1(C(=O)NC)CC1] | N-methyl-N'-[(8-methyl-2-{methyl[2-(methylamino)ethyl]amino}quinolin-3-yl)methyl]cyclopropane-1,1-dicarboxamide |

TABLE 1-continued

| Compound | Structure | Name |
|---|---|---|
| 41 | 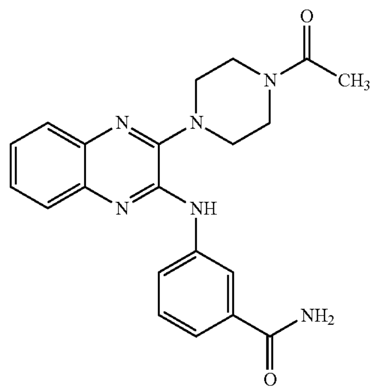 [SMILES: CC(=O)N1CCN(c2nc3ccccc3nc2Nc2cccc(C(N)=O)c2)CC1] | 3-{[3-(4-acetylpiperazin-1-yl)quinoxalin-2-yl]amino}benzamide |
| 42 | 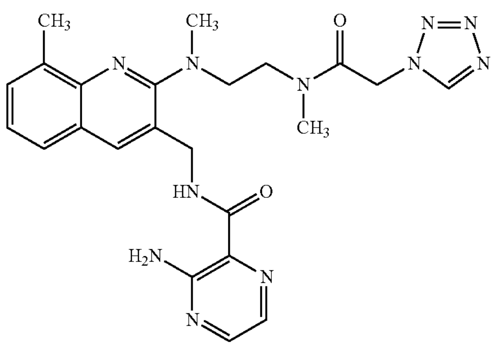 [SMILES: Cc1cccc2cc(CNC(=O)c3nccnc3N)c(N(C)CCN(C)C(=O)Cn3cnnn3)nc12] | 3-amino-N-{[8-methyl-2-(methyl{2-[methyl(1H-tetrazol-1-ylacetyl)amino]ethyl}amino)quinolin-3-yl]methyl}pyrazine-2-carboxamide |
| 43 | 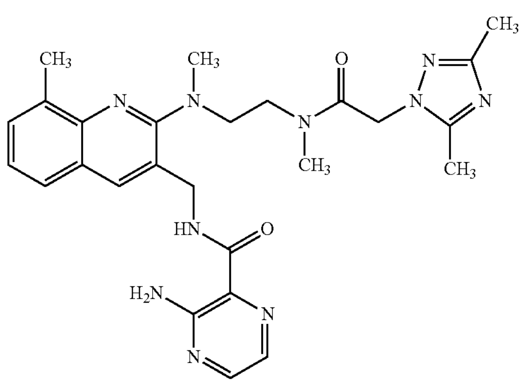 [SMILES: Cc1nc(C)n(CC(=O)N(C)CCN(C)c2nc3c(C)cccc3cc2CNC(=O)c2nccnc2N)n1] | 3-amino-N-({2-[(2-{[(3,5-dimethyl-1H-1,2,4-triazol-1-yl)acetyl](methyl)amino}ethyl)(methyl)amino]-8-methylquinolin-3-yl}methyl)pyrazine-2-carboxamide |
| 44 | 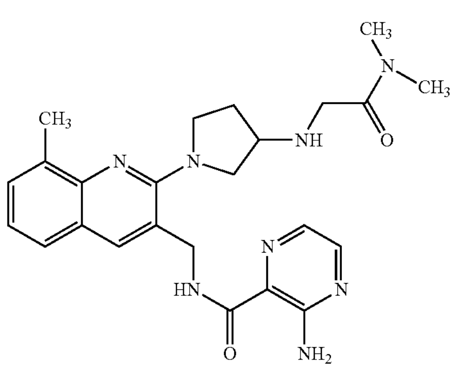 [SMILES: Cc1cccc2cc(CNC(=O)c3nccnc3N)c(N3CCC(NCC(=O)N(C)C)C3)nc12] | 3-amino-N-{[2-(3-{[2-(dimethylamino)-2-oxoethyl]amino}pyrrolidin-1-yl)-8-methylquinolin-3-yl]methyl}pyrazine-2-carboxamide |

TABLE 1-continued

| Compound | Structure | Name |
|---|---|---|
| 45 | 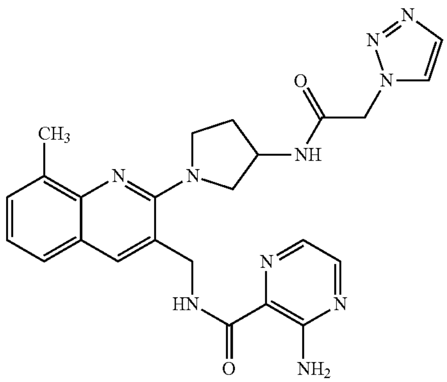 [SMILES: Cc1cccc2cc(CNC(=O)c3nccnc3N)c(N3CCC(NC(=O)Cn4ccnn4)C3)nc12] | 3-amino-N-[(8-methyl-2-{3-[(1H-1,2,3-triazol-1-ylacetyl)amino]pyrrolidin-1-yl}quinolin-3-yl)methyl]pyrazine-2-carboxamide |
| 46 | 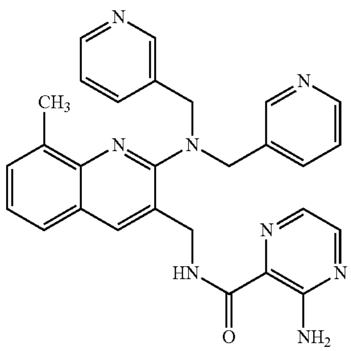 [SMILES: Cc1cccc2cc(CNC(=O)c3nccnc3N)c(N(Cc3cccnc3)Cc3cccnc3)nc12] | 3-amino-N-({2-[bis(pyridin-3-ylmethyl)amino]-8-methylquinolin-3-yl}methyl)pyrazine-2-carboxamide |
| 47 | 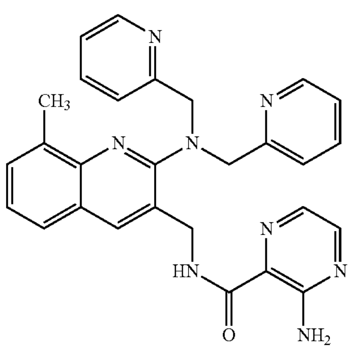 [SMILES: Cc1cccc2cc(CNC(=O)c3nccnc3N)c(N(Cc3ccccn3)Cc3ccccn3)nc12] | 3-amino-N-({2-[bis(pyridin-2-ylmethyl)amino]-8-methylquinolin-3-yl}methyl)pyrazine-2-carboxamide |
| 48 | 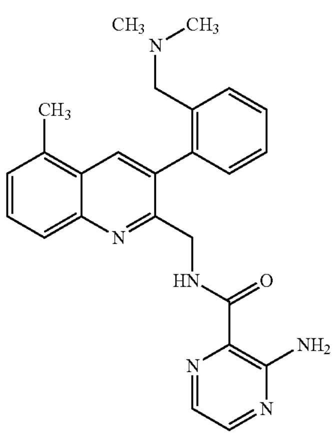 | 3-amino-N-[(5-chloro-3-{2-[(dimethylamino)methyl]phenyl}quinolin-2-yl)methyl]pyrazine-2-carboxamide |

TABLE 1-continued

| Compound | Structure | Name |
|---|---|---|
| 49 | 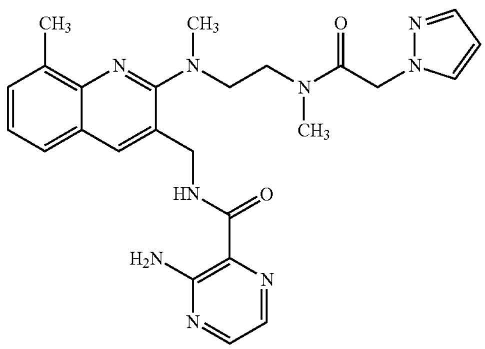 [SMILES: Cc1cccc2cc(CNC(=O)c3nccnc3N)c(N(C)CCN(C)C(=O)Cn3cccn3)nc12] | 3-amino-N-{[8-methyl-2-(methyl{2-[methyl(1H-pyrazol-1-ylacetyl)amino]ethyl}amino)quinolin-3-yl]methyl}pyrazine-2-carboxamide |
| 50 | 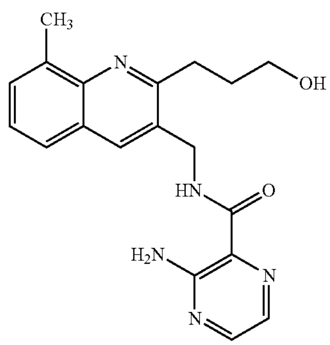 [SMILES: Cc1cccc2cc(CNC(=O)c3nccnc3N)c(CCCO)nc12] | 3-amino-N-{[2-(3-hydroxypropyl)-8-methylquinolin-3-yl]methyl}pyrazine-2-carboxamide |
| 51 | 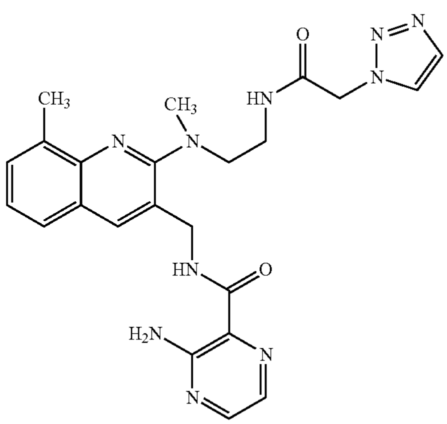 [SMILES: Cc1cccc2cc(CNC(=O)c3nccnc3N)c(N(C)CCNC(=O)Cn3ccnn3)nc12] | 3-amino-N-{[8-methyl-2-(methyl{2-[(1H-1,2,3-triazol-1-ylacetyl)amino]ethyl}amino)quinolin-3-yl]methyl}pyrazine-2-carboxamide |
| 52 | 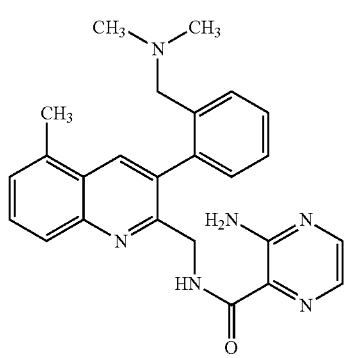 [SMILES: Cc1cccc2nc(CNC(=O)c3nccnc3N)c(-c3ccccc3CN(C)C)cc12] | 3-amino-N-[(3-{2-[(dimethylamino)methyl]phenyl}-5-methylquinolin-2-yl)methyl]pyrazine-2-carboxamide |

TABLE 1-continued

| Compound | Structure | Name |
|---|---|---|
| 53 | 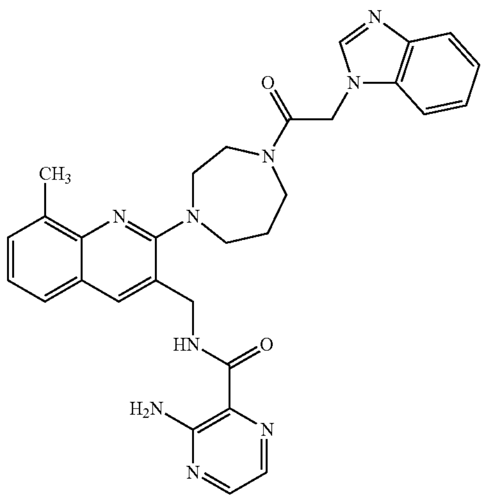 [SMILES: Cc1cccc2cc(CNC(=O)c3nccnc3N)c(N3CCCN(C(=O)Cn4cnc5ccccc54)CC3)nc12] | 3-amino-N-({2-[4-(1H-benzimidazol-1-ylacetyl)-1,4-diazepan-1-yl]-8-methylquinolin-3-yl}methyl)pyrazine-2-carboxamide |
| 54 | 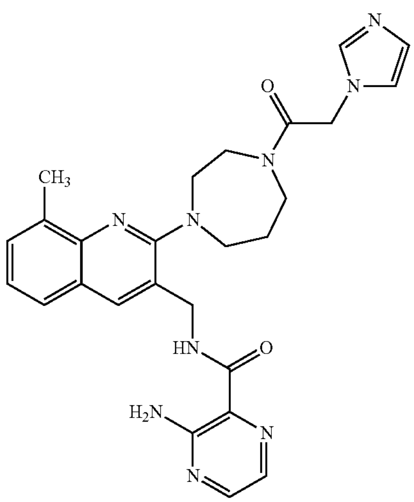 [SMILES: Cc1cccc2cc(CNC(=O)c3nccnc3N)c(N3CCCN(C(=O)Cn4ccnc4)CC3)nc12] | 3-amino-N-({2-[4-(1H-imidazol-1-ylacetyl)-1,4-diazepan-1-yl]-8-methylquinolin-3-yl}methyl)pyrazine-2-carboxamide |
| 55 | 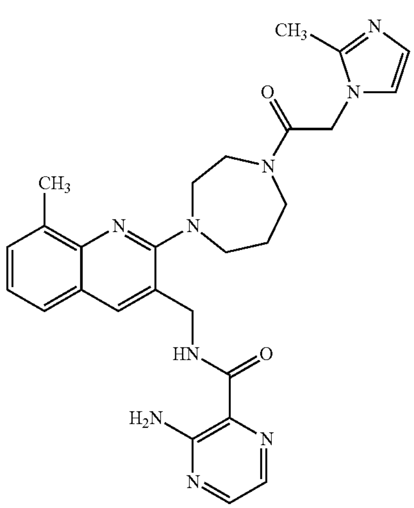 [SMILES: Cc1cccc2cc(CNC(=O)c3nccnc3N)c(N3CCCN(C(=O)Cn4ccnc4C)CC3)nc12] | 3-amino-N-[(8-methyl-2-{4-[(2-methyl-1H-imidazol-1-yl)acetyl]-1,4-diazepan-1-yl}quinolin-3-yl)methyl]pyrazine-2-carboxamide |

TABLE 1-continued
| Compound | Structure | Name |
|---|---|---|
| 56 | 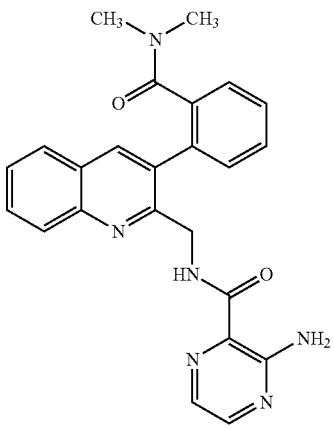 [SMILES: CN(C)C(=O)c1ccccc1-c1cc2ccccc2nc1CNC(=O)c1nccnc1N] | 3-amino-N-[(3-{2-[(dimethylamino)carbonyl]phenyl}quinolin-2-yl)methyl]pyrazine-2-carboxamide |
| 57 | 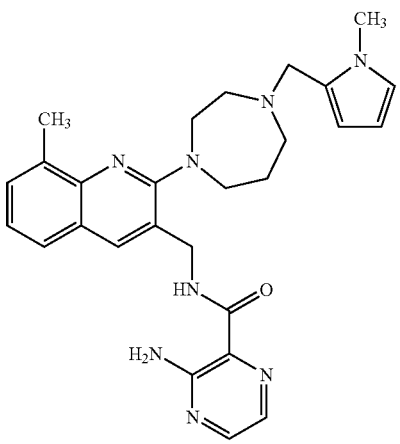 [SMILES: Cc1cccc2cc(CNC(=O)c3nccnc3N)c(N3CCCN(Cc4cccn4C)CC3)nc12] | 3-amino-N-[(8-methyl-2-{4-[(1-methyl-1H-pyrrol-2-yl)methyl]-1,4-diazepan-1-yl}quinolin-3-yl)methyl]pyrazine-2-carboxamide |
| 58 | 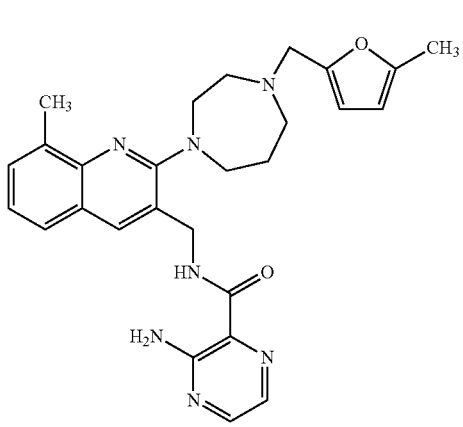 [SMILES: Cc1ccc(CN2CCCN(c3nc4c(C)cccc4cc3CNC(=O)c3nccnc3N)CC2)o1] | 3-amino-N-[(8-methyl-2-{4-[(5-methylfuran-2-yl)methyl]-1,4-diazepan-1-yl}quinolin-3-yl)methyl]pyrazine-2-carboxamide |

TABLE 1-continued
| Compound | Structure | Name |
|---|---|---|
| 59 | 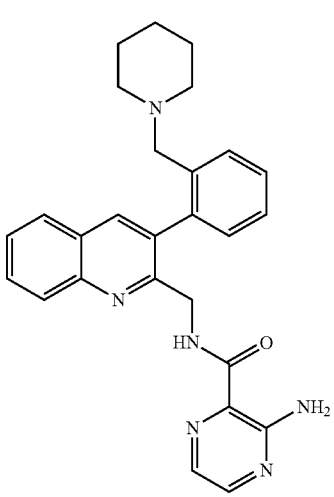 [SMILES: Nc1nccnc1C(=O)NCc1nc2ccccc2cc1-c1ccccc1CN1CCCCC1] | 3-amino-N-({3-[2-(piperidin-1-ylmethyl)phenyl]quinolin-2-yl}methyl)pyrazine-2-carboxamide |
| 60 | 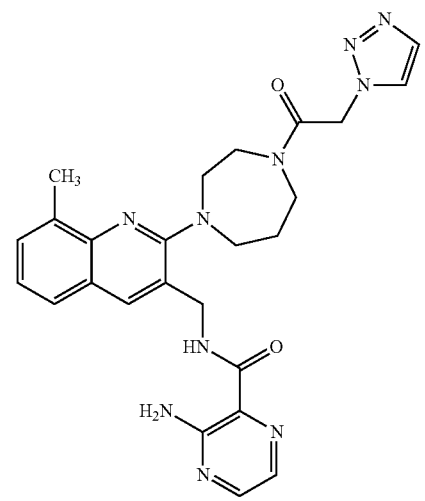 [SMILES: Cc1cccc2cc(CNC(=O)c3nccnc3N)c(N3CCCN(C(=O)Cn4ccnn4)CC3)nc12] | 3-amino-N-({8-methyl-2-[4-(1H-1,2,3-triazol-1-ylacetyl)-1,4-diazepan-1-yl]quinolin-3-yl}methyl)pyrazine-2-carboxamide |
| 61 | 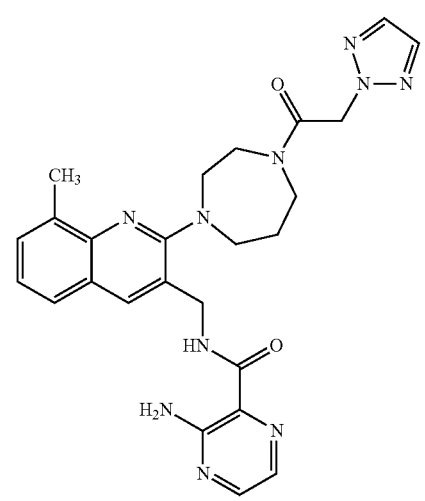 [SMILES: Cc1cccc2cc(CNC(=O)c3nccnc3N)c(N3CCCN(C(=O)Cn4nccn4)CC3)nc12] | 3-amino-N-({8-methyl-2-[4-(2H-1,2,3-triazol-2-ylacetyl)-1,4-diazepan-1-yl]quinolin-3-yl}methyl)pyrazine-2-carboxamide |

| Compound | Structure | Name |
|---|---|---|
| 62 | 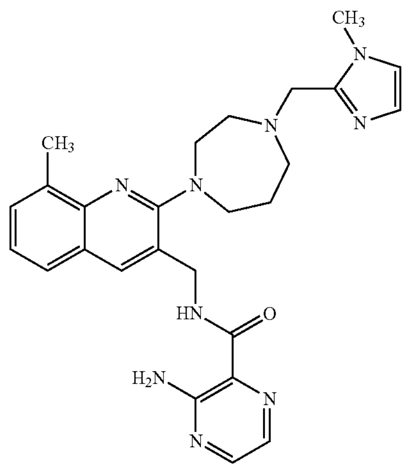 [SMILES: Cc1cccc2cc(CNC(=O)c3nccnc3N)c(N3CCCN(Cc4nccn4C)CC3)nc12] | 3-amino-N-[(8-methyl-2-{4-[(1-methyl-1H-imidazol-2-yl)methyl]-1,4-diazepan-1-yl}quinolin-3-yl)methyl]pyrazine-2-carboxamide |
| 63 | 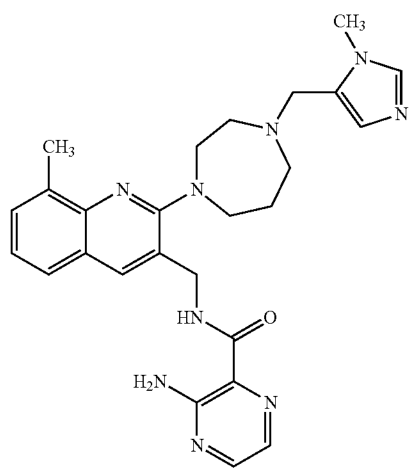 [SMILES: Cc1cccc2cc(CNC(=O)c3nccnc3N)c(N3CCCN(Cc4cncn4C)CC3)nc12] | 3-amino-N-[(8-methyl-2-{4-[(1-methyl-1H-imidazol-5-yl)methyl]-1,4-diazepan-1-yl}quinolin-3-yl)methyl]pyrazine-2-carboxamide |
| 64 | 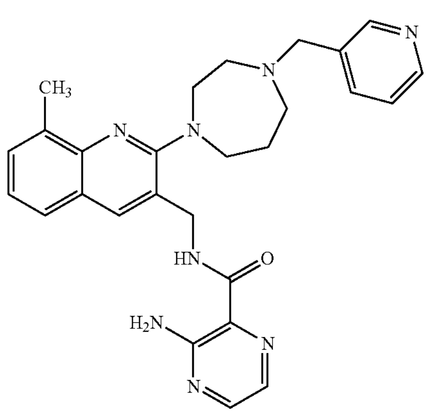 [SMILES: Cc1cccc2cc(CNC(=O)c3nccnc3N)c(N3CCCN(Cc4cccnc4)CC3)nc12] | 3-amino-N-({8-methyl-2-[4-(pyridin-3-ylmethyl)-1,4-diazepan-1-yl]quinolin-3-yl}methyl)pyrazine-2-carboxamide |

TABLE 1-continued

| Compound | Structure | Name |
|---|---|---|
| 65 | 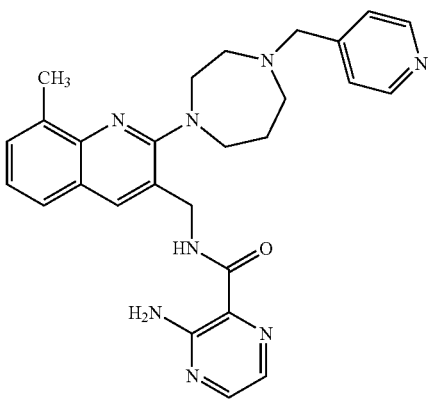 [SMILES: Cc1cccc2cc(CNC(=O)c3nccnc3N)c(N3CCCN(Cc4ccncc4)CC3)nc12] | 3-amino-N-({8-methyl-2-[4-(pyridin-4-ylmethyl)-1,4-diazepan-1-yl]quinolin-3-yl}methyl)pyrazine-2-carboxamide |
| 66 | 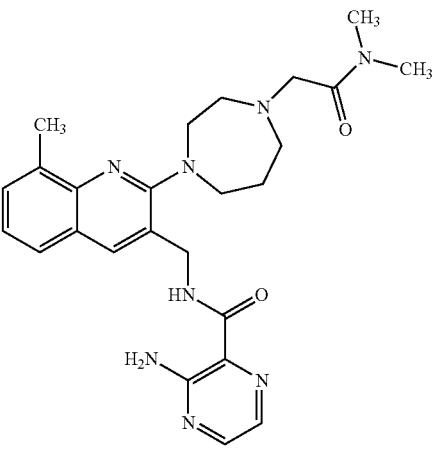 [SMILES: Cc1cccc2cc(CNC(=O)c3nccnc3N)c(N3CCCN(CC(=O)N(C)C)CC3)nc12] | 3-amino-N-[(2-{4-[2-(dimethylamino)-2-oxoethyl]-1,4-diazepan-1-yl}-8-methylquinolin-3-yl)methyl]pyrazine-2-carboxamide |
| 67 | 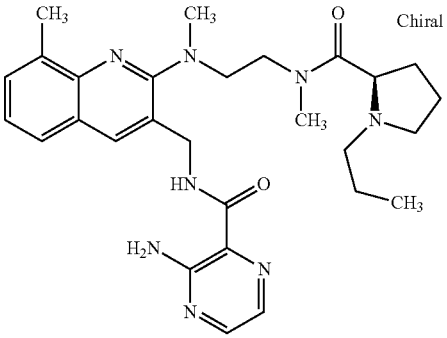 [SMILES: CCCN1CCC[C@@H]1C(=O)N(C)CCN(C)c1nc2c(C)cccc2cc1CNC(=O)c1nccnc1N] | 3-amino-N-{[8-methyl-2-(methyl{2-[methyl(1-propyl-D-prolyl)amino]ethyl}amino)quinolin-3-yl]methyl}pyrazine-2-carboxamide |
| 68 | 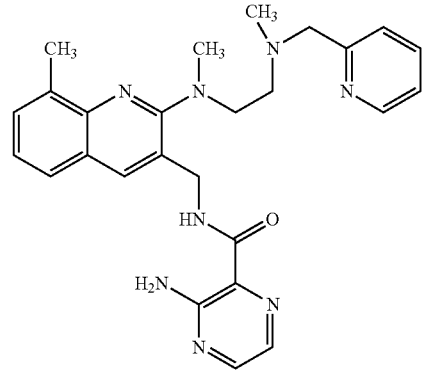 [SMILES: Cc1cccc2cc(CNC(=O)c3nccnc3N)c(N(C)CCN(C)Cc3ccccn3)nc12] | 3-amino-N-{[8-methyl-2-(methyl{2-[methyl(pyridin-2-ylmethyl)amino]ethyl}amino)quinolin-3-yl]methyl}pyrazine-2-carboxamide |

TABLE 1-continued
| Compound | Structure | Name |
|---|---|---|
| 69 | 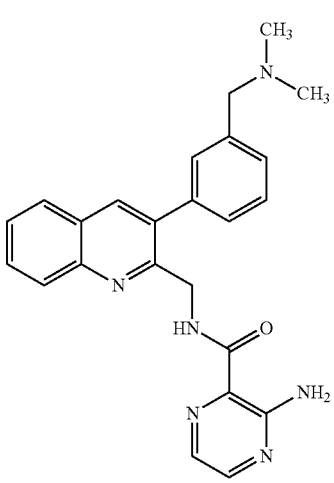 [SMILES: CN(C)Cc1cccc(-c2cc3ccccc3nc2CNC(=O)c2nccnc2N)c1] | 3-amino-N-[(3-{3-[(dimethylamino)methyl]phenyl}quinolin-2-yl)methyl]pyrazine-2-carboxamide |
| 70 | 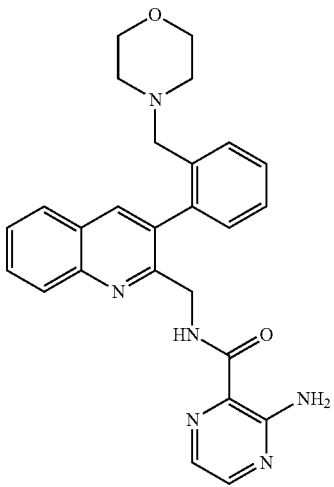 [SMILES: Nc1nccnc1C(=O)NCc1nc2ccccc2cc1-c1ccccc1CN1CCOCC1] | 3-amino-N-({3-[2-(morpholin-4-ylmethyl)phenyl]quinolin-2-yl}methyl)pyrazine-2-carboxamide |
| 71 | 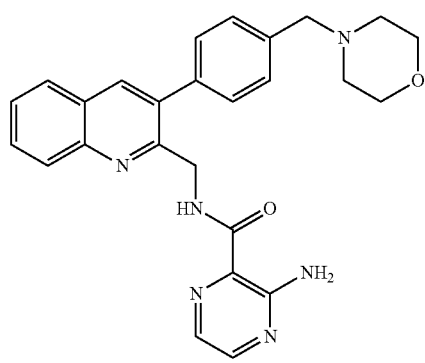 [SMILES: Nc1nccnc1C(=O)NCc1nc2ccccc2cc1-c1ccc(CN2CCOCC2)cc1] | 3-amino-N-({3-[4-(morpholin-4-ylmethyl)phenyl]quinolin-2-yl}methyl)pyrazine-2-carboxamide |

TABLE 1-continued

| Compound | Structure | Name |
|---|---|---|
| 72 | 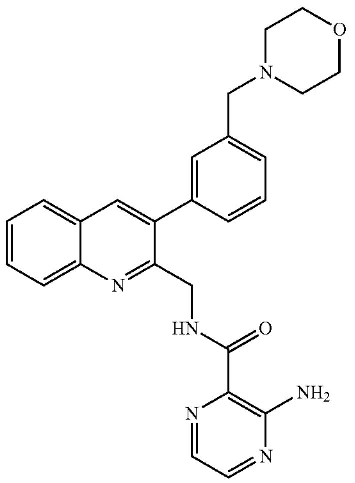 [SMILES: Nc1nccnc1C(=O)NCc1nc2ccccc2cc1-c1cccc(CN2CCOCC2)c1] | 3-amino-N-({3-[3-(morpholin-4-ylmethyl)phenyl]quinolin-2-yl}methyl)pyrazine-2-carboxamide |
| 73 | 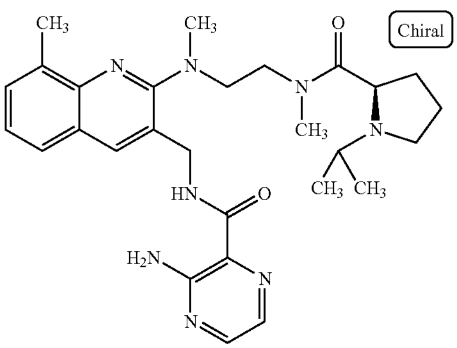 [SMILES: Cc1cccc2cc(CNC(=O)c3nccnc3N)c(N(C)CCN(C)C(=O)[C@H]3CCCN3C(C)C)nc12] | 3-amino-N-({8-methyl-2-[methyl(2-{methyl[1-(1-methylethyl)-D-prolyl]amino}ethyl)amino]quinolin-3-yl}methyl)pyrazine-2-carboxamide |
| 74 | 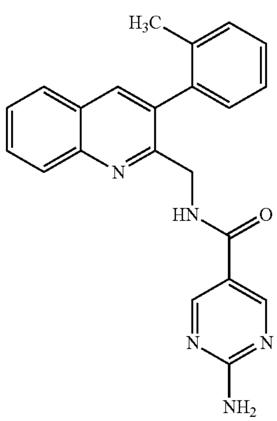 [SMILES: Cc1ccccc1-c1cc2ccccc2nc1CNC(=O)c1cnc(N)nc1] | 2-amino-N-{[3-(2-methylphenyl)quinolin-2-yl]methyl}pyrimidine-5-carboxamide |
| 75 | 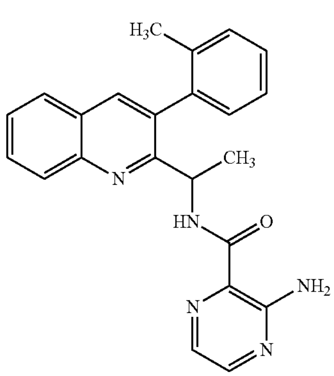 [SMILES: Cc1ccccc1-c1cc2ccccc2nc1C(C)NC(=O)c1nccnc1N] | 3-amino-N-{1-[3-(2-methylphenyl)quinolin-2-yl]ethyl}pyrazine-2-carboxamide |

| Compound | Structure | Name |
|---|---|---|
| 76 | 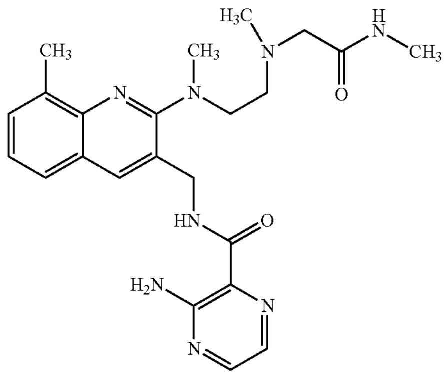 [SMILES: CNC(=O)CN(C)CCN(C)c1nc2c(C)cccc2cc1CNC(=O)c1nccnc1N] | 3-amino-N-({8-methyl-2-[methyl(2-{methyl[2-(methylamino)-2-oxoethyl]amino}ethyl)amino]quinolin-3-yl}methyl)pyrazine-2-carboxamide |
| 77 | 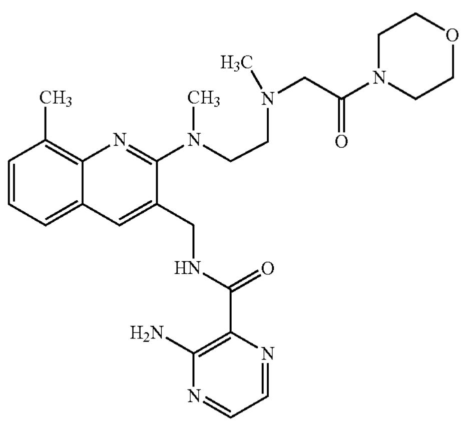 [SMILES: Cc1cccc2cc(CNC(=O)c3nccnc3N)c(N(C)CCN(C)CC(=O)N3CCOCC3)nc12] | 3-amino-N-{[8-methyl-2-(methyl{2-[methyl(2-morpholin-4-yl-2-oxoethyl)amino]ethyl}amino)quinolin-3-yl]methyl}pyrazine-2-carboxamide |
| 78 | 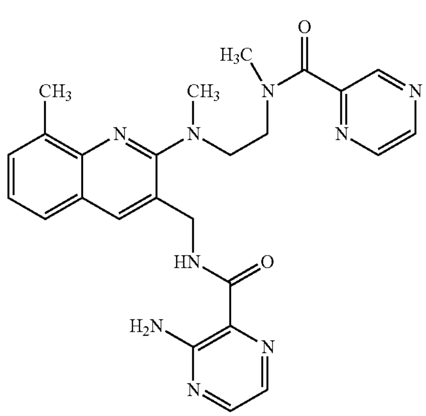 [SMILES: Cc1cccc2cc(CNC(=O)c3nccnc3N)c(N(C)CCN(C)C(=O)c3cnccn3)nc12] | 3-amino-N-{[8-methyl-2-(methyl{2-[methyl(pyrazin-2-ylcarbonyl)amino]ethyl}amino)quinolin-3-yl]methyl}pyrazine-2-carboxamide |

TABLE 1-continued

| Compound | Structure | Name |
|---|---|---|
| 79 | 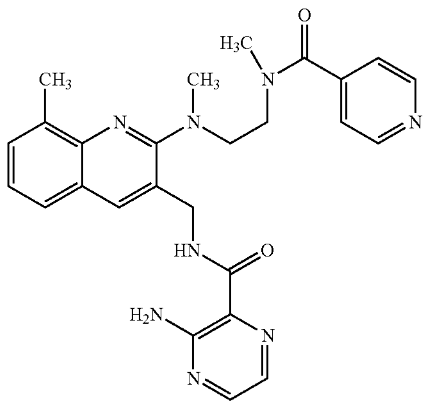 [SMILES: Cc1cccc2cc(CNC(=O)c3nccnc3N)c(N(C)CCN(C)C(=O)c3ccncc3)nc12] | 3-amino-N-{[8-methyl-2-(methyl{2-[methyl(pyridin-4-ylcarbonyl)amino]ethyl}amino)quinolin-3-yl]methyl}pyrazine-2-carboxamide |
| 80 | 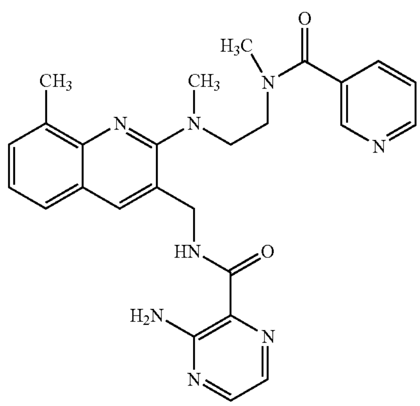 [SMILES: Cc1cccc2cc(CNC(=O)c3nccnc3N)c(N(C)CCN(C)C(=O)c3cccnc3)nc12] | 3-amino-N-{[8-methyl-2-(methyl{2-[methyl(pyridin-3-ylcarbonyl)amino]ethyl}amino)quinolin-3-yl]methyl}pyrazine-2-carboxamide |
| 81 | 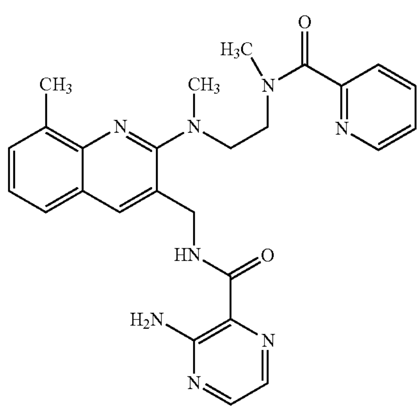 [SMILES: Cc1cccc2cc(CNC(=O)c3nccnc3N)c(N(C)CCN(C)C(=O)c3ccccn3)nc12] | 3-amino-N-{[8-methyl-2-(methyl{2-[methyl(pyridin-2-ylcarbonyl)amino]ethyl}amino)quinolin-3-yl]methyl}pyrazine-2-carboxamide |
| 82 | 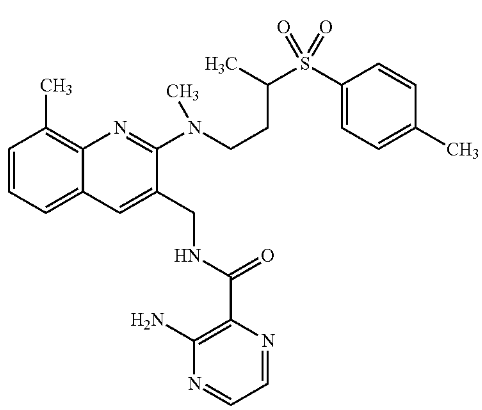 [SMILES: Cc1ccc(S(=O)(=O)C(C)CCN(C)c2nc3c(C)cccc3cc2CNC(=O)c2nccnc2N)cc1] | 3-amino-N-({8-methyl-2-[methyl(2-{methyl[(4-methylphenyl)sulfonyl]amino}ethyl)amino]quinolin-3-yl}methyl)pyrazine-2-carboxamide |

TABLE 1-continued

| Compound | Structure | Name |
|---|---|---|
| 83 | 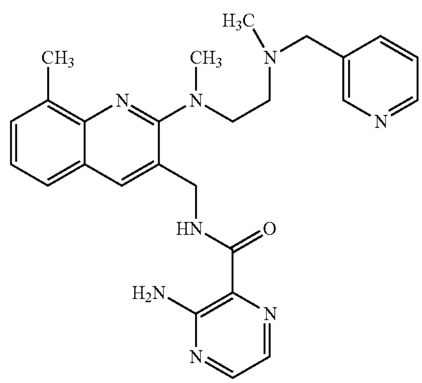 [SMILES: Cc1cccc2cc(CNC(=O)c3nccnc3N)c(N(C)CCN(C)Cc3cccnc3)nc12] | 3-amino-N-{[8-methyl-2-(methyl{2-[methyl(pyridin-3-ylmethyl)amino]ethyl}amino)quinolin-3-yl]methyl}pyrazine-2-carboxamide |
| 84 | 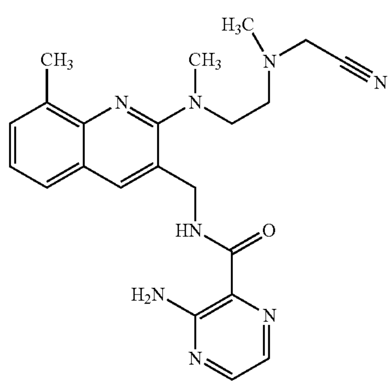 [SMILES: Cc1cccc2cc(CNC(=O)c3nccnc3N)c(N(C)CCN(C)CC#N)nc12] | 3-amino-N-({2-[{2-[(cyanomethyl)(methyl)amino]ethyl}(methyl)amino]-8-methylquinolin-3-yl}methyl)pyrazine-2-carboxamide |
| 85 | 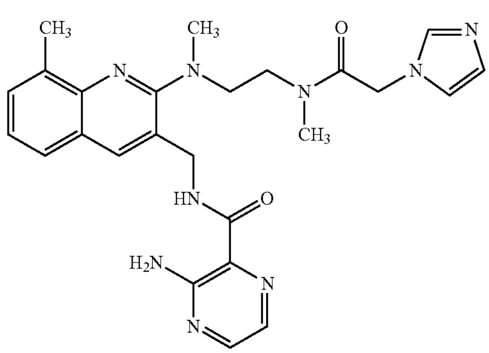 | 3-amino-N-({2-[{2-[(1H-imidazol-1-ylacetyl)(methyl)amino]ethyl}(methyl)amino]-8-methylquinolin-3-yl}methyl)pyrazine-2-carboxamide |
| 86 | 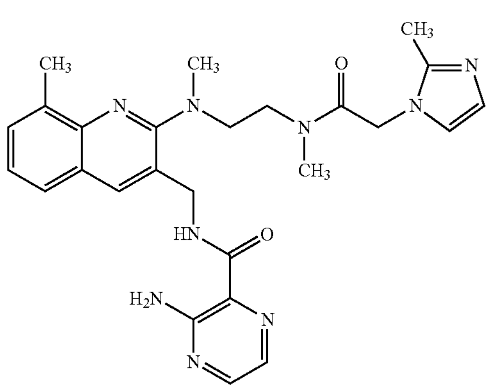 [SMILES: Cc1cccc2cc(CNC(=O)c3nccnc3N)c(N(C)CCN(C)C(=O)Cn3ccnc3C)nc12] | 3-amino-N-({8-methyl-2-[methyl(2-{methyl[(2-methyl-1H-imidazol-1-yl)acetyl]amino}ethyl)amino]quinolin-3-yl}methyl)pyrazine-2-carboxamide |

TABLE 1-continued

| Compound | Structure | Name |
|---|---|---|
| 87 | 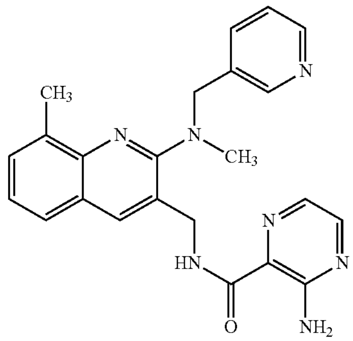 [SMILES: Cc1cccc2cc(CNC(=O)c3nccnc3N)c(N(C)Cc3cccnc3)nc12] | 3-amino-N-({8-methyl-2-[methyl(pyridin-3-ylmethyl)amino]quinolin-3-yl}methyl)pyrazine-2-carboxamide |
| 88 | 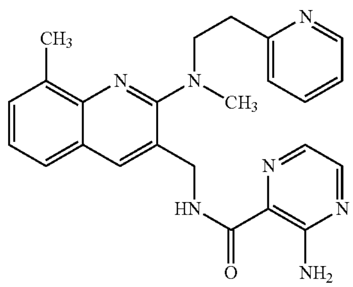 [SMILES: Cc1cccc2cc(CNC(=O)c3nccnc3N)c(N(C)CCc3ccccn3)nc12] | 3-amino-N-({8-methyl-2-[methyl(2-pyridin-2-ylethyl)amino]quinolin-3-yl}methyl)pyrazine-2-carboxamide |
| 89 | 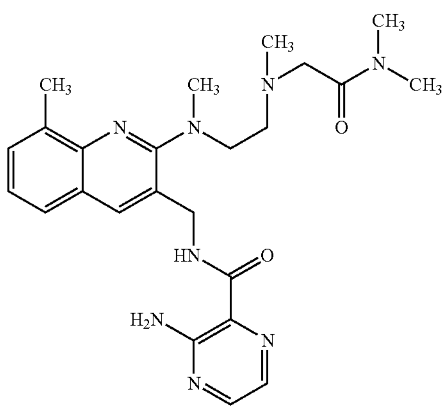 [SMILES: Cc1cccc2cc(CNC(=O)c3nccnc3N)c(N(C)CCN(C)CC(=O)N(C)C)nc12] | 3-amino-N-({2-[(2-{[2-(dimethylamino)-2-oxoethyl](methyl)amino}ethyl)(methyl)amino]-8-methylquinolin-3-yl}methyl)pyrazine-2-carboxamide |
| 90 | 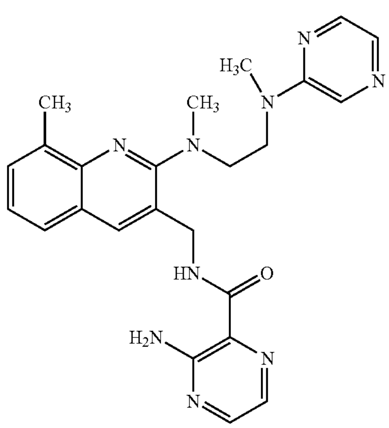 [SMILES: Cc1cccc2cc(CNC(=O)c3nccnc3N)c(N(C)CCN(C)c3cnccn3)nc12] | 3-amino-N-{[8-methyl-2-(methyl{2-[methyl(pyrazin-2-yl)amino]ethyl}amino)quinolin-3-yl]methyl}pyrazine-2-carboxamide |

TABLE 1-continued

| Compound | Structure | Name |
|---|---|---|
| 91 | 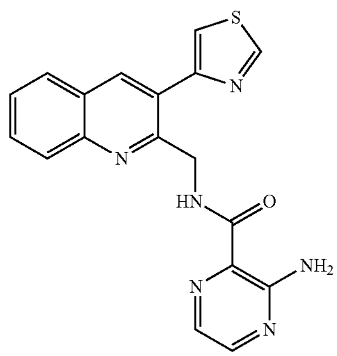 [SMILES: Nc1nccnc1C(=O)NCc1nc2ccccc2cc1-c1cscn1] | 3-amino-N-{[3-(1,3-thiazol-4-yl)quinolin-2-yl]methyl}pyrazine-2-carboxamide |
| 92 | 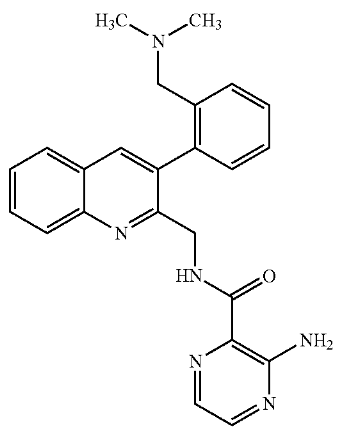 [SMILES: CN(C)Cc1ccccc1-c1cc2ccccc2nc1CNC(=O)c1nccnc1N] | 3-amino-N-[(3-{2-[(dimethylamino)methyl]phenyl}quinolin-2-yl)methyl]pyrazine-2-carboxamide |
| 93 | 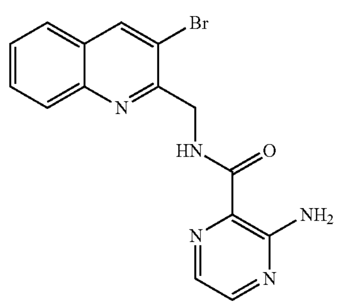 [SMILES: Nc1nccnc1C(=O)NCc1nc2ccccc2cc1Br] | 3-amino-N-[(3-bromoquinolin-2-yl)methyl]pyrazine-2-carboxamide |
| 94 | 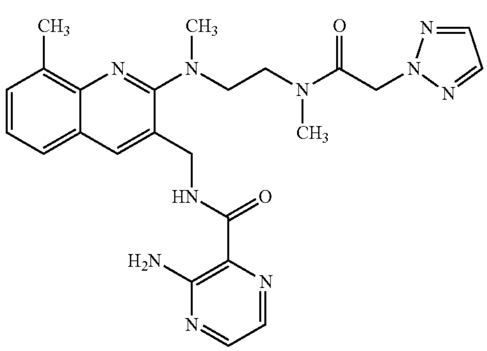 [SMILES: Cc1cccc2cc(CNC(=O)c3nccnc3N)c(N(C)CCN(C)C(=O)Cn3nccn3)nc12] | 3-amino-N-{[8-methyl-2-(methyl{2-[methyl(2H-1,2,3-triazol-2-ylacetyl)amino]ethyl}amino)quinolin-3-yl]methyl}pyrazine-2-carboxamide |

TABLE 1-continued

| Compound | Structure | Name |
|---|---|---|
| 95 | 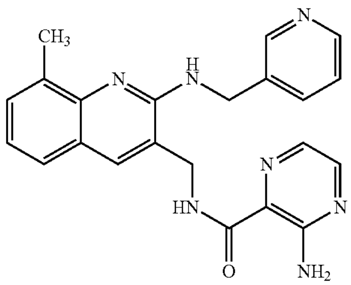 [SMILES: Cc1cccc2cc(CNC(=O)c3nccnc3N)c(NCc3cccnc3)nc12] | 3-amino-N-({8-methyl-2-[(pyridin-3-ylmethyl)amino]quinolin-3-yl}methyl)pyrazine-2-carboxamide |
| 96 | 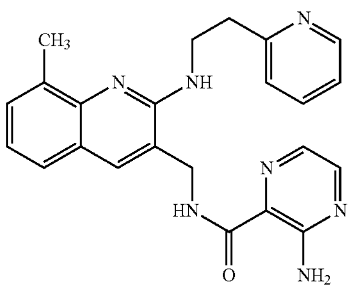 [SMILES: Cc1cccc2cc(CNC(=O)c3nccnc3N)c(NCCc3ccccn3)nc12] | 3-amino-N-({8-methyl-2-[(2-pyridin-2-ylethyl)amino]quinolin-3-yl}methyl)pyrazine-2-carboxamide |
| 97 | 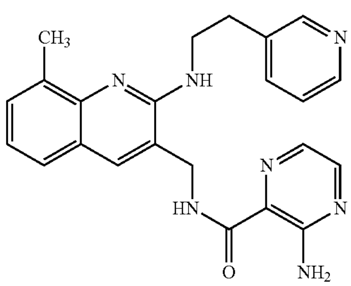 [SMILES: Cc1cccc2cc(CNC(=O)c3nccnc3N)c(NCCc3cccnc3)nc12] | 3-amino-N-({8-methyl-2-[(2-pyridin-3-ylethyl)amino]quinolin-3-yl}methyl)pyrazine-2-carboxamide |
| 98 | 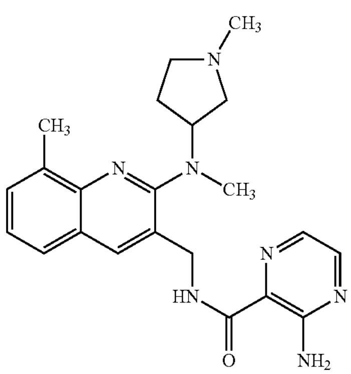 [SMILES: Cc1cccc2cc(CNC(=O)c3nccnc3N)c(N(C)C3CCN(C)C3)nc12] | 3-amino-N-({8-methyl-2-[methyl(1-methylpyrrolidin-3-yl)amino]quinolin-3-yl}methyl)pyrazine-2-carboxamide |
| 99 | 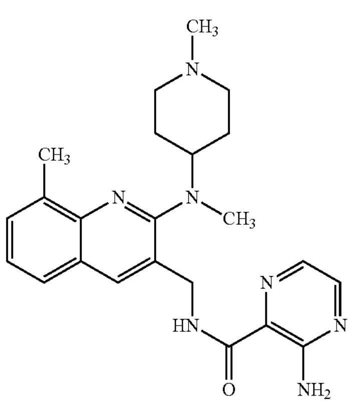 [SMILES: Cc1cccc2cc(CNC(=O)c3nccnc3N)c(N(C)C3CCN(C)CC3)nc12] | 3-amino-N-({8-methyl-2-[methyl(1-methylpiperidin-4-yl)amino]quinolin-3-yl}methyl)pyrazine-2-carboxamide |

TABLE 1-continued

| Compound | Structure | Name |
|---|---|---|
| 100 | 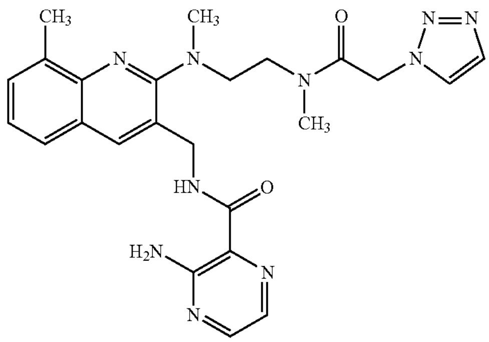 [SMILES: Cc1cccc2cc(CNC(=O)c3nccnc3N)c(N(C)CCN(C)C(=O)Cn3ccnn3)nc12] | 3-amino-N-{[8-methyl-2-(methyl{2-[methyl(1H-1,2,3-triazol-1-ylacetyl)amino]ethyl}amino)quinolin-3-yl]methyl}pyrazine-2-carboxamide |
| 101 | 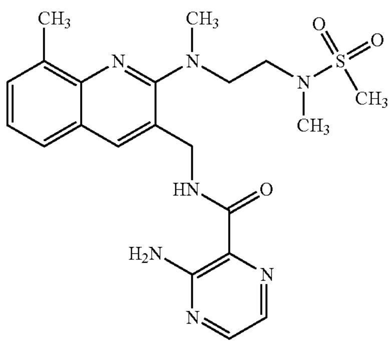 [SMILES: Cc1cccc2cc(CNC(=O)c3nccnc3N)c(N(C)CCN(C)S(C)(=O)=O)nc12] | 3-amino-N-{[8-methyl-2-(methyl{2-[methyl(methylsulfonyl)amino]ethyl}amino)quinolin-3-yl]methyl}pyrazine-2-carboxamide |
| 102 | 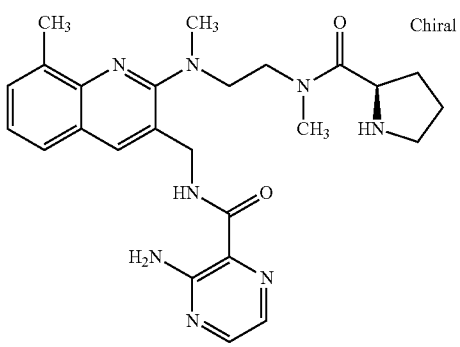 [SMILES: Cc1cccc2cc(CNC(=O)c3nccnc3N)c(N(C)CCN(C)C(=O)[C@H]3CCCN3)nc12] | 3-amino-N-{[8-methyl-2-(methyl{2-[methyl(D-prolyl)amino]ethyl}amino)quinolin-3-yl]methyl}pyrazine-2-carboxamide |
| 103 | 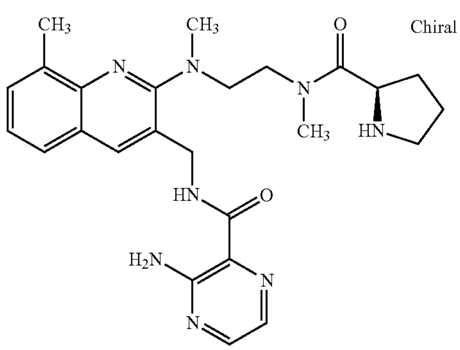 [SMILES: Cc1cccc2cc(CNC(=O)c3nccnc3N)c(N(C)CCN(C)C(=O)[C@H]3CCCN3)nc12] | 3-amino-N-{[8-methyl-2-(methyl{2-[methyl(L-prolyl)amino]ethyl}amino)quinolin-3-yl]methyl}pyrazine-2-carboxamide |

TABLE 1-continued
| Compound | Structure | Name |
|---|---|---|
| 104 | 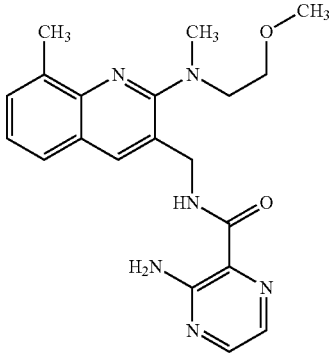 [SMILES: COCCN(C)c1nc2c(C)cccc2cc1CNC(=O)c1nccnc1N] | 3-amino-N-[(8-methyl-2-{methyl[2-(methyloxy)ethyl]amino}quinolin-3-yl)methyl]pyrazine-2-carboxamide |
| 105 | 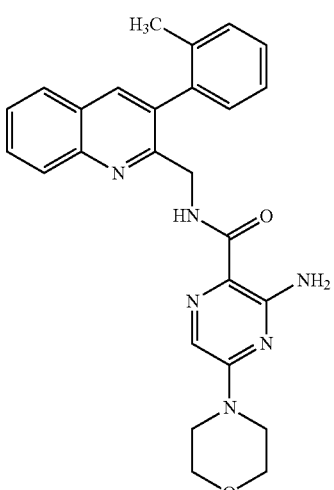 | 3-amino-N-{[3-(2-methylphenyl)quinolin-2-yl]methyl}-5-morpholin-4-ylpyrazine-2-carboxamide |
| 106 | 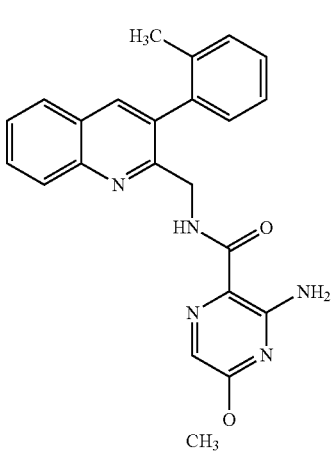 | 3-amino-5-(methyloxy)-N-{[3-(2-methylphenyl)quinolin-2-yl]methyl}pyrazine-2-carboxamide |

TABLE 1-continued

| Compound | Structure | Name |
|---|---|---|
| 107 | 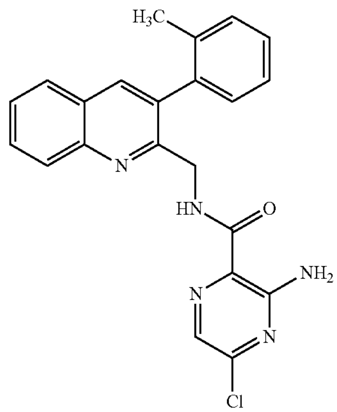 [SMILES: Cc1ccccc1-c1cc2ccccc2nc1CNC(=O)c1ncc(Cl)nc1N] | 3-amino-5-chloro-N-{[3-(2-methylphenyl)quinolin-2-yl]methyl}pyrazine-2-carboxamide |
| 108 | 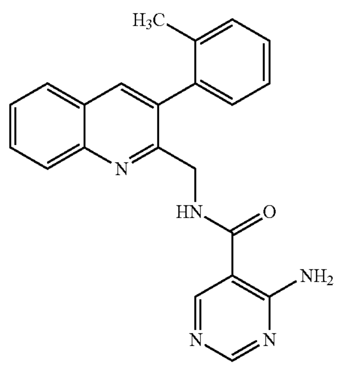 [SMILES: Cc1ccccc1-c1cc2ccccc2nc1CNC(=O)c1cncnc1N] | 4-amino-N-{[3-(2-methylphenyl)quinolin-2-yl]methyl}pyrimidine-5-carboxamide |
| 109 | 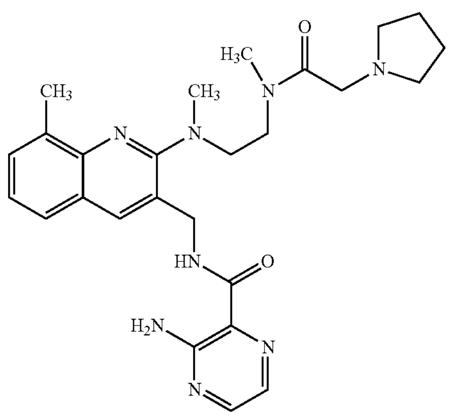 [SMILES: Cc1cccc2cc(CNC(=O)c3nccnc3N)c(N(C)CCN(C)C(=O)CN3CCCC3)nc12] | 3-amino-N-{[8-methyl-2-(methyl{2-[methyl(pyrrolidin-1-ylacetyl)amino]ethyl}amino)quinolin-3-yl]methyl}pyrazine-2-carboxamide |
| 110 | 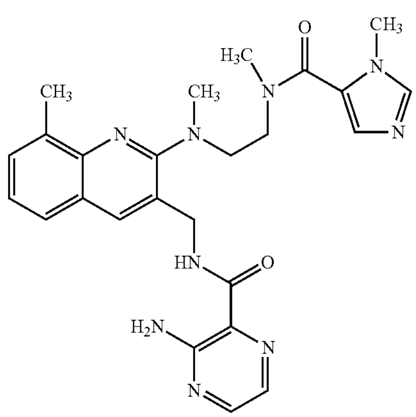 [SMILES: Cc1cccc2cc(CNC(=O)c3nccnc3N)c(N(C)CCN(C)C(=O)c3cncn3C)nc12] | 3-amino-N-({8-methyl-2-[methyl(2-{methyl[(1-methyl-1H-imidazol-5-yl)carbonyl]amino}ethyl)amino]quinolin-3-yl}methyl)pyrazine-2-carboxamide |

TABLE 1-continued

| Compound | Structure | Name |
|---|---|---|
| 111 | 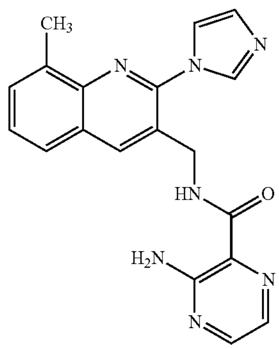 [SMILES: Cc1cccc2cc(CNC(=O)c3nccnc3N)c(-n3ccnc3)nc12] | 3-amino-N-{[2-(1H-imidazol-1-yl)-8-methylquinolin-3-yl]methyl}pyrazine-2-carboxamide |
| 112 | 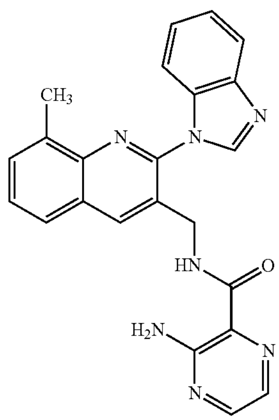 [SMILES: Cc1cccc2cc(CNC(=O)c3nccnc3N)c(-n3cnc4ccccc43)nc12] | 3-amino-N-{[2-(1H-benzimidazol-1-yl)-8-methylquinolin-3-yl]methyl}pyrazine-2-carboxamide |
| 113 | 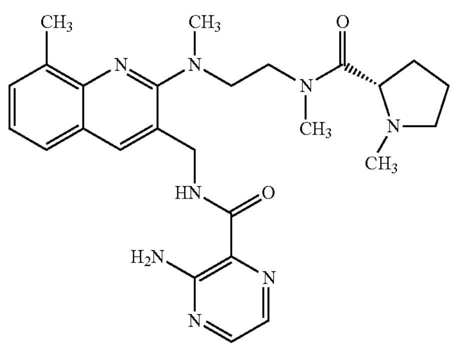 [SMILES: Cc1cccc2cc(CNC(=O)c3nccnc3N)c(N(C)CCN(C)C(=O)[C@@H]3CCCN3C)nc12] | 3-amino-N-{[8-methyl-2-(methyl{2-[methyl(1-methyl-L-prolyl)amino]ethyl}amino)quinolin-3-yl]methyl}pyrazine-2-carboxamide |
| 114 | 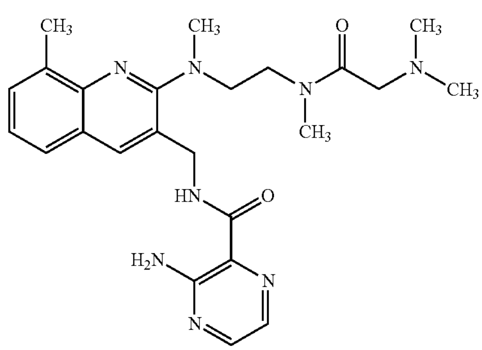 [SMILES: Cc1cccc2cc(CNC(=O)c3nccnc3N)c(N(C)CCN(C)C(=O)CN(C)C)nc12] | 3-amino-N-({2-[{2-[(N,N-dimethylglycyl)(methyl)amino]ethyl}(methyl)amino]-8-methylquinolin-3-yl}methyl)pyrazine-2-carboxamide |

TABLE 1-continued

| Compound | Structure | Name |
|---|---|---|
| 115 | 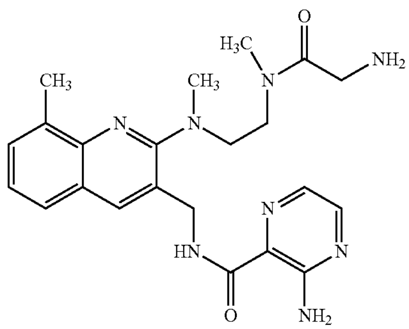 [SMILES: Cc1cccc2cc(CNC(=O)c3nccnc3N)c(N(C)CCN(C)C(=O)CN)nc12] | 3-amino-N-({2-[{2-[glycyl(methyl)amino]ethyl}(methyl)amino]-8-methylquinolin-3-yl}methyl)pyrazine-2-carboxamide |
| 116 | 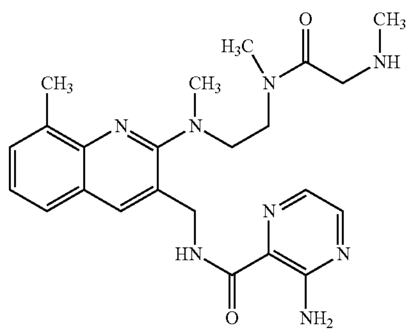 [SMILES: CNCC(=O)N(C)CCN(C)c1nc2c(C)cccc2cc1CNC(=O)c1nccnc1N] | 3-amino-N-{[8-methyl-2-(methyl{2-[methyl(N-methylglycyl)amino]ethyl}amino)quinolin-3-yl]methyl}pyrazine-2-carboxamide |
| 117 | 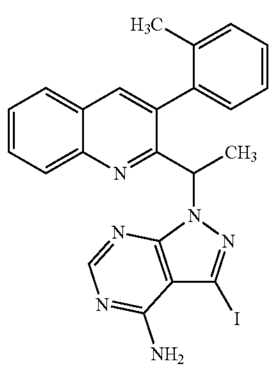 [SMILES: Cc1ccccc1-c1cc2ccccc2nc1C(C)n1nc(I)c2c(N)ncnc21] | 3-iodo-1-{1-[3-(2-methylphenyl)quinolin-2-yl]ethyl}-1H-pyrazolo[3,4-d]pyrimidin-4-amine |
| 118 | 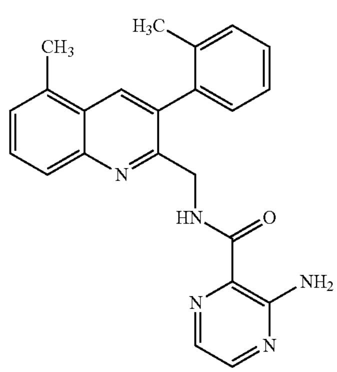 [SMILES: Cc1ccccc1-c1cc2c(C)cccc2nc1CNC(=O)c1nccnc1N] | 3-amino-N-{[5-methyl-3-(2-methylphenyl)quinolin-2-yl]methyl}pyrazine-2-carboxamide |

TABLE 1-continued

| Compound | Structure | Name |
|---|---|---|
| 119 | 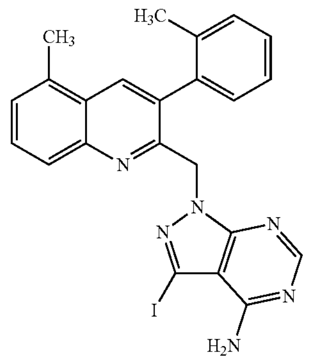 [SMILES: Cc1ccccc1-c1cc2c(C)cccc2nc1Cn1nc(I)c2c(N)ncnc21] | 3-iodo-1-{[5-methyl-3-(2-methylphenyl)quinolin-2-yl]methyl}-1H-pyrazolo[3,4-d]pyrimidin-4-amine |
| 120 | 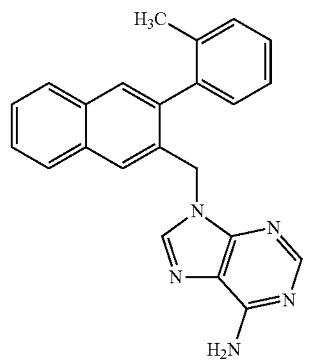 [SMILES: Cc1ccccc1-c1cc2ccccc2cc1Cn1cnc2c(N)ncnc21] | 9-{[3-(2-methylphenyl)naphthalen-2-yl]methyl}-9H-purin-6-amine |
| 121 | 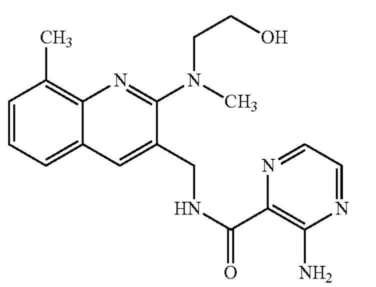 [SMILES: Cc1cccc2cc(CNC(=O)c3nccnc3N)c(N(C)CCO)nc12] | 3-amino-N-({2-[(2-hydroxyethyl)(methyl)amino]-8-methylquinolin-3-yl}methyl)pyrazine-2-carboxamide |
| 122 | 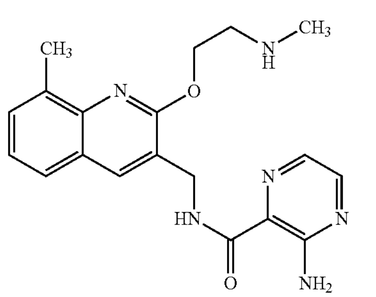 [SMILES: CNCCOc1nc2c(C)cccc2cc1CNC(=O)c1nccnc1N] | 3-amino-N-[(8-methyl-2-{[2-(methylamino)ethyl]oxy}quinolin-3-yl)methyl]pyrazine-2-carboxamide |

TABLE 1-continued

| Compound | Structure | Name |
|---|---|---|
| 123 | 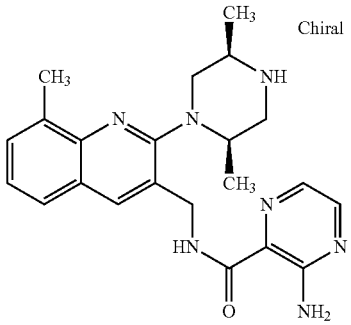 [SMILES: Cc1cccc2cc(CNC(=O)c3nccnc3N)c(N3C[C@@H](C)NC[C@H]3C)nc12] | 3-amino-N-({2-[(2R,5S)-2,5-dimethylpiperazin-1-yl]-8-methylquinolin-3-yl}methyl)pyrazine-2-carboxamide |
| 124 | 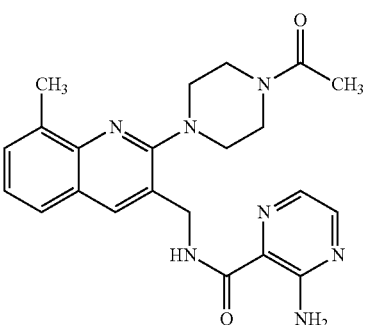 | N-{[2-(4-acetylpiperazin-1-yl)-8-methylquinolin-3-yl]methyl}-3-aminopyrazine-2-carboxamide |
| 125 | 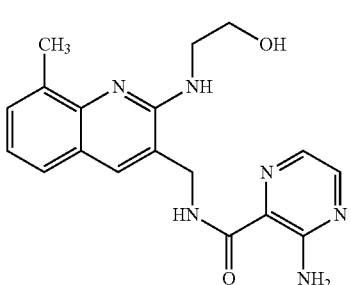 | 3-amino-N-({2-[(2-hydroxyethyl)amino]-8-methylquinoin-3-yl}methyl)pyrazine-2-carboxamide |
| 126 | 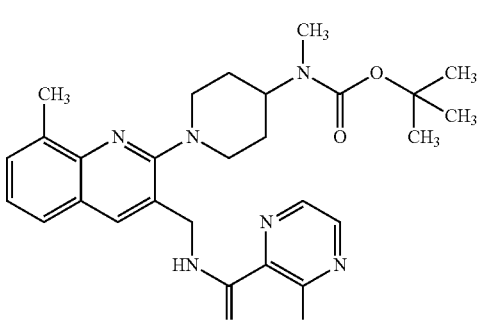 | 1,1-dimethylethyl {1-[3-({[(3-aminopyrazin-2-yl)carbonyl]amino}methyl)-8-methylquinolin-2-yl]piperidin-4-yl}methylcarbamate |
| 127 | 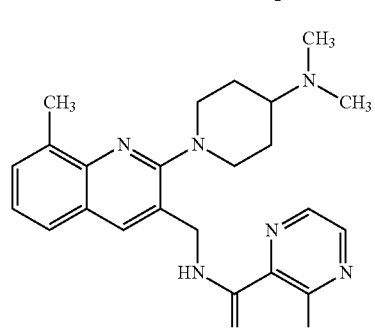 | 3-amino-N-({2-[4-(dimethylamino)piperidin-1-yl]-8-methylquinolin-3-yl}methyl)pyrazine-2-carboxamide |

TABLE 1-continued

| Compound | Structure | Name |
|---|---|---|
| 128 | 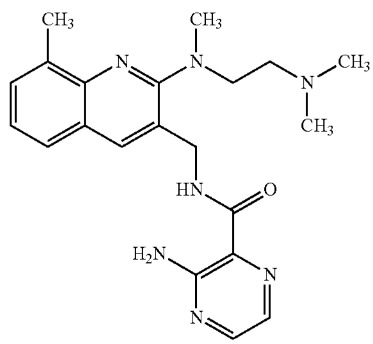 [SMILES: Cc1cccc2cc(CNC(=O)c3nccnc3N)c(N(C)CCN(C)C)nc12] | 3-amino-N-[(2-{[2-(dimethylamino)ethyl](methyl)amino}-8-methylquinolin-3-yl)methyl]pyrazine-2-carboxamide |
| 129 | 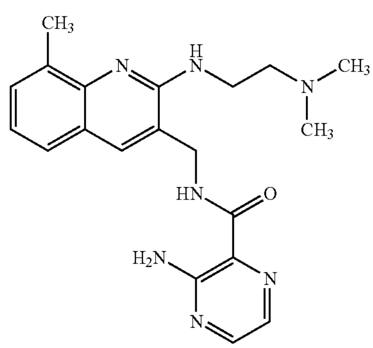 [SMILES: Cc1cccc2cc(CNC(=O)c3nccnc3N)c(NCCN(C)C)nc12] | 3-amino-N-[(2-{[2-(dimethylamino)ethyl]amino}-8-methylquinolin-3-yl)methyl]pyrazine-2-carboxamide |
| 130 | 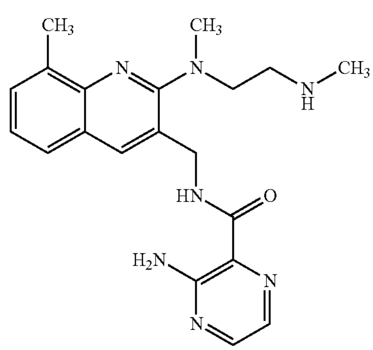 [SMILES: CNCCN(C)c1nc2c(C)cccc2cc1CNC(=O)c1nccnc1N] | 3-amino-N-[(8-methyl-2-{methyl[2-(methylamino)ethyl]amino}quinolin-3-yl)methyl]pyrazine-2-carboxamide |
| 131 | 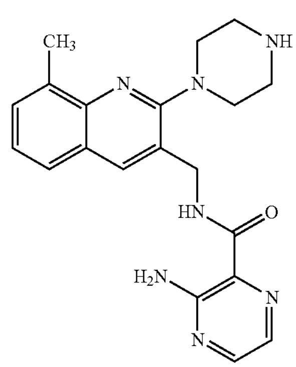 [SMILES: Cc1cccc2cc(CNC(=O)c3nccnc3N)c(N3CCNCC3)nc12] | 3-amino-N-[(8-methyl-2-piperazin-1-ylquinolin-3-yl)methyl]pyrazine-2-carboxamide |

TABLE 1-continued

| Compound | Structure | Name |
|---|---|---|
| 132 | 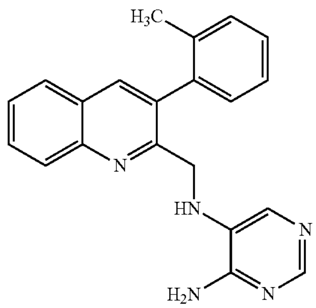 [SMILES: Cc1ccccc1-c1cc2ccccc2nc1CNc1cncnc1N] | N-5-{[3-(2-methylphenyl)quinolin-2-yl]methyl}pyrimidin-4,5-diamine |
| 133 | 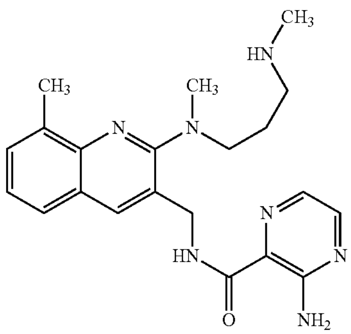 [SMILES: CNCCCN(C)c1nc2c(C)cccc2cc1CNC(=O)c1nccnc1N] | 3-amino-N-[(8-methyl-2-{methyl[3-(methylamino)propyl]amino}quinolin-3-yl)methyl]pyrazine-2-carboxamide |
| 134 | 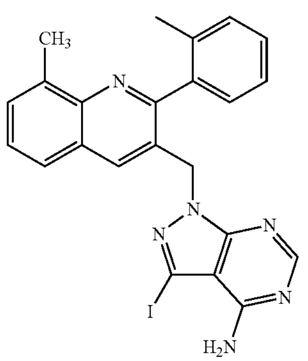 [SMILES: Cc1ccccc1-c1nc2c(C)cccc2cc1Cn1nc(I)c2c(N)ncnc21] | 3-iodo-1-{[8-methyl-2-(2-methylphenyl)quinolin-3-yl]methyl}-1H-pyrazolo[3,4-d]pyrimidin-4-amine |
| 135 | 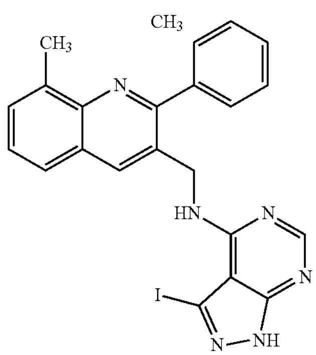 | 3-iodo-N-{[8-methyl-2-(2-methylphenyl)quinolin-3-yl]methyl}-1H-pyrazolo[3,4-d]pyrimidin-4-amine |

TABLE 1-continued

| Compound | Structure | Name |
|---|---|---|
| 136 | 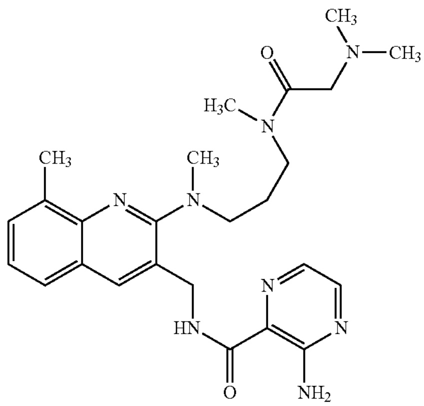 [SMILES: Cc1cccc2cc(CNC(=O)c3nccnc3N)c(N(C)CCCN(C)C(=O)CN(C)C)nc12] | 3-amino-N-({2-[{3-[(N,N-dimethylglycyl)(methyl)amino]propyl}(methyl)amino]-8-methylquinolin-3-yl}methyl)pyrazine-2-carboxamide |
| 137 | 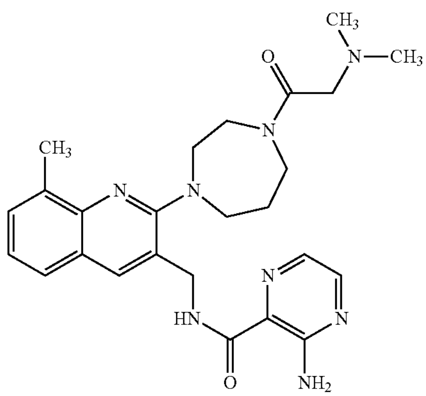 [SMILES: Cc1cccc2cc(CNC(=O)c3nccnc3N)c(N3CCCN(C(=O)CN(C)C)CC3)nc12] | 3-amino-N-({2-[4-(N,N-dimethylglycyl)-1,4-diazepan-1-yl]-8-methylquinolin-3-yl}methyl)pyrazine-2-carboxamide |
| 138 | 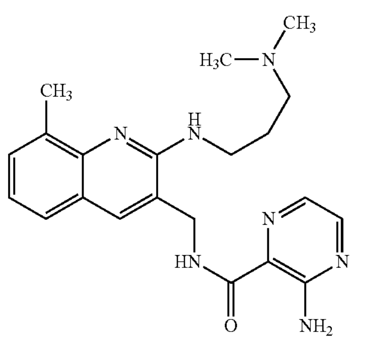 [SMILES: Cc1cccc2cc(CNC(=O)c3nccnc3N)c(NCCCN(C)C)nc12] | 3-amino-N-[(2-{[3-(dimethylamino)propyl]amino}-8-methylquinolin-3-yl)methyl]pyrazine-2-carboxamide |
| 139 | 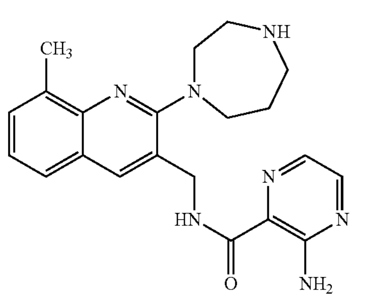 [SMILES: Cc1cccc2cc(CNC(=O)c3nccnc3N)c(N3CCCNCC3)nc12] | 3-amino-N-{[2-(1,4-diazepan-1-yl)-8-methylquinolin-3-yl]methyl}pyrazine-2-carboxamide |

TABLE 1-continued

| Compound | Structure | Name |
|---|---|---|
| 140 | 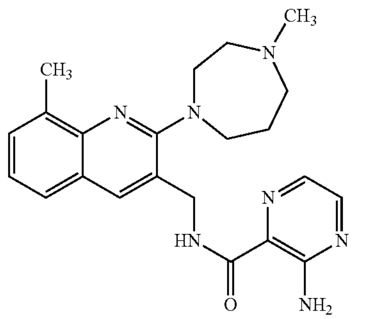 [SMILES: Cc1cccc2cc(CNC(=O)c3nccnc3N)c(N3CCCN(C)CC3)nc12] | 3-amino-N-{[8-methyl-2-(4-methyl-1,4-diazepan-1-yl)quinolin-3-yl]methyl}pyrazine-2-carboxamide |
| 141 | 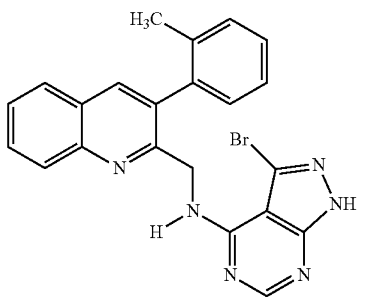 [SMILES: Cc1ccccc1-c1cc2ccccc2nc1CNc1ncnc2[nH]nc(Br)c12] | 3-bromo-N-{[3-(2-methylphenyl)quinolin-2-yl]methyl}-1H-pyrazolo[3,4-d]primidin-4-amine |
| 142 | 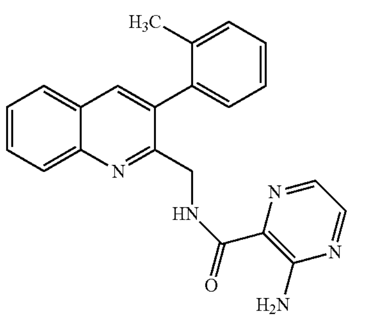 [SMILES: Cc1ccccc1-c1cc2ccccc2nc1CNC(=O)c1nccnc1N] | 3-amino-N-{[3-(2-methylphenyl)quinolin-2-yl]methyl}pyrazine-2-carboxamide |
| 143 | 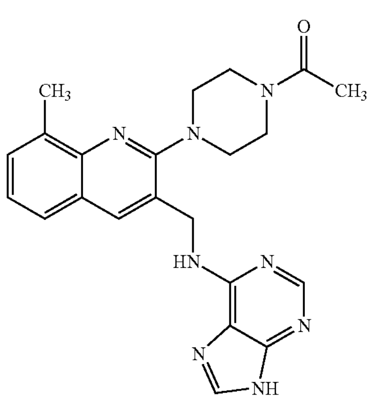 [SMILES: CC(=O)N1CCN(c2nc3c(C)cccc3cc2CNc2ncnc3[nH]cnc23)CC1] | N-{[2-(4-acetylpiperazin-1-yl)-8-methylquinolin-3-yl]methyl}-9H-purin-6-amine |

TABLE 1-continued

| Compound | Structure | Name |
|---|---|---|
| 144 | 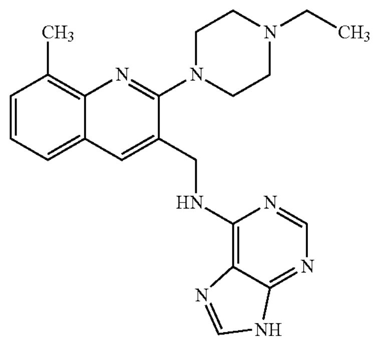 [SMILES: CCN1CCN(c2nc3c(C)cccc3cc2CNc2ncnc3[nH]cnc23)CC1] | N-{[2-(4-ethylpiperazin-1-yl)-8-methylquinolin-3-yl]methyl}-9H-purin-6-amine |
| 145 | 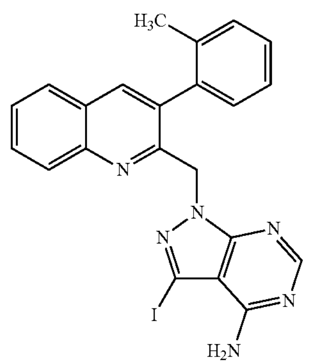 [SMILES: Cc1ccccc1-c1cc2ccccc2nc1Cn1nc(I)c2c(N)ncnc21] | 3-iodo-1-{[3-(2-methylphenyl)quinolin-2-yl]methyl}-1H-pyrazolo[3,4-d]pyrimidin-4-amine |
| 146 | 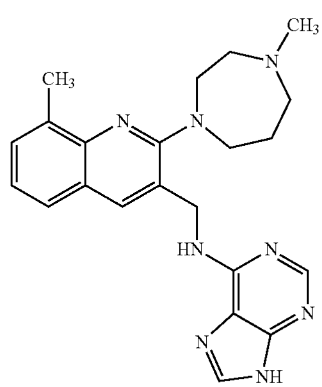 [SMILES: Cc1cccc2cc(CNc3ncnc4[nH]cnc34)c(N3CCCN(C)CC3)nc12] | N-{[8-methyl-2-(4-methyl-1,4-diazepan-1-yl)quinolin-3-yl]methyl}-9H-purin-6-amine |
| 147 | 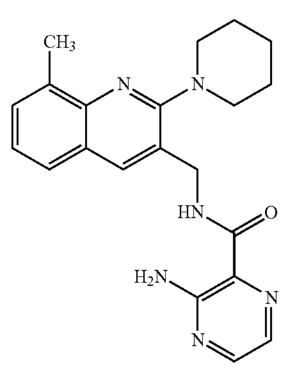 [SMILES: Cc1cccc2cc(CNC(=O)c3nccnc3N)c(N3CCCCC3)nc12] | 3-amino-N-[(8-methyl-2-piperidin-1-ylquinolin-3-yl)methyl]pyrazine-2-carboxamide |

TABLE 1-continued

| Compound | Structure | Name |
|---|---|---|
| 148 | 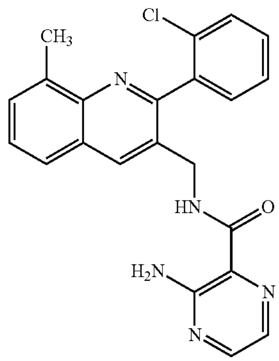 [SMILES: Cc1cccc2cc(CNC(=O)c3nccnc3N)c(-c3ccccc3Cl)nc12] | 3-amino-N-{[2-(2-chlorophenyl)-8-methylquinolin-3-yl]methyl}pyrazine-2-carboxamide |
| 149 | 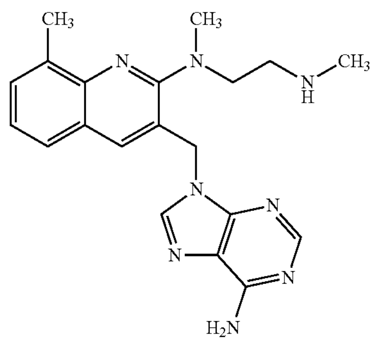 [SMILES: CNCCN(C)c1nc2c(C)cccc2cc1Cn1cnc2c(N)ncnc21] | N-{3-[(6-amino-9H-purin-9-yl)methyl]-8-methylquinolin-2-yl}-N,N'-dimethylethane-1,2-diamine |
| 150 | 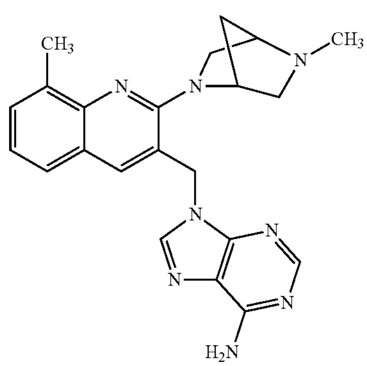 [SMILES: Cc1cccc2cc(Cn3cnc4c(N)ncnc43)c(N3CC4CC3CN4C)nc12] | 9-{[8-methyl-2-(5-methyl-2,5-diazabicyclo[2.2.1]hept-2-yl)quinolin-3-yl]methyl}-9H-purin-6-amine |
| 151 | 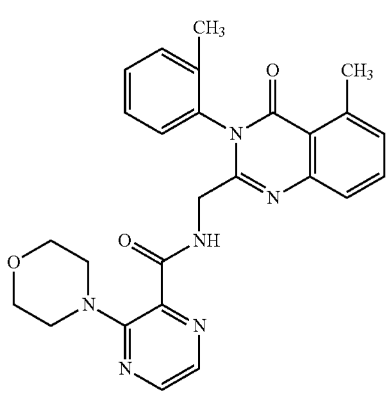 [SMILES: Cc1ccccc1-n1c(CNC(=O)c2nccnc2N2CCOCC2)nc2cccc(C)c2c1=O] | N-{[5-methyl-3-(2-methylphenyl)-4-oxo-3,4-dihydroquinolin-2-yl]methyl}-3-morpholin-4-ylpyrazine-2-carboxamide |

TABLE 1-continued

| Compound | Structure | Name |
|---|---|---|
| 152 | 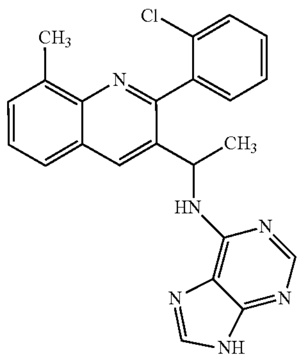 [SMILES: Cc1cccc2cc(C(C)Nc3ncnc4[nH]cnc34)c(-c3ccccc3Cl)nc12] | N-{1-[2-(2-chlorophenyl)-8-methylquinolin-3-yl]ethyl}-9H-purin-6-amine |
| 153 | 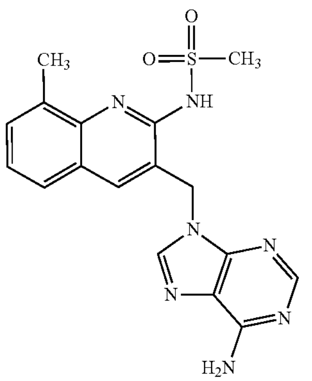 [SMILES: Cc1cccc2cc(Cn3cnc4c(N)ncnc43)c(NS(C)(=O)=O)nc12] | N-{3-[(6-amino-9H-purin-9-yl)methyl]-8-methylquinolin-2-yl}methanesulfonamide |
| 154 | 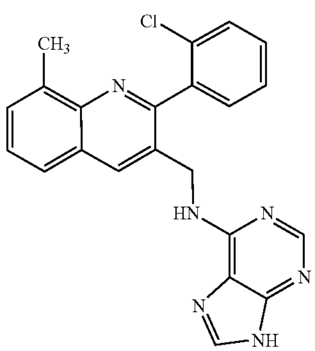 [SMILES: Cc1cccc2cc(CNc3ncnc4[nH]cnc34)c(-c3ccccc3Cl)nc12] | N-{[2-(2-chlorophenyl)-8-methylquinolin-3-yl]methyl}-9H-purin-6-amine |
| 155 | 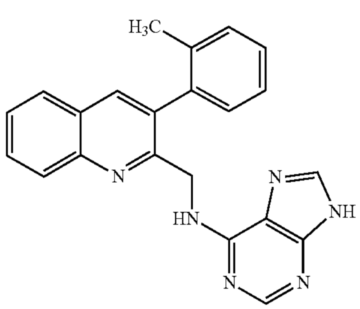 [SMILES: Cc1ccccc1-c1cc2ccccc2nc1CNc1ncnc2[nH]cnc12] | N-{[3-(2-methylphenyl)quinolin-2-yl]methyl}-9H-purin-6-amine |

TABLE 1-continued

| Compound | Structure | Name |
|---|---|---|
| 156 | 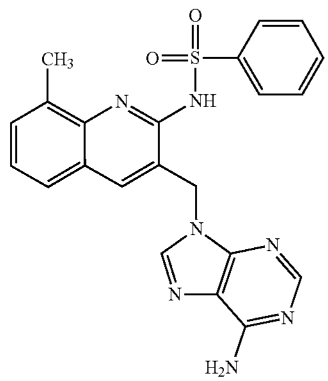 [SMILES: Cc1cccc2cc(Cn3cnc4c(N)ncnc43)c(NS(=O)(=O)c3ccccc3)nc12] | N-{3-[(6-amino-9H-purin-9-yl)methyl]-8-methylquinolin-2-yl}benzenesulfonamide |
| 157 | 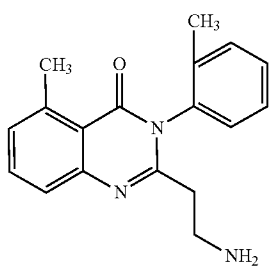 [SMILES: Cc1ccccc1-n1c(CCN)nc2cccc(C)c2c1=O] | 2-(2-aminoethyl)-5-methyl-3-(2-methylphenyl)quinazolin-4(3H)-one |
| 158 | 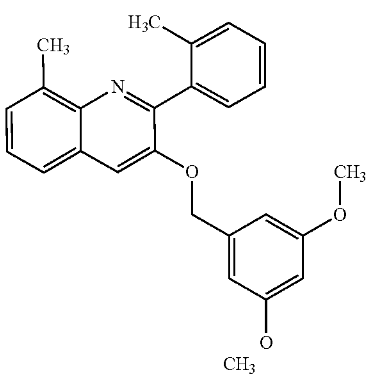 | 3-({[3,5-bis(methyloxy)phenyl]methyl}oxy)-8-methyl-2-(2-methylphenyl)quinoline |
| 159 | 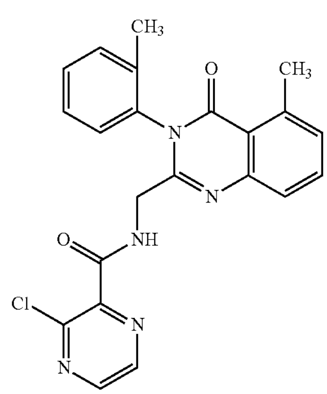 [SMILES: Cc1ccccc1-n1c(CNC(=O)c2nccnc2Cl)nc2cccc(C)c2c1=O] | 3-chloro-N-{[5-methyl-3-(2-methylphenyl)-4-oxo-3,4-dihydroquinazolin-2-yl]methyl}pyrazine-2-carboxamide |

TABLE 1-continued

| Compound | Structure | Name |
|---|---|---|
| 160 | 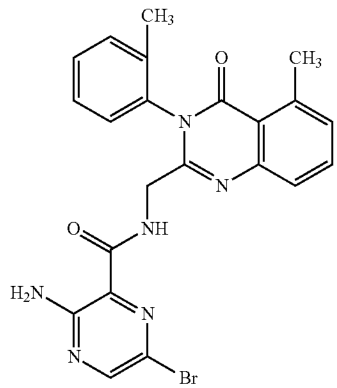 [SMILES: Cc1ccccc1-n1c(CNC(=O)c2nc(Br)cnc2N)nc2cccc(C)c2c1=O] | 3-amino-6-bromo-N-{[5-methyl-3-(2-methylphenyl)-4-oxo-3,4-dihydroquinazolin-2-yl]methyl}pyrazine-2-carboxamide |
| 161 | 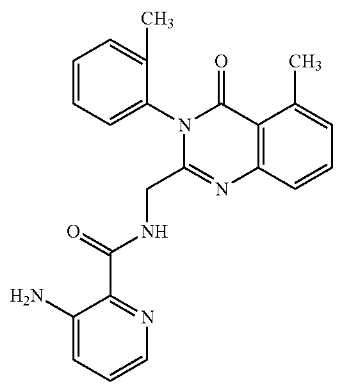 | 3-amino-N-{[5-methyl-3-(2-methylphenyl)-4-oxo-3,4-dihydroquinazolin-2-yl]methyl}pyridine-2-carboxamide |
| 162 | 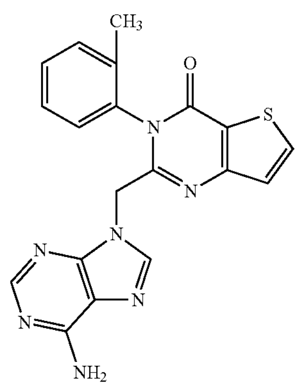 [SMILES: Cc1ccccc1-n1c(Cn2cnc3c(N)ncnc32)nc2ccsc2c1=O] | 2-[(6-amino-9H-purin-9-yl)methyl]-3-(2-methylphenyl)thieno[3,2-d]pyrimidin-4(3H)-one |
| 163 | 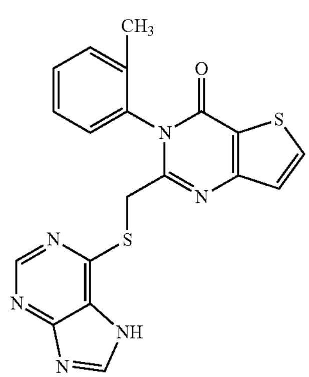 [SMILES: Cc1ccccc1-n1c(CSc2ncnc3nc[nH]c23)nc2ccsc2c1=O] | 3-(2-methylphenyl)-2-[(7H-purin-6-ylthio)methyl]thieno[3,2-d]pyrimidin-4(3H)-one |

TABLE 1-continued

| Compound | Structure | Name |
|---|---|---|
| 164 | 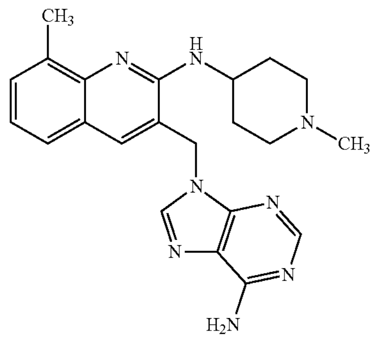 [SMILES: Cc1cccc2cc(Cn3cnc4c(N)ncnc43)c(NC3CCN(C)CC3)nc12] | 3-[(6-amino-9H-purin-9-yl)methyl]-8-methyl-N-(1-methylpiperidin-4-yl)quinolin-2-amine |
| 165 | 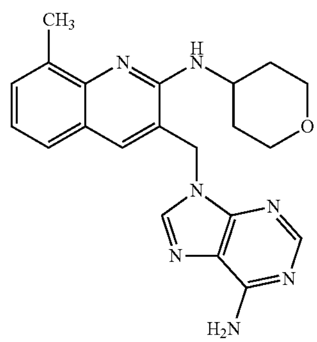 [SMILES: Cc1cccc2cc(Cn3cnc4c(N)ncnc43)c(NC3CCOCC3)nc12] | 3-[(6-amino-9H-purin-9-yl)methyl]-8-methyl-N-(tetrahydro-2H-pyran-4-yl)quinolin-2-amine |
| 166 | 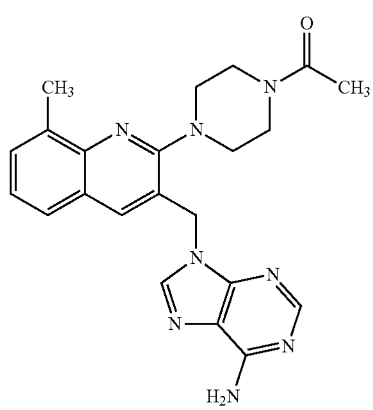 [SMILES: CC(=O)N1CCN(c2nc3c(C)cccc3cc2Cn2cnc3c(N)ncnc32)CC1] | 9-{[2-(4-acetylpiperazin-1-yl)-8-methylquinolin-3-yl]methyl}-9H-purin-6-amine |
| 167 | 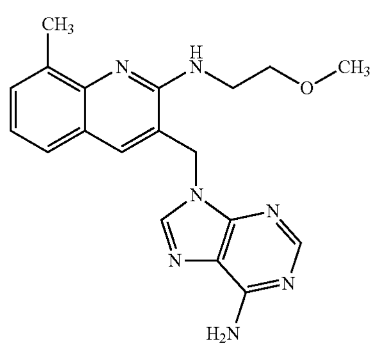 [SMILES: COCCNc1nc2c(C)cccc2cc1Cn1cnc2c(N)ncnc21] | 3-[(6-amino-9H-purin-9-yl)methyl]-8-methyl-N-[2-(methyloyx)ethyl]quinolin-2-amine |

TABLE 1-continued

| Compound | Structure | Name |
|---|---|---|
| 168 | 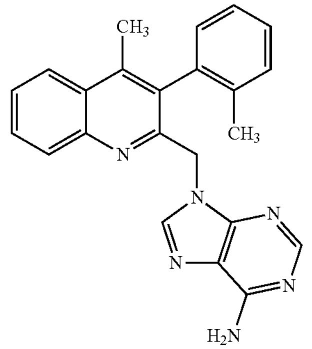 [SMILES: Cc1ccccc1-c1c(Cn2cnc3c(N)ncnc32)nc2ccccc2c1C] | 9-{[4-methyl-3-(2-methylphenyl)quinolin-2-yl]methyl}-9H-purin-6-amine |
| 169 | 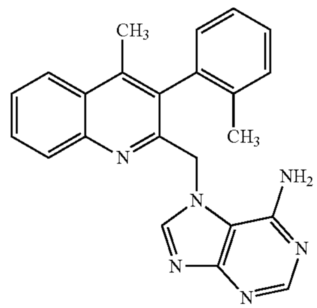 [SMILES: Cc1ccccc1-c1c(Cn2cnc3ncnc(N)c32)nc2ccccc2c1C] | 7-{[4-methyl-3-(2-methylphenyl)quinolin-2-yl]methyl}-7H-purin-6-amine |
| 170 | 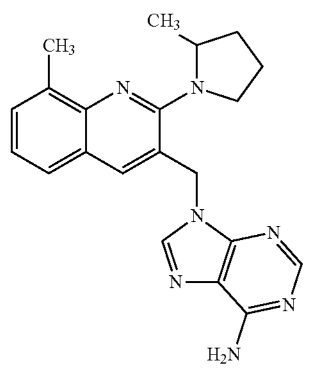 [SMILES: Cc1cccc2cc(Cn3cnc4c(N)ncnc43)c(N3CCCC3C)nc12] | 9-{[8-methyl-2-(2-methylpyrrolidin-1-yl)quinolin-3-yl]methyl}-9H-purin-6-amine |
| 171 | 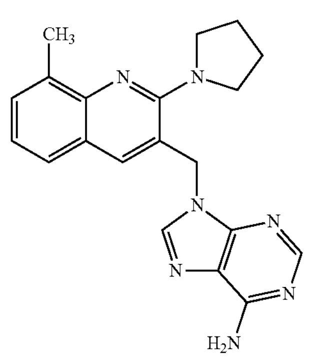 [SMILES: Cc1cccc2cc(Cn3cnc4c(N)ncnc43)c(N3CCCC3)nc12] | 9-[(8-methyl-2-pyrrolidin-1-ylquinolin-3-yl)methyl]-9H-purin-6-amine |

TABLE 1-continued

| Compound | Structure | Name |
|---|---|---|
| 172 | 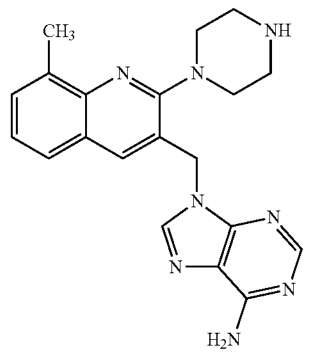 [SMILES: Cc1cccc2cc(Cn3cnc4c(N)ncnc43)c(N3CCNCC3)nc12] | 9-[(8-methyl-2-piperazin-1-ylquinolin-3-yl)methyl]-9H-purin-6-amine |
| 173 | 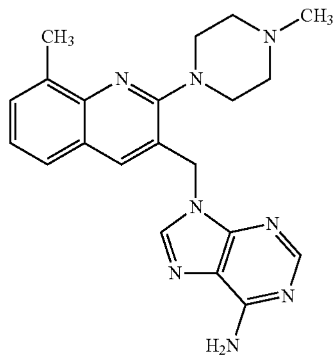 [SMILES: Cc1cccc2cc(Cn3cnc4c(N)ncnc43)c(N3CCN(C)CC3)nc12] | 9-{[8-methyl-2-(4-methylpiperazin-1-yl)quinolin-3-yl]methyl}-9H-purin-6-amine |
| 174 | 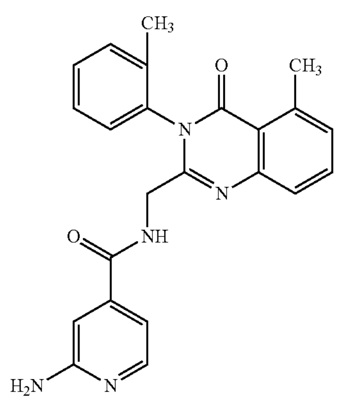 [SMILES: Cc1ccccc1-n1c(CNC(=O)c2ccnc(N)c2)nc2cccc(C)c2c1=O] | 2-amino-N-{[5-methyl-3-(2-methylphenyl)-4-oxo-3,4-dihydroquinazolin-2-yl]methyl}pyridine-4-carboxamide |
| 175 | 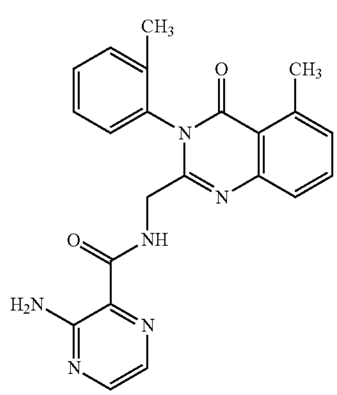 [SMILES: Cc1ccccc1-n1c(CNC(=O)c2nccnc2N)nc2cccc(C)c2c1=O] | 3-amino-N-{[5-methyl-3-(2-methylphenyl)-4-oxo-3,4-dihydroquinazolin-2-yl]methyl}pyrazine-2-carboxamide |

TABLE 1-continued

| Compound | Structure | Name |
|---|---|---|
| 176 | 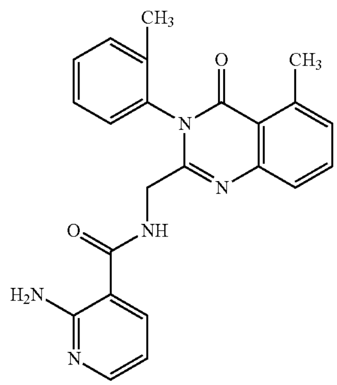 [SMILES: Cc1ccccc1-n1c(CNC(=O)c2cccnc2N)nc2cccc(C)c2c1=O] | 2-amino-N-{[5-methyl-3-(2-methylphenyl)-4-oxo-3,4-dihydroquinazolin-2-yl]methyl}pyridine-3-carboxamide |
| 177 | 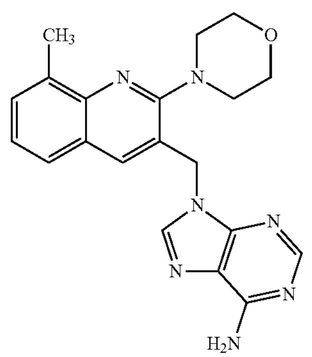 [SMILES: Cc1cccc2cc(Cn3cnc4c(N)ncnc43)c(N3CCOCC3)nc12] | 9-[(8-methyl-2-morpholin-4-ylquinolin-3-yl)methyl]-9H-purin-6-amine |
| 178 | 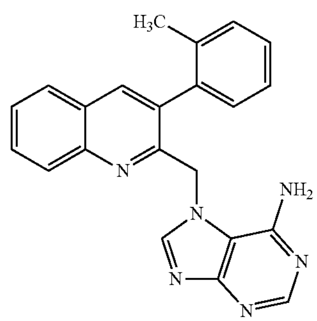 [SMILES: Cc1ccccc1-c1cc2ccccc2nc1Cn1cnc2ncnc(N)c21] | 7-{[3-(2-methylphenyl)quinolin-2-yl]methyl}-7H-purin-6-amine |
| 179 | 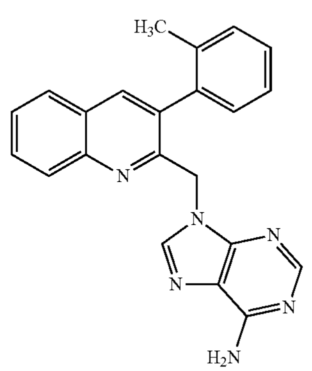 | 9-{[3-(2-methylphenyl)quinolin-2-yl]methyl}-9H-purin-6-amine |

TABLE 1-continued

| Compound | Structure | Name |
|---|---|---|
| 180 | 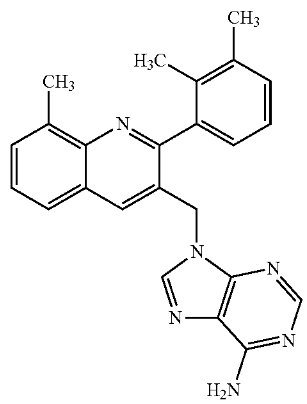 [SMILES: Cc1cccc(-c2nc3c(C)cccc3cc2Cn2cnc3c(N)ncnc32)c1C] | 9-{[2-(2,3-dimethylphenyl)-8-methylquinolin-3-yl]methyl}-9H-purin-6-amine |
| 181 | 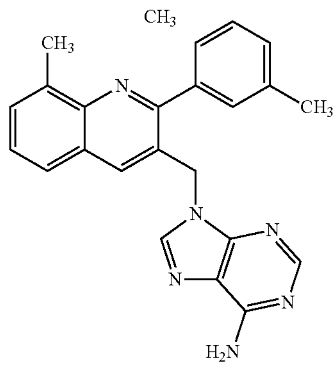 | 9-{[2-(2,5-dimethylphenyl)-8-methylquinolin-3-yl]methyl}-9H-purin-6-amine |
| 182 | 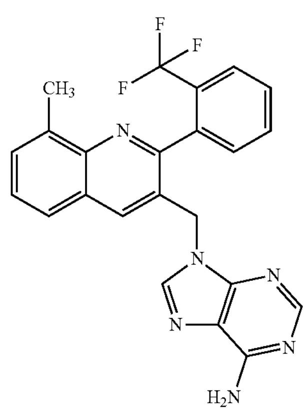 [SMILES: Cc1cccc2cc(Cn3cnc4c(N)ncnc43)c(-c3ccccc3C(F)(F)F)nc12] | 9-({8-methyl-2-[2-(trifluoromethyl)phenyl]quinolin-3-yl}methyl)-9H-purin-6-amine |
| 183 | 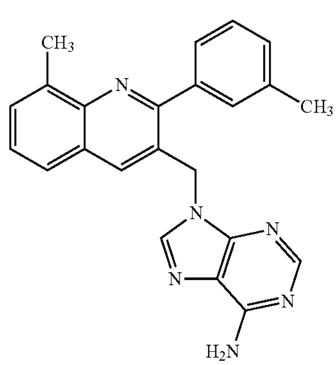 [SMILES: Cc1cccc(-c2nc3c(C)cccc3cc2Cn2cnc3c(N)ncnc32)c1] | 9-{[8-methyl-2-(3-methylphenyl)quinolin-3-yl]methyl}-9H-purin-6-amine |

TABLE 1-continued

| Compound | Structure | Name |
|---|---|---|
| 184 | 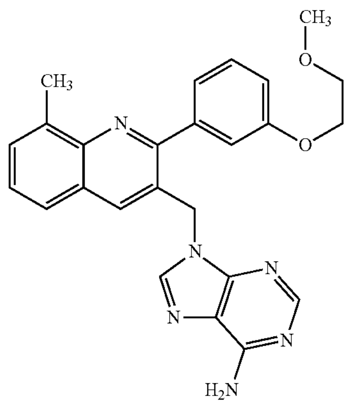 [SMILES: COCCOc1cccc(-c2nc3c(C)cccc3cc2Cn2cnc3c(N)ncnc32)c1] | 9-{[8-methyl-2-(3-{[2-(methyloxy)ethyl]oxy}phenyl)quinolin-3-yl]methyl}-9H-purin-6-amine |
| 185 | 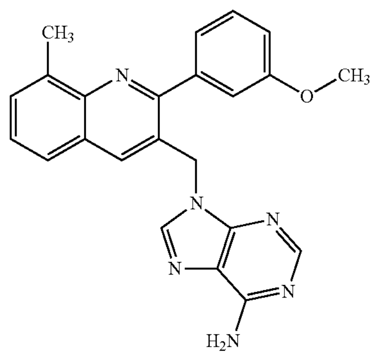 [SMILES: COc1cccc(-c2nc3c(C)cccc3cc2Cn2cnc3c(N)ncnc32)c1] | 9-({8-methyl-2-[3-(methyloxy)phenyl]quinolin-3-yl}methyl)-9H-purin-6-amine |
| 186 | 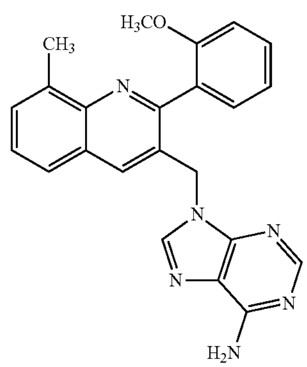 [SMILES: COc1ccccc1-c1nc2c(C)cccc2cc1Cn1cnc2c(N)ncnc21] | 9-({2-[2-(ethyloxy)phenyl]-8-methylquinolin-3-yl}methyl)-9H-purin-6-amine |
| 187 | 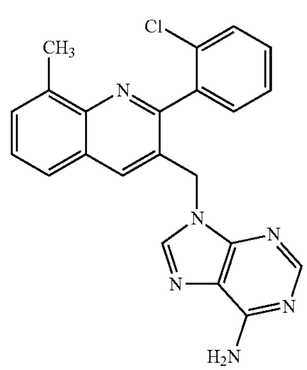 [SMILES: Cc1cccc2cc(Cn3cnc4c(N)ncnc43)c(-c3ccccc3Cl)nc12] | 9-{[2-(2-chlorophenyl)-8-methylquinolin-3-yl]methyl}-9H-purin-6-amine |

TABLE 1-continued

| Compound | Structure | Name |
|---|---|---|
| 188 | 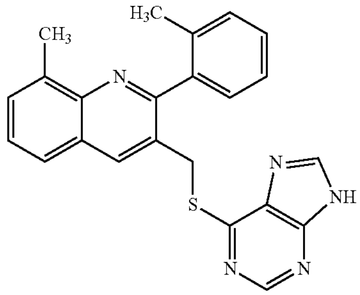 [SMILES: Cc1ccccc1-c1nc2c(C)cccc2cc1CSc1ncnc2[nH]cnc12] | 8-methyl-2-(2-methylphenyl)-3-[(9H-purin-6-ylthio)methyl]quinoline |
| 189 | 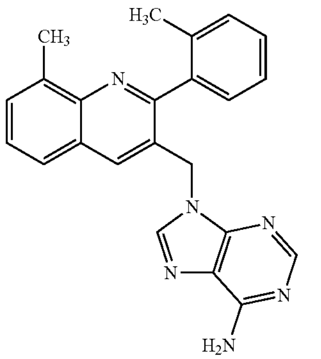 [SMILES: Cc1ccccc1-c1nc2c(C)cccc2cc1Cn1cnc2c(N)ncnc21] | 9-{[8-methyl-2-(2-methylphenyl)quinolin-3-yl]methyl}-9H-purin-6-amine |
| 190 | 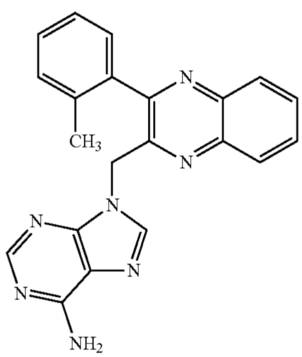 [SMILES: Cc1ccccc1-c1nc2ccccc2nc1Cn1cnc2c(N)ncnc21] | 9-{[3-(2-methylphenyl)quinoxalin-2-yl]methyl}-9H-purin-6-amine |
| 191 | 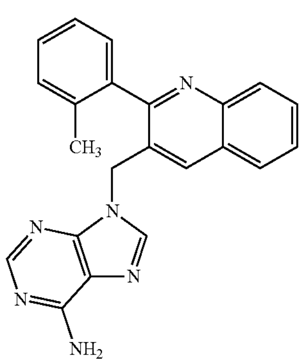 [SMILES: Cc1ccccc1-c1nc2ccccc2cc1Cn1cnc2c(N)ncnc21] | 9-{[2-(2-methylphenyl)quinolin-3-yl]methyl}-9H-purin-6-amine |

In another aspect, the invention provides a pharmaceutical composition which comprises 1) a compound, as a single stereoisomer or mixture of isomers thereof, according to any one of Formula compounds of Formula I, or according to any one of the above embodiments or a compound in Table 1, optionally as a pharmaceutically acceptable salt thereof, and 2) a pharmaceutically acceptable carrier, excipient, and/or diluent thereof.

In another aspect, the invention provides a method of treating disease, disorder, or syndrome where the disease is associated with uncontrolled, abnormal, and/or unwanted cellular activities effected directly or indirectly by PI3K delta which method comprises administering to a human in need thereof a therapeutically effective amount of a compound of any of Formula to any one of Formula compounds of Formula I, a compound of any one of the above embodiments, or a compound from Table 1, optionally as a pharmaceutically acceptable salt or pharmaceutical composition thereof. In another embodiment of embodiment (V), the disease is cancer. In another embodiment of embodiment (V), the disease is cancer and the Compound is of Formula I or a Compound from Table 1.

In another aspect, the invention provides a method of treating a disease, disorder, or syndrome which method comprises administering to a patient a therapeutically effective amount of a compound of any of Formula I, a compound of any one of the above embodiments, or a compound from Table 1, optionally as a pharmaceutically acceptable salt thereof, or a pharmaceutical composition comprising a therapeutically effective amount of a compound of Formula I, a compound of any one of the above embodiments, or a compound from Table 1, and a pharmaceutically acceptable carrier, excipient, or diluent.

In another embodiment, the disease is cancer. and the Compound is the compound of Formula I or a compound from Table 1.

General Administration

In one aspect, the invention provides pharmaceutical compositions comprising an inhibitor of PI3K delta according to the invention and a pharmaceutically acceptable carrier, excipient, or diluent. In certain other specific embodiments, administration is by the oral route. Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, specifically in unit dosage forms suitable for simple administration of precise dosages.

The compositions will include a conventional pharmaceutical carrier or excipient and a compound of the invention as the/an active agent, and, in addition, may include carriers and adjuvants, etc.

Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc.

The choice of formulation depends on various factors such as the mode of drug administration (e.g., for oral administration, formulations in the form of tablets, pills or capsules) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One specific route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Compressed gases may be used to disperse a compound of this invention in aerosol form. Inert gases suitable for this purpose are nitrogen, carbon dioxide, etc.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts or solvates, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

If formulated as a fixed dose, such combination products employ the compounds of this invention within the dosage range described above and the other pharmaceutically active agent(s) within its approved dosage range. Compounds of the instant invention may alternatively be used sequentially with known pharmaceutically acceptable agent(s) when a combination formulation is inappropriate.

Utility

Compounds of the Invention have activity for PI3K-delta. Compounds of this invention have been tested using the assays described in the Biological Examples and have been determined t be inhibitors of PI3K-delta. Suitable in vitro assays for measuring PI3K delta activity and the inhibition thereof by compounds are known in the art. For further details of an in vitro assay for measuring PI3K delta, see the Biological Examples herein. Cell-based assays for measurement of in vitro efficacy in treatment of cancer are known in the art. In addition, assays are described in the Biological Examples provided herein. Suitable in vivo models for cancer are known to those of ordinary skill in the art. For further details of in vivo models for prostate adenocarcinoma, glioblastoma, lung carcinoma, and melanoma, see the Biological Examples described herein. Following the examples disclosed herein, as well as that disclosed in the art, a person of ordinary skill in the art can determine the activity of a compound of this invention.

Compounds of Formula I are useful for treating diseases, including autoimmune disorders, inflammatory diseases, and cancers, which are listed below.

Cancers: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinorna, glucagonoma, gastrinoma, carcinoid tumors, vipoma), small bowel (adenocarcinorna, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [neplrroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma.

Autoimmune Diseases: Hashimoto's thyroiditis, systemic lupus erythematosus (SLE), Goodpasture's syndrome, pemphigus, receptor autoimmune diseases, Basedow's disease (Graves' disease), myasthernia gravis, insulin resistant diseases, autoimmune hemolytic anemia, autoimmune thrombocytopenic purpura, autoimmune encephalomyelitis, rheumatism, rheumatoid arthritis, scleroderma, mixed connective tissue disease, polymyositis, pernicious anemia, idiopathic Addison's disease, some types of infertility, glomerulonephritis, bullous pemphigus, Sjogren's syndrome, some types of diabetes, adrenergic agent resistance, chronic active hepatitis, primary biliary cirrhosis, endocrine failure, vitiligo, angiitis, post-cardiac surgery syndrome, urticaria, atopic dermatiti and multiple sclerosis, autoimmune polyglandular disease (also known as autoimmune polyglandular syndrome), autoimmune alopecia; pernicious anemia; vitiligo; autoimmune hypopituatarism, and Guillain-Barre syndrome.

Inflammatory Diseases: asthma, allergic rhinitis, psoriasis, inflammatory arthritis, rheumatoid arthritis, psoriatic arthritis or osteoarthritis, irritable bowel syndrome, ulcerative colitis, Crohn's disease, respiratory allergies (asthma, hay fever, allergic rhinitis) or skin allergies, scleracierma, mycosis fungoides, acute inflammatory responses (such as acute respiratory distress syndrome and ishchemia/reperfusion injury), dermatomyositis, alopecia greata, chronic actinic dermatitis, eczema, Behcet's disease, Pustulosis palmoplanteris, Pyoderma gangrenum, Sezary's syndrome, atopic dermatitis, systemic sclerosis, and morphea.

Thus, in one embodiment, the invention provides a method of inhibiting PI3K delta comprising contacting the PI3K delta with an effective amount of a compound as disclosed herein.

In another embodiment, the invention provides a method of treating a PI3K delta modulated disease comprising administering to a mammal in need of such treatment a therapeutically effective amount of a compound as disclosed herein In another embodiment, the invention provides a method of treating cancer disease mediated by PI3K delta comprising administering to a mammal in need of such treatment a therapeutically effective amount of a compound as disclosed herein.

Compounds of the invention are also useful as inhibitors of PI3Kdelta in vivo for studying the in vivo role of PI3K delta in biological processes, including the diseases described herein. Accordingly, the invention also comprises a method of inhibiting PI3K delta in vivo comprising administering a compound or composition of the invention to a mammal.

General Synthesis

Compounds of this invention can be made by the synthetic procedures described below. The starting materials and reagents used in preparing these compounds are either available from commercial suppliers such as Aldrich Chemical Co. (Milwaukee, Wis.), or Bachem (Torrance, Calif.), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4$^{th}$ Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure. The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure and over a temperature range from about −78° C. to about 150° C., more specifically from about 0° C. to about 125° C. and more specifically at about room (or ambient) temperature, e.g., about 20° C. Unless otherwise stated (as in the case of hydrogenation), all reactions are performed under an atmosphere of nitrogen.

Prodrugs can be prepared by techniques known to one skilled in the art. These techniques generally modify appropriate functional groups in a given compound. These modified functional groups regenerate original functional groups by routine manipulation or in vivo. Amides and esters of the compounds of the present invention may be prepared according to conventional methods. A thorough discussion of prodrugs is provided in T. Higuchi and V. Stella, "Prodrugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

The compounds of the invention, or their pharmaceutically acceptable salts, may have asymmetric carbon atoms or quaternized nitrogen atoms in their structure. Compounds of the Invention that may be prepared through the syntheses described herein may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention.

Some of the compounds of the invention contain an active ketone —C(O)CF$_3$ and may exist in part or in whole as the —C(OH$_2$)CF$_3$ form. Regardless of whether the compound is drawn as the —C(O)CF$_3$ or —C(OH$_2$)CF$_3$ form, both are included within the scope of the Invention. Although an individual compound may be drawn as the —C(O)CF$_3$ form, one of ordinary skill in the art would understand that the compound may exist in part or in whole as the —C(OH$_2$)CF$_3$ form and that the ratio of the two forms may vary depending on the compound and the conditions in which it exists.

Some of the compounds of the invention may exist as tautomers. For example, where a ketone or aldehyde is present, the molecule may exist in the enol form; where an amide is present, the molecule may exist as the imidic acid; and where an enamine is present, the molecule may exist as an imine. All such tautomers are within the scope of the invention. Regardless of which structure or which terminology is used, each tautomer is included within the scope of the Invention.

The present invention also includes N-oxide derivatives and protected derivatives of compounds of the Invention. For example, when compounds of the Invention contain an oxidizable nitrogen atom, the nitrogen atom can be converted to an N-oxide by methods well known in the art. When compounds of the Invention contain groups such as hydroxy, carboxy, thiol or any group containing a nitrogen atom(s), these groups can be protected with a suitable "protecting group" or "protective group". A comprehensive list of suitable protective groups can be found in T. W. Greene, *Protective Groups in Organic Synthesis*, John Wiley & Sons, Inc. 1991, the disclosure of which is incorporated herein by reference in its entirety. The protected derivatives of compounds of the Invention can be prepared by methods well known in the art.

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents or by converting on enantiomer to the other by asymmetric transformation. For a mixture of enantiomers, enriched in a particular enantiomer, the major component enantiomer may be further enriched (with concomitant loss in yield) by recrystallization.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The chemistry for the preparation of the compounds of this invention is known to those skilled in the art. In fact, there may be more than one process to prepare the compounds of the invention. The following examples illustrate but do not limit the invention. All references cited herein are incorporated by reference in their entirety.

SYNTHETIC EXAMPLES

N-(2-((3-((9H-Purin-6-ylamino)methyl)-8-methylquinolin-2-yl)(methylamino)ethyl)-N-methyl-2-(1H-1,2,3-triazol-1-yl)acetamide (7)

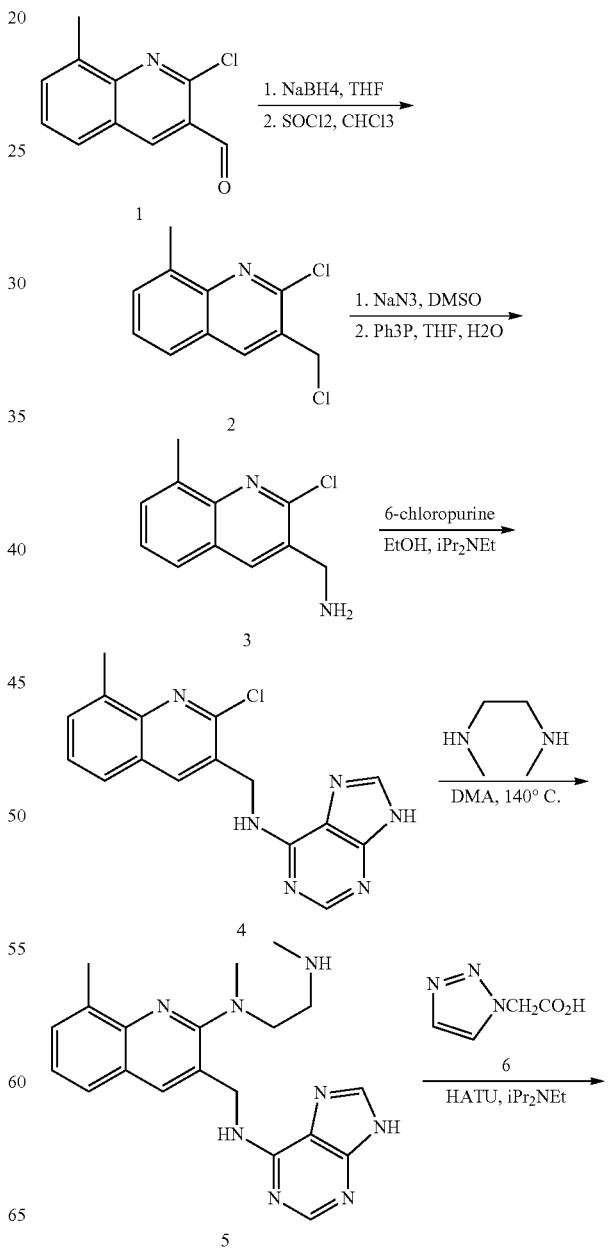

131

-continued

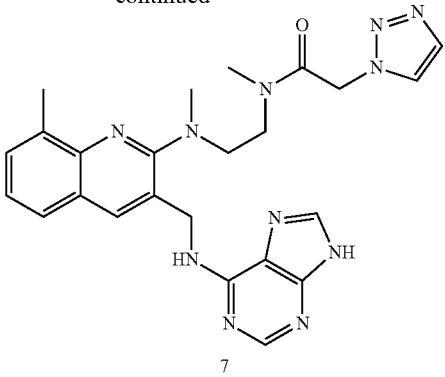

7

2-Chloro-3-(chloromethyl)-8-methylquinoline (2)

To a stirred solution of 2-chloro-8-methylquinoline-3-carboxaldehyde (1, 7.59 g, 36.9 mmol) in THF (150 mL) was added NaBH$_4$ (1.40 g, 37.0 mmol) and the reaction mixture was stirred at rt for 2 h. The reaction mixture was concentrated under reduced pressure and the residue was triturated with satd. NaHCO$_3$ (aq., 200 mL). Precipitates were collected by filtration, washed with H$_2$O, and dried under high vacuum to give the alcohol (7.47 g, 97%) as a white solid. MS (EI) for C$_{11}$H$_{10}$ClNO. found 208 (MH$^+$).

To a stirred suspension of the alcohol obtained above (7.47 g, 36.0 mmol) in CHCl$_3$ (150 mL) was added SOCl$_2$ (13.1 ml, 180 mmol) slowly and the resulting mixture was stirred at rt for 3 h. The reaction mixture was carefully quenched with H$_2$O (10 mL), diluted with satd. NaHCO$_3$ (aq., 200 mL), and the separated aqueous layer was extracted with CH$_2$Cl$_2$ (200 mL). The combined extracts were dried over anhydrous sodium sulfate and concentrated under reduced pressure to give 2-chloro-3-(chloromethyl)-8-methylquinoline (2, 8.01 g, 98%) as colorless oil. MS (EI) for C$_{11}$H$_9$Cl$_2$N. found 226 (MH$^+$).

1(2-Chloro-8-methylquinoline-3-yl)methanamine (3)

To a stirred solution of 2 (8.01 g, 35.4 mmol) in DMSO (150 mL) was added NaN$_3$ (4.61 g, 70.9 mmol) portionwise and the resulting mixture was stirred at rt for 4 h. The reaction mixture was diluted with EtOAc (300 mL)/H$_2$O (200 mL). The separated organic layer was washed with brine, dried over anhydrous sodium sulfate, and concentrated under reduced pressure to afford the azide (7.66 g, 32.9 mmol). MS (EI) for C$_{11}$H$_9$ClN$_4$. found 233 (MH$^+$).

To a stirred solution of the azide in THF (150 mL)/H$_2$O (20 mL) was added Ph$_3$P (12.9 g, 49.2 mmol) and the reaction mixture was stirred at rt for 4 h at which time it was diluted with 1N HCl (150 mL)/CH$_2$Cl$_2$ (300 mL). The separated aqueous layer was washed with CH$_2$Cl$_2$ (100 mL) and basified with 1N NaOH to pH >10. The precipitated product 3 (5.12 g) was collected by filtration, washed with H$_2$O, and dried under high vacuum. The filtrates were extracted with CH$_2$Cl$_2$ (3×100 mL). The combined extracts were dried over anhydrous sodium sulfate and concentrated under reduced pressure to give an additional aliquot of the product (0.77 g). The combined yield was 87% (5.89 g). MS (EI) for C$_{11}$H$_{11}$ClN$_2$. found 207 (MH$^+$).

N-((2-Chloro-8-methylquinolin-3-yl)methyl)-9H-purin-6-amine (4)

A mixture of 3 (620 mg, 3.00 mmol), 6-chloropurine (487 mg, 3.15 mmol) and Hunig's base (0.627 mL, 3.60 mmol)

132 was stirred 1 h at 80° C. in EtOH (30 mL). The precipitate was filtered and the solid was washed with water and EtOH to give 4 (726 mg, 75%) MS (EI) for C$_{16}$H$_{13}$ClN$_6$. found 325 (MH+).

N$^1$-(3-((9H-Purin-6-ylamino)methyl)-8-methylquinolin-2-yl)-N$^1$,N$^2$-dimethylethane-1,2-diamine (5)

A mixture of 4 (187 mg, 0.58 mmol) and N,N'-dimethylethylenediamine (0.624 mL, 5.8 mmol) in DMA (1.5 ml) was stirred at 140° C. for 1.5 h. The reaction mixture was concentrated under reduced pressure and the residue was purified by flash chromatography to give 5 (165 mg, 76%). MS (EI) for C$_{20}$H$_{24}$N$_8$. found 377 (MH+).

N-(2-((3-((9H-Purin-6-ylamino)methyl)-8-methylquinolin-2-yl)(methylamino)ethyl)-N-methyl-2-(1H-1,2,3-triazol-1-yl)acetamide (7)

To a stirred mixture of 5 (65 mg, 0.173 mmol), 1-1,2,3-triazoleacetic acid (6, 22 mg, 0.173 mmol), and Hunig's base (0.091 mL, 0.522 mmol) in DMF (2 ml) was added HATU (66 mg, 0.174 mmol) and the reaction mixture was stirred for 30 min. The crude mixture was directly purified by prep. HPLC to give 7 (39 mg, 46%). $^1$H-NMR (400MHz, d6-DMSO): δ13.0 (s, 1H), 8.34 (bs, 1H), 8.16-8.11 (m, 2H), 8.00-7.95 (m, 2H), 7.71 (s, 1H), 7.55-7.42 (m, 2H), 7.19 (q, 1H), 5.51-5.43 (2 s, 2H), 4.86-4.83 (m, 2H), 3.81-3.52 (m, 4H), 3.13-3.12 (2 s, 3H), 3.04-2.97 (2 s, 3H), 2.64-2.63 (2 s, 3H). MS (EI) for C$_{24}$H$_{27}$N$_{11}$O, found 486 (MH+).

In a similar manner, the following compounds were prepared:

N,8-dimethyl-N-[(1-methylpiperidin-4-yl)methyl]-3-[(9H-purin-6-ylthio)methyl]quinolin-2-amine (CMPD 1);

3-[(6-amino-9H-purin-9-yl)methyl]-N,8-dimethyl-N-[(1-methylpyrrolidin-2-yl)methyl]quinolin-2-amine (CMPD 2);

3-[(6-amino-9H-purin-9-yl)methyl]-N,8-dimethyl-N-[(1-methylpiperidin-2-yl)methyl]quinolin-2-amine (CMPD 3);

3-[(6-amino-9H-purin-9-yl)methyl]-N,8-dimethyl-N-[(1-methylpiperidin-4-yl)methyl]quinolin-2-amine (CMPD 4);

N-{[2-(2-chlorophenyl)-8-methylquinolin-3-yl]methyl}-2,3-dihydro-1,4-benzodioxin-5-amine (CMPD 5);

N-{[8-methyl-2-(octahydro-2H-pyrido[1,2-a]pyrazin-2-yl)quinolin-3-yl]methyl}-9H-purin-6-amine (CMPD 12);

9-{[8-methyl-2-(octahydroisoquinolin-2(1H)-yl)quinolin-3-yl]methyl}-9H-purin-6-amine (CMPD 13);

9-{[2-(3,4-dihydroisoquinolin-2(1H)-yl)-8-methylquinolin-3-yl]methyl}-9H-purin-6-amine (CMPD 14);

N-{[2-(3,4-dihydroisoquinolin-2(1H)-yl)-8-methylquinolin-3-yl]methyl}-9H-purin-6-amine (CMPD 19);

N,8-dimethyl-N-[2-(methyloxy)ethyl]-3-[(9H-purin-6-ylamino)methyl]quinolin-2-amine (CMPD 25);

N-butyl-N,8-dimethyl-3-[(9H-purin-6-ylamino)methyl]quinolin-2-amine (CMPD 26);

N-[(8-methyl-2-piperidin-1-ylquinolin-3-yl)methyl]-9H-purin-6-amine (CMPD 27);

N-{2-[{3-[(6-amino-9H-purin-9-yl)methyl]-8-methylquinolin-2-yl}(methyl)amino]ethyl}-N-methyl-2-(1H-pyrazol-1-yl)acetamide (CMPD 28);

N,8-dimethyl-N-[(1-methylpiperidin-3-yl)methyl]-3-[(9H-purin-6-ylamino)methyl]quinolin-2-amine (CMPD 32);

N,8-dimethyl-N-[(1-methylpiperidin-4-yl)methyl]-3-[(9H-purin-6-ylamino)methyl]quinolin-2-amine (CMPD 33);

N-{2-[{3-[(6-amino-9H-purin-9-yl)methyl]-8-methylquinolin-2-yl}(methyl)amino]ethyl}-N-methyl-2-(1H-1,2,3-triazol-1-yl)acetamide (CMPD 34);

N,N'-dimethyl-N-{8-methyl-3-[(9H-purin-6-ylamino)methyl]quinolin-2-yl}ethane-1,2-diamine (CMPD 36);

N-[(8-methyl-2-piperazin-1-ylquinolin-3-yl)methyl]-9H-purin-6-amine (CMPD 37);

N,8-dimethyl-N-[(1-methylpiperidin-2-yl)methyl]-3-[(9H-purin-6-ylamino)methyl]quinolin-2-amine (CMPD 38);

3-iodo-1-{1-[3-(2-methylphenyl)quinolin-2-yl]ethyl}-1H-pyrazolo[3,4-d]pyrimidin-4-amine (CMPD 117);

3-iodo-1-{[5-methyl-3-(2-methylphenyl)quinolin-2-yl]methyl}-1H-pyrazolo[3,4-d]pyrimidin-4-amine (CMPD 119);

9-{[3-(2-methylphenyl)naphthalen-2-yl]methyl}-9H-purin-6-amine (CMPD 120);

3-iodo-1-{[8-methyl-2-(2-methylphenyl)quinolin-3-yl]methyl}-1H-pyrazolo[3,4-d]pyrimidin-4-amine (CMPD 134);

3-iodo-N-{[8-methyl-2-(2-methylphenyl)quinolin-3-yl]methyl}-1H-pyrazolo[3,4-d]pyrimidin-4-amine (CMPD 135);

3-bromo-N-{[3-(2-methylphenyl)quinolin-2-yl]methyl}-1H-pyrazolo[3,4-d]pyrimidin-4-amine (CMPD 141);

N-{[2-(4-acetylpiperazin-1-yl)-8-methylquinolin-3-yl]methyl}-9H-purin-6-amine (CMPD 143);

N-{[2-(4-ethylpiperazin-1-yl)-8-methylquinolin-3-yl]methyl}-9H-purin-6-amine (CMPD 144);

3-iodo-1-{[3-(2-methylphenyl)quinolin-2-yl]methyl}-1H-pyrazolo[3,4-d]pyrimidin-4-amine (CMPD 145);

N-{[8-methyl-2-(4-methyl-1,4-diazepan-1-yl)quinolin-3-yl]methyl}-9H-purin-6-amine (CMPD 146);

N-{3-[(6-amino-9H-purin-9-yl)methyl]-8-methylquinolin-2-yl}-N,N'-dimethylethane-1,2-diamine (CMPD 149);

9-{[8-methyl-2-(5-methyl-2,5-diazabicyclo[2.2.1]hept-2-yl)quinolin-3-yl]methyl}-9H-purin-6-amine (CMPD 150);

N-{1-[2-(2-chlorophenyl)-8-methylquinolin-3-yl]ethyl}-9H-purin-6-amine (CMPD 152);

N-{3-[(6-amino-9H-purin-9-yl)methyl]-8-methylquinolin-2-yl}methanesulfonamide (CMPD 153);

N-{[2-(2-chlorophenyl)-8-methylquinolin-3-yl]methyl}-9H-purin-6-amine (CMPD 154);

N-{[3-(2-methylphenyl)quinolin-2-yl]methyl}-9H-purin-6-amine (CMPD 155);

N-{3-[(6-amino-9H-purin-9-yl)methyl]-8-methylquinolin-2-yl}benzenesulfonamide (CMPD 156);

2-[(6-amino-9H-purin-9-yl)methyl]-3-(2-methylphenyl)thieno[3,2-d]pyrimidin-4(3H)-one (CMPD 162);

3-(2-methylphenyl)-2-[(7H-purin-6-ylthio)methyl]thieno[3,2-d]pyrimidin-4(3H)-one (CMPD 163);

3-[(6-amino-9H-purin-9-yl)methyl]-8-methyl-N-(1-methylpiperidin-4-yl)quinolin-2-amine (CMPD 164);

3-[(6-amino-9H-purin-9-yl)methyl]-8-methyl-N-(tetrahydro-2H-pyran-4-yl)quinolin-2-amine (CMPD 165);

9-{[2-(4-acetylpiperazin-1-yl)-8-methylquinolin-3-yl]methyl}-9H-purin-6-amine (CMPD 166);

3-[(6-amino-9H-purin-9-yl)methyl]-8-methyl-N-[2-(methyloxy)ethyl]quinolin-2-amine (CMPD 167);

9-{[4-methyl-3-(2-methylphenyl)quinolin-2-yl]methyl}-9H-purin-6-amine (CMPD 168);

7-{[4-methyl-3-(2-methylphenyl)quinolin-2-yl]methyl}-7H-purin-6-amine (CMPD 169);

9-{[8-methyl-2-(2-methylpyrrolidin-1-yl)quinolin-3-yl]methyl}-9H-purin-6-amine (CMPD 170);

9-[(8-methyl-2-pyrrolidin-1-ylquinolin-3-yl)methyl]-9H-purin-6-amine (CMPD 171);

9-[(8-methyl-2-piperazin-1-ylquinolin-3-yl)methyl]-9H-purin-6-amine (CMPD 172);

9-{[8-methyl-2-(4-methylpiperazin-1-yl)quinolin-3-yl]methyl}-9H-purin-6-amine (CMPD 173);

9-[(8-methyl-2-morpholin-4-ylquinolin-3-yl)methyl]-9H-purin-6-amine (CMPD 177);

7-{([3-(2-methylphenyl)quinolin-2-yl]methyl}-7H-purin-6-amine (CMPD 178);

9-{[3-(2-methylphenyl)quinolin-2-yl]methyl}-9H-purin-6-amine (CMPD 179);

9-{[2-(2,3-dimethylphenyl)-8-methylquinolin-3-yl]methyl}-9H-purin-6-amine (CMPD 180);

9-{[2-(2,5-dimethylphenyl)-8-methylquinolin-3-yl]methyl}-9H-purin-6-amine (CMPD 181);

9-({8-methyl-2-[2-(trifluoromethyl)phenyl]quinolin-3-yl}methyl)-9H-purin-6-amine (CMPD 182);

9-{[8-methyl-2-(3-methylphenyl)quinolin-3-yl]methyl}-9H-purin-6-amine (CMPD 183);

9-{[8-methyl-2-(3-([2-(methyloxy)ethyl]oxy)phenyl)quinolin-3-yl]methyl}-9H-purin-6-amine (CMPD 184);

9-({8-methyl-2-[3-(methyloxy)phenyl]quinolin-3-yl}methyl)-9H-purin-6-amine (CMPD 185);

9-({2-[2-(ethyloxy)phenyl]-8-methylquinolin-3-yl}methyl)-9H-purin-6-amine (CMPD 186);

9-{[2-(2-chlorophenyl)-8-methylquinolin-3-yl]methyl}-9H-purin-6-amine (CMPD 187);

8-methyl-2-(2-methylphenyl)-3-[(9H-purin-6-ylthio)methyl]quinoline (CMPD 188);

9-{[8-methyl-2-(2-methylphenyl)quinolin-3-yl]methyl}-9H-purin-6-amine (CMPD 189);

9-{[3-(2-methylphenyl)quinoxalin-2-yl]methyl}-9H-purin-6-amine (CMPD 190); and

9-{[2-(2-methylphenyl)quinolin-3-yl]methyl}-9H-purin-6-amine (CMPD 191).

3-Amino-N-{[5-methyl-3-(2-methylphenyl)-4-oxo-3,4-dihydroquinazolin-2-yl]methyl}pyrazine-2-carboxamide (13)

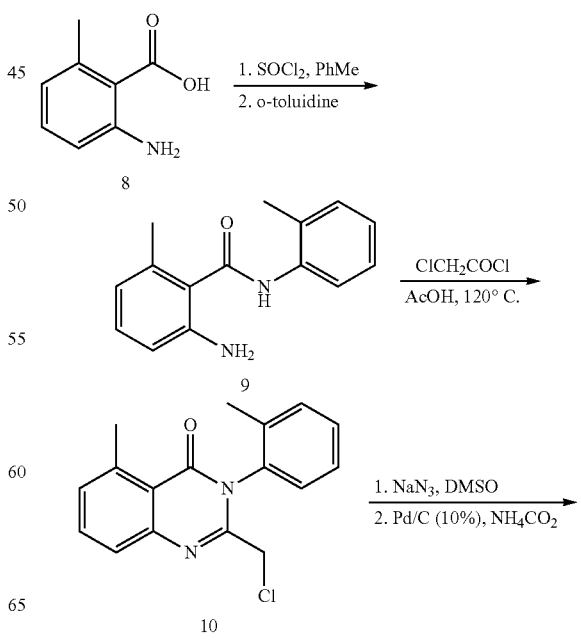

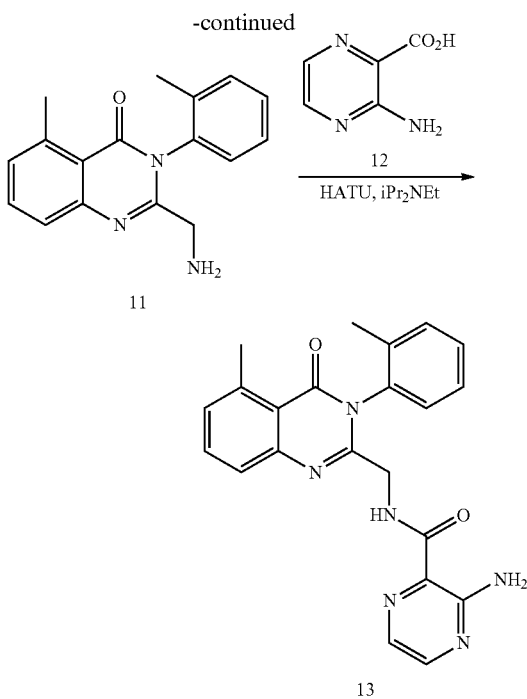

2-Amino-6-methyl-N-o-tolylbenzamide 2-amino-6-methylbenzoate (9)

Thionyl chloride (20.0 mL, 274 mmol) and 2-amino-6-methylbenzoic acid (8, 10.0 g, 66.2 mmol) was added to toluene (100 mL) and the mixture was heated to 110° C. for 1 h then concentrated. The crude acid chloride was dissolved in THF (100 mL), cooled to 0° C., and o-toluidine (21 mL, 196 mmol) was added slowly. The reaction mixture was heated to 80° C. and the product precipitated out over 2 h. The reaction mixture was then quenched with $K_2CO_3$ (10%, aq.), extracted with EtOAc, diluted with $Na_2SO_4$, filtered, and concentrated. The product was recrystallized from DCM/hexanes to provide 9 (14.7 g, 92% over 2 steps) as an off-white solid.

2-(Chloromethyl)-5-methyl-3-o-tolylquinazolin-4(3H)-one (10)

To 9 (13.7 g, 57.0 mmol) in AcOH (50 mL) was added 2-chloroacetyl chloride (13.6 mL, 171 mmol) and the reaction mixture was heated to 120° C. After 15 min the reaction mixture was diluted with $H_2O$ and extracted with EtOAc (2×). The organic layer was washed with $H_2O$ (2×), washed with brine, dried with $Na_2SO_4$, filtered, and concentrated. Flash column chromatography (Hexanes to 3:1 Hexanes/EtOAc) followed by trituration from EtOAc provided 10 (5.13 g, 26%) as a colorless solid.

2-(Aminomethyl)-5-methyl-3-o-tolylquinazolin-4(3H)-one (11)

To 10 (1.00 g, 3.36 mmol) in DMF (10 mL) was added sodium azide (0.436 g, 6.71 mmol) and the mixture was stirred at ambient temperature for 15 min. The crude reaction mixture was then diluted with methanol (20 mL) and ammonium formate (1.0 g, 16 mmol) followed by Pd/C (10%, 200 mg) was added. The reaction mixture was heated to 80° C. for 30 min at which time it was cooled to ambient temperature, filtered through Celite, and diluted with EtOAc and $H_2O$. The organic layer was washed with $H_2O$, brine, dried with $Na_2SO_4$, filtered, and concentrated. The crude 11 obtained in this manner was carried forward without further purification.

3-Amino-N-{[5-methyl-3-(2-methylphenyl)-4-oxo-3,4-dihydroquinazolin-2-yl]methyl}pyrazine-2-carboxamide (13)

3-Aminopyrazine-2-carboxylic acid (12, 39.0 mg, 0.280 mmol), Hunig's base (0.1 mL, 0.6 mmol), and HATU (108 mg, 0.280 mmol) were dissolved in DMF (0.5 mL) and the crude 11 obtained above (39.0 mg, 0.140 mmol) was added. The resulting reaction mixture was stirred at ambient temperature for 20 min then diluted with methanol and purified by preparative HPLC to give 13 (39.9 mg, 71%. $^1$H-NMR (400MHz, d6-DMSO): δ9.07 (t, 1H), 8.26 (s, 1H), 7.91 (s, 1H), 7.79-7.63 (m, 1H), 7.57-7.38 (m, 5H), 7.34 (d, 1H), 4.11 (dd, 1H), 3.81 (dd, 1H), 2.75 (s, 3H), 2.11 (s, 3H). MS (EI) for $C_{22}H_{20}N_6O_2$. found 401 (MH+).

In a similar manner, the following compounds were prepared:
1-[2-(2-chlorophenyl)-8-methylquinolin-3-yl]-N-{[3-(methyloxy)phenyl]methyl}methanamine (CMPD 6);
3-({[2-chloro-4-(methyloxy)phenyl]oxy}methyl)-2-(2-chlorophenyl)-8-methylquinoline (CMPD 7);
3[(1,3-benzodioxol-5-yloxy)methyl]-2-(2-chlorophenyl)-8-methylquinoline (CMPD 8);
N-{[2-(2-chlorophenyl)-8-methylquinolin-3-yl]methyl}-3,5-bis(methyloxy)aniline (CMPD 9);
N-[2-(2-chlorophenyl)-8-methylquinolin-3-yl]methyl)-3,4-bis(methyloxy)aniline (CMPD 10);
N-{[2-(2-chlorophenyl)-8-methylquinolin-3-yl]methyl}-2-(methyloxy)aniline (CMPD 11);
3-({[3,5-bis(methyloxy)phenyl]oxy}methyl)-2-(2-chlorophenyl)-8-methylquinoline (CMPD 15);
2-(2-chlorophenyl)-8-methyl-3-({[4-(methyloxy)phenyl]oxy}methyl)quinoline (CMPD 16);
2-(2-chlorophenyl)-8-methyl-3-(1-{[4-(methyloxy)phenyl]oxy}ethyl)quinoline (CMPD 17);
N-{[2-(2-chlorophenyl)-8-methylquinolin-3-yl]methyl}-3-(methyloxy)aniline (CMPD 18);
N,N'-dimethyl-N-[8-methyl-3-({[4-(methyloxy)phenyl]amino}methyl)quinolin-2-yl]ethane-1,2-diamine (CMPD 20);
N,N'-dimethyl-N-[8-methyl-3-(morpholin-4-ylmethyl)quinolin-2-yl]ethane-1,2-diamine (CMPD 21);
N,N'-dimethyl-N-[8-methyl-3-({[3-(methyloxy)phenyl]oxy}methyl)quinolin-2-yl]ethane-1,2-diamine (CMPD 22);
N,N'-dimethyl-N-[8-methyl-3-({[4-(methyloxy)phenyl]oxy}methyl)quinolin-2-yl]ethane-1,2-diamine (CMPD 23);
N,N'-dimethyl-N-[8-methyl-3-({[3-(methyloxy)phenyl]amino}methyl)quinolin-2-yl]ethane-1,2-diamine (CMPD 24);
N-{3-[5-(3-aminopyrazin-2-yl)-1,3,4-oxadiazol-2-yl]-8-methylquinolin-2-yl}-N,N'-dimethylethane-1,2-diamine (CMPD 29);
3-amino-N-[(8-methyl-2-{methyl[(1-methylpiperidin-3-yl)methyl]amino}quinolin-3-yl)methyl]pyrazine-2-carboxamide (CMPD 30);
3-amino-N-[(8-methyl-2-{methyl[(1-methylpiperidin-4-yl)methyl]amino}quinolin-3-yl)methyl]pyrazine-2-carboxamide (CMPD 31);

3-amino-N-[(8-methyl-2-(methyl[(1-methylpiperidin-2-yl)
methyl]amino)quinolin-3-yl)methyl]pyrazine-2-carbox-
amide (CMPD 39);
N-methyl-N-[(8-methyl-2-{methyl[2-(methylamino)ethyl]
amino}quinolin-3-yl)methyl]cyclopropane-1,1-dicarbox-
amide (CMPD 40);
3-{[3-(4-acetylpiperazin-1-yl)quinoxalin-2-yl]
amino}benzamide (CMPD 41);
3-amino-N-{[8-methyl-2-(methyl{2-[methyl(1H-tetrazol-1-
ylacetyl)amino]ethyl}amino)quinolin-3-yl]
methyl}pyrazine-2-carboxamide (CMPD 42);
3-amino-N-({2-[(2-{[(3,5-dimethyl-1H-1,2,4-triazol-1-yl)
acetyl](methyl)amino}ethyl)(methyl)amino]-8-meth-
ylquinolin-3-yl}methyl)pyrazine-2-carboxamide (CMPD
43);
3-amino-N-{[2-(3-{[2-(dimethylamino)-2-oxoethyl]
amino}pyrrolidin-1-yl)-8-methylquinolin-3-yl]
methyl}pyrazine-2-carboxamide (CMPD 44);
3-amino-N-[(8-methyl-2-[(3-{(1H-1,2,3-triazol-1-ylacetyl)
amino]pyrrolidin-1-yl}quinolin-3-yl)methyl]pyrazine-2-
carboxamide (CMPD 45);
3-amino-N-({2-[bis(pyridin-3-ylmethyl)amino]-8-meth-
ylquinolin-3-yl}methyl)pyrazine-2-carboxamide (CMPD
46);
3-amino-N-({2-[bis(pyridin-2-ylmethyl)amino]-8-meth-
ylquinolin-3-yl}methyl)pyrazine-2-carboxamide (CMPD
47);
3-amino-N-[(5-chloro-3-{2-[(dimethylamino)methyl]
phenyl}quinolin-2-yl)methyl]pyrazine-2-carboxamide
(CMPD 48);
3-amino-N-{[8-methyl-2-(methyl {2-[methyl(1H-pyrazol-
1-ylacetyl)amino]ethyl}amino)quinolin-3-yl]
methyl}pyrazine-2-carboxamide (CMPD 49);
3-amino-N-{[2-(3-hydroxypropyl)-8-methylquinolin-3-yl]
methyl}pyrazine-2-carboxamide (CMPD 50);
3-amino-N-{[8-methyl-2-(methyl {2-[(1H-1,2,3-triazol-1-
ylacetyl)amino]ethyl}amino)quinolin-3-yl]
methyl}pyrazine-2-carboxamide (CMPD 51);
3-amino-N-[(3-{2-[(dimethylamino)methyl]phenyl}-5-
methylquinolin-2-yl)methyl]pyrazine-2-carboxamide
(CMPD 52);
3-amino-N-({2-[4-(1H-benzimidazol-1-ylacetyl)-1,4-diaz-
epan-1-yl]-8-methylquinolin-3-yl}methyl)pyrazine-2-
carboxamide (CMPD 53);
3-amino-N-({2-[4-(1H-imidazol-1-ylacetyl)-1,4-diazepan-
1-yl]-8-methylquinolin-3-yl}methyl)pyrazine-2-carbox-
amide (CMPD 54);
3-amino-N-[(8-methyl-2-{4-[(2-methyl-1H-imidazol-1-yl)
acetyl]-1,4-diazepan-1-yl}quinolin-3-yl)methyl]pyra-
zine-2-carboxamide (CMPD 55);
3-amino-N-[(3-{2-[(dimethylamino)carbonyl]
phenyl}quinolin-2-yl)methyl]pyrazine-2-carboxamide
(CMPD 56);
3-amino-N-[(8-methyl-2-{4-[(1-methyl-1H-pyrrol-2-yl)
methyl]-1,4-diazepan-1-yl}quinolin-3-yl)methyl]pyra-
zine-2-carboxamide (CMPD 57);
3-amino-N-[(8-methyl-2-{(4-[(5-methylfuran-2-yl)methyl]-
1,4-diazepan-1-yl}quinolin-3-yl)methyl]pyrazine-2-car-
boxamide (CMPD 58);
3-amino-N-({3-[2-(piperidin-1-ylmethyl)phenyl]quinolin-
2-yl}methyl)pyrazine-2-carboxamide (CMPD 59);
3-amino-N-({8-methyl-2-[4-(1H-1,2,3-triazol-1-ylacetyl)-1,
4-diazepan-1-yl]quinolin-3-yl}methyl)pyrazine-2-car-
boxamide (CMPD 60);
3-amino-N-({8-methyl-2-[4-(2H-1,2,3-triazol-2-ylacetyl)-1,
4-diazepan-1-yl]quinolin-3-yl}methyl)pyrazine-2-car-
boxamide (CMPD 61);
3-amino-N-({8-methyl-2-[4-[(1-methyl-1H-imidazol-2-yl)
methyl]-1,4-diazepan-1-yl}quinolin-3-yl)methyl]pyra-
zine-2-carboxamide (CMPD 62);
3-amino-N-[(8-methyl-2-{4-[(1-methyl-1H-imidazol-5-yl)
methyl]-1,4-diazepan-1-yl}quinolin-3-yl)methyl]pyra-
zine-2-carboxamide (CMPD 63);
3-amino-N-((8-methyl-2-[4-(pyridin-3-ylmethyl)-1,4-diaz-
epan-1-yl]quinolin-3-yl)methyl)pyrazine-2-carboxamide
(CMPD 64);
3-amino-N-({8-methyl-2-[4-(pyridin-4-ylmethyl)-1,4-diaz-
epan-1-yl]quinolin-3-yl}methyl)pyrazine-2-carboxamide
(CMPD 65);
3-amino-N-[(2-{4-[2-(dimethylamino)-2-oxoethyl]-1,4-di-
azepan-1-yl}-8-methylquinolin-3-yl)methyl]pyrazine-2-
carboxamide (CMPD 66);
3-amino-N-{[8-methyl-2-(methyl{2-[methyl(1-propyl-D-
prolyl)amino]ethyl}amino)quinolin-3-yl]
methyl}pyrazine-2-carboxamide (CMPD 67);
3-amino-N-{[8-methyl-2-(methyl {2-[methyl(pyridin-2-yl-
methyl)amino]ethyl}amino)quinolin-3-yl]
methyl}pyrazine-2-carboxamide (CMPD 68);
3-amino-N-[(3-{3-[(dimethylamino)methyl]
phenyl}quinolin-2-yl)methyl]pyrazine-2-carboxamide
(CMPD 69);
3-amino-N-({3-[2-(morpholin-4-ylmethyl)phenyl]quinolin-
2-yl}methyl)pyrazine-2-carboxamide (CMPD 70);
3-amino-N-({3-[4-(morpholin-4-ylmethyl)phenyl]quinolin-
2-yl}methyl)pyrazine-2-carboxamide (CMPD 71);
3-amino-N-({3-[3-(morpholin-4-ylmethyl)phenyl]quinolin-
2-yl}methyl)pyrazine-2-carboxamide (CMPD 72);
3-amino-N-({8-methyl-2-[methyl(2-{methyl[1-(1-methyl-
ethyl)-D-prolyl]amino}ethyl)amino]quinolin-3-
yl}methyl)pyrazine-2-carboxamide (CMPD 73);
2-amino-N-{[3-(2-methylphenyl)quinolin-2-yl]
methyl}pyrimidine-5-carboxamide (CMPD 74);
3-amino-N-{1-[3-(2-methylphenyl)quinolin-2-yl]
ethyl}pyrazine-2-carboxamide (CMPD 75);
3-amino-N-({8-methyl-2-[methyl(2-{methyl[2-(methyl-
amino)-2-oxoethyl]amino}ethyl)amino]quinolin-3-
yl}methyl)pyrazine-2-carboxamide (CMPD 76);
3-amino-N-{[8-methyl-2-(methyl{2-[methyl(2-morpholin-
4-yl-2-oxoethyl)amino]ethyl}amino)quinolin-3-yl]
methyl}pyrazine-2-carboxamide (CMPD 77);
3-amino-N-{[8-methyl-2-(methyl{2-[methyl(pyrazin-2-yl-
carbonyl)amino]ethyl}amino)quinolin-3-yl]
methyl}pyrazine-2-carboxamide (CMPD 78);
3-amino-N{[8-methyl-2-(methyl {2-[methyl(pyridin-4-yl-
carbonyl)amino]ethyl}amino)quinolin-3-yl]
methyl}pyrazine-2-carboxamide (CMPD 79);
3-amino-N-{[8-methyl-2-(methyl {2-[methyl(pyridin-3-yl-
carbonyl)amino]ethyl}amino)quinolin-3-yl]
methyl}pyrazine-2-carboxamide (CMPD 80);
3-amino-N-{[8-methyl-2-(methyl{2-[methyl(pyridin-2-yl-
carbonyl)amino]ethyl}amino)quinolin-3-yl]
methyl}pyrazine-2-carboxamide (CMPD 81);
3-amino-N-((8-methyl-2-[methyl(2-{methyl[(4-methylphe-
nyl)sulfonyl]amino}ethyl)amino]quinolin-3-yl}methyl)
pyrazine-2-carboxamide (CMPD 82);
3-amino-N-{[8-methyl-2-(methyl{2-[methyl(pyridin-3-yl-
methyl)amino]ethyl}amino)quinolin-3-yl]
methyl}pyrazine-2-carboxamide (CMPD 83);
3-amino-N-({2-[{2-[(cyanomethyl)(methyl)amino]ethyl}
(methyl)amino]-8-methylquinolin-3-yl}methyl)pyrazine-
2-carboxamide (CMPD 84);
3-amino-N-({2-[{2-[(1H-imidazol-1-ylacetyl)(methyl)
amino]ethyl}(methyl)amino]-8-methylquinolin-3-
yl}methyl)pyrazine-2-carboxamide (CMPD 85);

3-amino-N-({8-methyl-2-[methyl[(2-methyl-1H-imidazol-1-yl)acetyl]amino}ethyl)amino]quinolin-3-yl)methyl)pyrazine-2-carboxamide (CMPD 86);

3-amino-N-({8-methyl-2-[methyl(pyridin-3-ylmethyl)amino]quinolin-3-yl}methyl)pyrazine-2-carboxamide (CMPD 87);

3-amino-N-({8-methyl-2-[methyl(2-pyridin-2-ylethyl)amino]quinolin-3-yl}methyl)pyrazine-2-carboxamide (CMPD 88);

3-amino-N-({2-[(2-{[2-(dimethylamino)-2-oxoethyl](methyl)amino}ethyl)(methyl)amino]-8-methylquinolin-3-yl}methyl)pyrazine-2-carboxamide (CMPD 89);

3-amino-N-{[8-methyl-2-(methyl{2-[methyl(pyrazin-2-yl)amino]ethyl}amino)quinolin-3-yl]methyl}pyrazine-2-carboxamide (CMPD 90);

3-amino-N-{[3-(1,3-thiazol-4-yl)quinolin-2-yl]methyl}pyrazine-2-carboxamide (CMPD 91);

3-amino-N-[(3-{2-[(dimethylamino)methyl]phenyl}quinolin-2-yl)methyl]pyrazine-2-carboxamide (CMPD 92);

3-amino-N-[(3-bromoquinolin-2-yl)methyl]pyrazine-2-carboxamide (CMPD 93);

3-amino-N-{[8-methyl-2-(methyl {2-[methyl(2H-1,2,3-triazol-2-ylacetyl)amino]ethyl}amino)quinolin-3-yl]methyl}pyrazine-2-carboxamide (CMPD 94);

3-amino-N-({8-methyl-2-[(pyridin-3-ylmethyl)amino]quinolin-3-yl}methyl)pyrazine-2-carboxamide (CMPD 95);

3-amino-N-({8-methyl-2-[(2-pyridin-2-ylethyl)amino]quinolin-3-yl}methyl)pyrazine-2-carboxamide (CMPD 96);

3-amino-N-({8-methyl-2-[(2-pyridin-3-ylethyl)amino]quinolin-3-yl}methyl)pyrazine-2-carboxamide (CMPD 97);

3-amino-N-({8-methyl-2-[methyl(1-methylpyrrolidin-3-yl)amino]quinolin-3-yl}methyl)pyrazine-2-carboxamide (CMPD 98);

3-amino-N-({8-methyl-2-[methyl(1-methylpiperidin-4-yl)amino]quinolin-3-yl}methyl)pyrazine-2-carboxamide (CMPD 99);

3-amino-N-{[8-methyl-2-(methyl{2-[methyl(1H-1,2,3-triazol-1-ylacetyl)amino]ethyl}amino)quinolin-3-yl]methyl}pyrazine-2-carboxamide (CMPD 100);

3-amino-N-{[8-methyl-2-(methyl 2-[methyl(methylsulfonyl)amino]ethyl}amino)quinolin-3-yl]methyl)pyrazine-2-carboxamide (CMPD 101);

3-amino-N-{[8-methyl-2-(methyl{2-[methyl(D-prolyl)amino]ethyl}amino)quinolin-3-yl]methyl}pyrazine-2-carboxamide (CMPD 102);

3-amino-N-{[8-methyl-2-(methyl{2-[methyl(L-prolyl)amino]ethyl}amino)quinolin-3-yl]methyl}pyrazine-2-carboxamide (CMPD 103);

3-amino-N-[(8-methyl-2-{methyl[2-(methyloxy)ethyl]amino}quinolin-3-yl)methyl]pyrazine-2-carboxamide (CMPD 104);

3-amino-N-{[3-(2-methylphenyl)quinolin-2-yl]methyl}-5-morpholin-4-ylpyrazine-2-carboxamide (CMPD 105);

3-amino-5-(methyloxy)-N-{[3-(2-methylphenyl)quinolin-2-yl]methyl}pyrazine-2-carboxamide (CMPD 106);

3-amino-5-chloro-N-{[3-(2-methylphenyl)quinolin-2-yl]methyl}pyrazine-2-carboxamide (CMPD 107);

4-amino-N-{[3-(2-methylphenyl)quinolin-2-yl]methyl}pyrimidine-5-carboxamide (CMPD 108);

3-amino-N{[8-methyl-2-(methyl{2-[methyl(pyrrolidin-1-ylacetyl)amino]ethyl}amino)quinolin-3-yl]methyl}pyrazine-2-carboxamide (CMPD 109);

3-amino-N-({8-methyl-2-[methyl(2-{methyl[(1-methyl-1H-imidazol-5-yl)carbonyl]amino}ethyl)amino]quinolin-3-yl}methyl)pyrazine-2-carboxamide (CMPD 110);

3-amino-N-[2-(1H-imidazol-1-yl)-8-methylquinolin-3-yl]methyl)pyrazine-2-carboxamide (CMPD 111);

3-amino-N-{[2-(1H-benzimidazol-1-yl)-8-methylquinolin-3-yl]methyl}pyrazine-2-carboxamide (CMPD 112);

3-amino-N-{[8-methyl-2-(methyl {2-[methyl(1-methyl-L-prolyl)amino]ethyl}amino)quinolin-3-yl]methyl}pyrazine-2-carboxamide (CMPD 113);

3-amino-N-({2-[{2-[(N,N-dimethylglycyl)(methyl)amino]ethyl}(methyl)amino]-8-methylquinolin-3-yl}methyl)pyrazine-2-carboxamide (CMPD 114);

3-amino-N-({2-[{2-[glycyl(methyl)amino]ethyl}(methyl)amino]-8-methylquinolin-3-yl}methyl)pyrazine-2-carboxamide (CMPD 115);

3-amino-N{[8-methyl-2-(methyl{2-[methyl(N-methylglycyl)amino]ethyl}amino)quinolin-3-yl]methyl}pyrazine-2-carboxamide (CMPD 116);

3-amino-N{[5-methyl-3-(2-methylphenyl)quinolin-2-yl]methyl}pyrazine-2-carboxamide (CMPD 118);

3-amino-N-({2-[(2-hydroxyethyl)(methyl)amino]-8-methylquinolin-3-yl}-methyl)pyrazine-2-carboxamide (CMPD 121);

3-amino-N-[(8-methyl-2-{[2-(methylamino)ethyl]oxy}quinolin-3-yl)methyl]pyrazine-2-carboxamide (CMPD 122);

3-amino-N-({2-[(2R,5S)-2,5-dimethylpiperazin-1-yl]-8-methylquinolin-3-yl}methyl)pyrazine-2-carboxamide (CMPD 123);

N-{[2-(4-acetylpiperazin-1-yl)-8-methylquinolin-3-yl]methyl}-3-aminopyrazine-2-carboxamide (CMPD 124);

3-amino-N-({2-[(2-hydroxyethyl)amino]-8-methylquinolin-3-yl}-methyl)pyrazine-2-carboxamide (CMPD 125);

1,1-dimethylethyl {1-[3-({[(3-aminopyrazin-2-yl)carbonyl]amino}methyl)-8-methylquinolin-2-yl]piperidin-4-yl}methylcarbamate (CMPD 126);

3-amino-N-({2-[4-(dimethylamino)piperidin-1-yl]-8-methylquinolin-3-yl}methyl)pyrazine-2-carboxamide (CMPD 127);

3-amino-N-[(2-([2-(dimethylamino)ethyl](methyl)amino)-8-methylquinolin-3-yl)methyl]pyrazine-2-carboxamide (CMPD 128);

3-amino-N-[(2-{[2-(dimethylamino)ethyl]amino}-8-methylquinolin-3-yl)methyl]pyrazine-2-carboxamide (CMPD 129);

3-amino-N-[(8-methyl-2-{methyl[2-(methylamino)ethyl]amino}quinolin-3-yl)methyl]pyrazine-2-carboxamide (CMPD 130);

3-amino-N-[(8-methyl-2-piperazin-1-ylquinolin-3-yl)methyl]pyrazine-2-carboxamide (CMPD 131);

N~5~-{[3-(2-methylphenyl)quinolin-2-yl]methyl}pyrimidine-4,5-diamine (CMPD 132);

3-amino-N-[(8-methyl-2-{methyl[3-(methylamino)propyl]amino}quinolin-3-yl)methyl]pyrazine-2-carboxamide (CMPD 133);

3-amino-N-({2-[{3-[(N,N-dimethylglycyl)(methyl)amino]propyl}(methyl)amino]-8-methylquinolin-3-yl}methyl)pyrazine-2-carboxamide (CMPD 136);

3-amino-N-({2-[4-(N,N-dimethylglycyl)-1,4-diazepan-1-yl]-8-methylquinolin-3-yl}methyl)pyrazine-2-carboxamide (CMPD 137);

3-amino-N-[(2-{[3-(dimethylamino)propyl]amino}-8-methylquinolin-3-yl)methyl]pyrazine-2-carboxamide (CMPD 138);

3-amino-N-{[2-(1,4-diazepan-1-yl)-8-methylquinolin-3-yl]methyl}pyrazine-2-carboxamide (CMPD 139);

3-amino-N-{[8-methyl-2-(4-methyl-1,4-diazepan-1-yl)quinolin-3-yl]methyl}pyrazine-2-carboxamide (CMPD 140);

3-amino-N-{[3-(2-methylphenyl)quinolin-2-yl]methyl}pyrazine-2-carboxamide (CMPD 142);
3-amino-N-[(8-methyl-2-piperidin-1-ylquinolin-3-yl)methyl]pyrazine-2-carboxamide (CMPD 147);
3-amino-N-{[2-(2-chlorophenyl)-8-methylquinolin-3-yl]methyl}pyrazine-2-carboxamide (CMPD 148);
N-{[5-methyl-3-(2-methylphenyl)-4-oxo-3,4-dihydroquinazolin-2-yl]methyl}-3-morpholin-4-ylpyrazine-2-carboxamide (CMPD 151);
2-(2-aminoethyl)-5-methyl-3-(2-methylphenyl)quinazolin-4(3H)-one (CMPD 157);
3-({[3,5-bis(methyloxy)phenyl]methyl}oxy)-8-methyl-2-(2-methylphenyl)quinoline (CMPD 158);
3-chloro-N-{[5-methyl-3-(2-methylphenyl)-4-oxo-3,4-dihydroquinazolin-2-yl]methyl}pyrazine-2-carboxamide (CMPD 159);
3-amino-6-bromo-N-{[5-methyl-3-(2-methylphenyl)-4-oxo-3,4-dihydroquinazolin-2-yl]methyl}pyrazine-2-carboxamide (CMPD 160);
3-amino-NA[5-methyl-3-(2-methylphenyl)-4-oxo-3,4-dihydroquinazolin-2-yl]methyl)pyridine-2-carboxamide (CMPD 161);
2-amino-N-{[5-methyl-3-(2-methylphenyl)-4-oxo-3,4-dihydroquinazolin-2-yl]methyl}pyridine-4-carboxamide (CMPD 174); and
2-amino-N-{[5-methyl-3-(2-methylphenyl)-4-oxo-3,4-dihydroquinazolin-2-yl]methyl}pyridine-3-carboxamide (CMPD 176).

BIOLOGICAL EXAMPLES

Example 1

Biochemical Assays

Kinase activity and compound inhibition were investigated using one or more of the assay formats described below. The ATP concentrations used in the various assays were approximately equal to or less than the $K_M$ for each of the respective kinases. Dose-response experiments were performed using an intra-plate dilution scheme with 10 different inhibitor concentrations in a 384-well microtiter plate. $IC_{50}$ values were calculated by nonlinear regression analysis using the four-parameter equation listed below:

$$Y=\min+(\max-\min)/(1+(X/IC_{50})^N)\qquad\text{Equation 1;}$$

where Y is the observed signal, X is the inhibitor concentration, min is the background signal in the absence of enzyme (0% enzyme activity), max is the signal in the absence of inhibitor (100% enzyme activity), $IC_{50}$ is the inhibitor concentration at 50% enzyme inhibition and N represents the empirical Hill slope as a measure of cooperativity. Typically N should approximate unity. Curve fitting was performed using XLFit or ActivityBase.

Luciferase-Coupled Chemiluminescence Assay Protocol

Kinase activity is measured as the percent of ATP consumed following the kinase reaction using luciferase-luciferin-coupled chemiluminescence. Reactions were conducted in 384 or 1536-well white medium binding microtiter plates (Greiner). Kinase reactions were initiated by combining test compounds, kinase, and ATP in a 20 μL volume (6 μL volume for 1536-well plate). The reaction mixture was incubated at ambient temperature for 2 h. Following the kinase reaction, a 20 μL (or 3 μL for 1536-well plate) aliquot of KinaseGlo (Promega) was added and the chemiluminescence signal measured using an EnVision plate reader (Perkin Elmer). Total ATP consumption was limited to 25-60% and the $IC_{50}$ values correlate well with those determined by radiometric assays.

PI3K delta activities of the Compounds of Formula I are provided in Table 2.

TABLE 2

PI3K Dalta Activity of Compounds of Formula I

| Compound | Activity IC50 |
|---|---|
| 1 | B |
| 2 | A |
| 3 | A |
| 4 | A |
| 5 | D |
| 6 | D |
| 7 | D |
| 8 | D |
| 9 | D |
| 10 | D |
| 11 | D |
| 12 | A |
| 13 | D |
| 14 | D |
| 15 | D |
| 16 | D |
| 17 | D |
| 18 | D |
| 19 | D |
| 20 | D |
| 21 | D |
| 22 | D |
| 23 | D |
| 24 | D |
| 25 | A |
| 26 | B |
| 27 | B |
| 28 | A |
| 29 | D |
| 30 | A |
| 31 | A |
| 32 | A |
| 33 | A |
| 34 | A |
| 35 | A |
| 36 | A |
| 37 | A |
| 38 | A |
| 39 | A |
| 40 | D |
| 41 | D |
| 42 | A |
| 43 | A |
| 44 | D |
| 45 | D |
| 46 | C |
| 47 | D |
| 48 | A |
| 49 | A |
| 50 | D |
| 51 | B |
| 52 | A |
| 53 | D |
| 54 | D |
| 55 | D |
| 56 | C |
| 57 | D |
| 58 | D |
| 59 | B |
| 60 | C |
| 61 | D |
| 62 | D |
| 63 | B |
| 64 | C |
| 65 | D |
| 66 | D |
| 67 | A |
| 68 | B |
| 69 | C |

TABLE 2-continued

PI3K Delta Activity of Compounds of Formula I

| Compound | Activity IC50 |
|---|---|
| 70 | C |
| 71 | D |
| 72 | D |
| 73 | A |
| 74 | D |
| 75 | C |
| 76 | B |
| 77 | B |
| 78 | D |
| 79 | B |
| 80 | C |
| 81 | C |
| 82 | D |
| 83 | A |
| 84 | B |
| 85 | A |
| 86 | A |
| 87 | B |
| 88 | D |
| 89 | A |
| 90 | D |
| 91 | D |
| 92 | B |
| 93 | D |
| 94 | B |
| 95 | D |
| 96 | D |
| 97 | D |
| 98 | B |
| 99 | B |
| 100 | A |
| 101 | B |
| 102 | B |
| 103 | B |
| 104 | D |
| 105 | D |
| 106 | D |
| 107 | D |
| 108 | D |
| 109 | B |
| 110 | B |
| 111 | C |
| 112 | D |
| 113 | B |
| 114 | B |
| 115 | B |
| 116 | B |
| 117 | A |
| 118 | C |
| 119 | A |
| 120 | D |
| 121 | B |
| 122 | D |
| 123 | C |
| 124 | C |
| 125 | D |
| 126 | D |
| 127 | D |
| 128 | A |
| 129 | D |
| 130 | C |
| 131 | D |
| 132 | D |
| 133 | B |
| 134 | A |
| 135 | B |
| 136 | A |
| 137 | C |
| 138 | D |
| 139 | C |
| 140 | C |
| 141 | D |
| 142 | D |
| 143 | A |
| 144 | A |
| 145 | A |
| 146 | A |
| 147 | D |
| 148 | B |
| 149 | A |
| 150 | D |
| 151 | D |
| 152 | A |
| 153 | D |
| 154 | A |
| 155 | B |
| 156 | D |
| 157 | D |
| 158 | D |
| 159 | D |
| 160 | D |
| 161 | D |
| 162 | D |
| 163 | D |
| 164 | D |
| 165 | D |
| 166 | B |
| 167 | D |
| 168 | D |
| 169 | D |
| 170 | B |
| 171 | B |
| 172 | B |
| 173 | B |
| 174 | D |
| 175 | A |
| 176 | D |
| 177 | B |
| 178 | B |
| 179 | D |
| 180 | D |
| 181 | B |
| 182 | B |
| 183 | C |
| 184 | C |
| 185 | C |
| 186 | C |
| 187 | B |
| 188 | B |
| 189 | B |
| 190 | D |
| 191 | D |

A 0 < PI3K Delta Activity < 50 nM
B 50 < PI3K Delta Activity < 250 nM
C 250 < PI3K Delta Activity < 500 nM
D 500 < PI3K Delta Activity < 1500 nM Reversibility of Inhibition The reversibility of enzyme inhibition is evaluated for PI3K delta by measuring residual enzyme activity after dilution of an enzyme-inhibitor complex in saturating ATP. Inhibitor complexes were formed by incubating PI3K delta (2 µM) and a compound of Formula I (2 µM) for 30 minutes at ambient temperature. The EI complex is then serially diluted into buffer and allowed to reach equilibrium. Quantitative inhibition (approximately 75%) of the EI complex is found by measuring enzyme activity without dilution into buffer. A 5 µL sample of each dilution is then transferred to a 384-well low-volume medium binding white plate and then a 5 µL aliquot of substrate (40 µM PIP$_2$) and 1 mM ATP is added to the plate. Following an incubation of the reaction (5-60 mins) a 10 µL aliquot of ADP-Glo Reagent #1 is added and incubated for 40 minutes. Finally, 10 µL of ADP-Glo Reagent #2 is added to the plate and following a 60 minute incubation the reactions were read on the Envision Microplate Reader.

Mechanism of Kinase Inhibition

Compounds of Formula I listed in Table 1 are characterized for reversibility of binding, inhibition type, and $K_i$ values. ATP variation studies are conducted by determining $IC_{50}$ values for Compound A against PI3 Kdelta using increasing ATP concentrations. The assays are conducted by mixing 2 µL of PI3 Kdelta with 0.1 µl, of compound in a 384-well low volume white medium binding plate. After a 15 minute incubation, 2 µL of substrate ($PIP_2$) and ATP at varying concentrations (1500, 1000, 500, 250, 1 µM final) are added to the plate. Following incubation of the kinase reaction (15-120 minutes), 4 µL of ADP-Glo (Promega) Reagent #1 is added to the entire plate and incubated for 40 minutes. Finally, 8 µL of ADP-Glo Reagent #2 is added to the entire plate, incubated for 60 minutes, and then the plate is read using an Envision microplate reader. The resulting $IC_{50}$ values are plotted as a function of ATP concentration, and $K_i$ values are derived using the following equation.

$$IC_{50}=K_i/K_M[ATP]+K_i+[E]/2 \qquad \text{Equation 2}$$

where [E] represents the concentration of enzyme.

Determination of $K_M$ Value for ATP

The $K_M$ value for ATP is determined using the ADP-GLO assay format described above. $K_M$ for ATP is derived by varying ATP concentrations (ranging from 15 to 1600 µM) at a fixed $PIP_2$ concentration (50 µM).

Example 2

Cellular Assays

Endogenous $AKT^{T308}$ Phosphorylation ELISA Assay in Anti-IgM Stimulated Raji Cells Raji cells (ATCC, CCL-86) are seeded at $1 \times 10^6$ cells/well onto 96-well plates (Corning, Costar 3960) in RPMI 1640 medium (ATCC, 30-2001) containing 10% FBS (Heat-Inactivated, Gibco, 10082), and 1% Penicillin/Streptomycin (Cellgro, 30-002-CI). Serial dilutions of test compounds in a final concentration of 0.3% DMSO (vehicle) are added to the cells and incubated for 90 min. Cells are stimulated with 0.25 µg/mL anti-IgM (Southern Biotech, 9023-01) for 30 min. Minimal signal wells are cells treated with 0.3% DMSO without anti-IgM stimulation; maximal signal wells are in 0.3% DMSO with anti-IgM stimulation. After stimulation, cells are spun down at 290×g for 4 min and immediately lysed with 120 µL of cold lysis buffer (50 mM Tris-HCl, pH 7.6; 150 mM NaCl; 0.1% Triton X-100; 1 mM EDTA; Protease Inhibitor Cocktail (Roche, 11697498001) and PhosSTOP (Roche, 04906837001)). To detect phospho-$AKT^{T308}$ and total AKT, commercially available ELISA kits are used (Invitrogen, KHO0201 and KHO0101). 100 or 10 µL of cell lysate is transferred to phospho-$AKT^{T308}$ or total AKT plates, respectively. An additional 90 µL of lysis buffer is added to the total AKT plates. Plates are incubated overnight at 4° C. and washed four times with 200 µL of manufacturer-provided ish buffer (Invitrogen, WB01). Plates are incubated with 100 µL of detection antibody solution for 1.5 h. Plates are ished four times with 200 µL of ish buffer, then incubated for 1 h with secondary antibody using the corresponding buffer. Plates are ished as above, followed by the addition of 100 µL/well of Stabilized Chromogen solution for 20 min. The reaction is stopped by adding 100 µL of Stop Solution. Absorbance at wavelength of 450 nm is measured using a spectrophotometer (Molecular Devices, SpectraMax Plus). Intra-well normalization is accomplished by dividing the phospho-$AKT^{T308}$ OD values by the total AKT OD values. $IC_{50}$ values are then estimated by comparing the values of compound-treated samples with averages of the aforementioned minimal and maximal signal condition wells.

Western Blot Profiling Analysis of Anti-IgM-Stimulated Raji Cells $1 \times 10^7$ Raji cells (ATCC, CCL-86) are seeded in 14-mL round-bottom tubes in RPMI 1640 medium (ATCC, 30-2001) containing 10% FBS (Heat-Inactivated, Gibco, 10082), and 1% Penicillin/Streptomycin (Cellgro, 30-002-CI). Serial dilutions of test compound in a final concentration of 0.3% DMSO (vehicle) are added to the cells and incubated for 90 min followed by 0.25 µg/mL anti-IgM (Southern Biotech, 9023-01) stimulation for 30 min. After stimulation, cells are spun down at 290×g for 4 min, washed once with cold phosphate-buffered saline (PBS; Cellgro, 21-030-CV) and immediately lysed with 120 µL of cold lysis buffer (50 mM Tris-HCl, pH 7.6; 150 mM NaCl; 0.1% Triton X-100; 1 mM EDTA; Protease Inhibitor Cocktail (Roche, 11697498001); and PhosSTOP (Roche, 04906837001)) for 30 min. Lysates are collected and cleared by centrifugation at 17,800×g for 15 min. Protein concentrations are measured by the BCA method (Pierce, 23227). Lysates are mixed with NuPage LDS sample buffer (Invitrogen, NP0007) and Reducing Agent (Invitrogen, NP0004), then heated at 70° C. for 10 min. 26 µg protein is loaded onto NuPage 4-12% Bis-Tris gels (Invitrogen, NP0323). Proteins are transferred to nitrocellulose membranes (Invitrogen, LC2001), blocked for 1 h in Odyssey Blocking Buffer (Li-Cor, 927-40000), and incubated at 4° C. overnight with the following antibodies diluted in Odyssey Blocking Buffer containing 0.1% Tween-20: Anti-phospho-$AKT^{T308}$ (1:500, Cell Signaling Technology, 2965), Anti-phospho-$AKT^{S473}$ (1:1,000, Cell Signaling Technology, 4060), Anti-AKT (1:2, 000, R&D Systems, MAB 2055), Anti-phospho-$PRAS40^{T246}$ (1:500, Cell Signaling Technology, 2640), anti-phospho-$GSK3\beta^{S9}$ (1:500, Cell Signaling Technology, 9336), Anti-phospho-$S6^{S240/244}$ (1:500, Cell Signaling Technology, 2215), Anti-S6 (1:1,000, Cell Signaling Technology, 2217), Anti-GAPDH (1:100,000, Advanced Immunochemical Inc, MAB6C5). Membranes are washed four times for 10 min each with TBS-T buffer (50 mM Tris-HCl, pH7.2; 150 mM NaCl; 0.1% Tween-20) and blotted with Goat anti-Mouse-IRDye680 (Li-Cor, 926-32220) and Goat anti-Rabbit-IRDye800 (Li-Cor, 926-32211) secondary antibodies in Odyssey Blocking buffer containing 0.1% Tween-20 for 60 min at room temperature. Membranes are washed four times for 10 min each with TBS-T buffer and rinsed with PBS twice. The membranes are scanned using the Odyssey Scanner (Li-Cor) and the signal intensity of each band is quantified using ImageQuant (Molecular Devices). $IC_{50}$ values are calculated based on the signal with compound treatment compared to the vehicle (DMSO) control.

Western Blot Analysis of Anti-IgM-Induced AKT Phosphorylation in Human Peripheral Blood B-Lymphocytes Human primary B-lymphocytes (B cells, AllCells, PB010) are seeded at $6 \times 10^5$ cells/well onto 48-well cluster plates (Nunc 150687) in RPMI 1640 medium (ATCC, 30-2001) containing 10% FBS (Heat Inactivated, Gibco, 10082), 1% Penicillin/Streptomycin (Cellgro, 30-002-CI), 1% L-glutamine (Cellgro, 25-015-CI), and 50 µM β-mercaptoethanol (Gibco, 21985-023). Serial dilutions of test compound in a final concentration of 0.3% DMSO (vehicle) are added to the cells and incubated for 2 h followed by 10 µg/mL anti-IgM (Southern Biotech, 9023-01) stimulation for 5 min. After stimulation, cells are centrifuged at 290×g for 4 min, washed once with cold phosphate-buffered saline (PBS; Cellgro, 21-030-CV) and immediately lysed with 40

μL of cold lysis buffer (50 mM Tris-HCl, pH 8.0, 150 mM NaCl, 1% NP-40, 0.1% SDS, 0.5% sodium deoxycholate, 1 mM EDTA, 50 mM NaF, 1 mM sodium pyrophosphate, 1 mM sodium orthovanadate, 2 mM phenylmethylsulfonyl fluoride, 10 μg/mL aprotinin, 5 μg/mL leupeptin, and 5 μg/mL pepstatin A) for 30 min. Lysates are collected and cleared by centrifugation at 17,800×g for 15 min. Lysates are mixed with NuPage LDS sample buffer (Invitrogen NP0007) and Reducing Agent (Invitrogen, NP0004), then heated at 70° C. for 10 min. The sample is loaded onto NuPage 4-12% Bis-Tris gels (Invitrogen, NP0323). Proteins are transferred to nitrocellulose membranes (Invitrogen, LC2001), blocked for 1 h in Odyssey Blocking Buffer (Li-Cor, 927-40000), and incubated at 4° C. overnight with the following antibodies diluted in Odyssey Blocking Buffer: Anti-phospho-AKT$^{T308}$ (1:200, Cell Signaling Technology, 2965), Anti-phospho-AKT$^{S473}$ (1:200, Cell Signaling Technology, 4060), Anti-AKT (1:1,000, R&D Systems, MAB 2055), and Anti-GAPDH (1:100,000, Advanced Immunochemical Inc, MAB6C5). Membranes are washed four times for 10 min each with TBS-T buffer (50 mM Tris-HCl, pH7.2; 150 mM NaCl; 0.1% Tween-20) and blotted with Goat anti-Mouse-IRDye680 (Li-Cor, 926-32220) and Goat anti-Rabbit-IRDye800 (Li-Cor, 926-32211) secondary antibodies in Odyssey Blocking buffer containing 0.1% Tween-20 for 60 min at room temperature. Membranes are washed four times for 10 min each with TBS-T buffer and rinsed with PBS twice. The membranes are scanned using the Odyssey Scanner (Li-Cor) and the signal intensity of each band is quantified using ImageQuant (Molecular Devices). $IC_{50}$ values are calculated based on the signal with compound treatment compared to the vehicle (DMSO) control.

Anti-IgM-Stimulated Raji Cell TNF-Alpha Cytokine Release Assay

Raji cells (ATCC, CCL-86) are seeded at 2×10$^5$ cells/well in 96-well cell culture cluster round-bottom plates (Corning, Costar 3790) in RPMI 1640 medium (ATCC, 30-2001) containing 10% FBS (Heat-Inactivated, Gibco, 10082) with 1% Penicillin/Streptomycin (Cellgro, 30-002-CI). Cells are treated with serially diluted compounds for 2 h at 37° C. in 5% $CO_2$. Cells are stimulated with 1 μg/mL anti-IgM antibody (Southern Biotech, 9023-01) for 4 h. Minimal signal wells are treated with commercially available PI-103 (CAS 371935-74-9) and maximal signal wells are in 0.3% DMSO, both stimulated with anti-IgM. Unstimulated cells are also included as a negative control. After treatment, culture supernatants are filtered using 96-well 0.2-μm PVDF filter plates (Corning, Costar 3504). Filtered conditioned medium is added to MSD plates (K151BHB-2) and incubated for 3 h at room temperature with agitation on a shaker (600 rpm). Plates are washed three times with phosphate-buffered saline (PBS; 137 mM NaCl, 2.7 mM KCl, 6.5 mM $Na_2HPO_4$, 1.7 mM $KH_2PO_4$) containing 0.05% Tween-20 (Bio-Rad, 161-0781). Detection Antibody Solution (Meso Scale Discovery, K151BHB-2) is added to each well and incubated for 2 h at room temperature. Plates are then washed three times with phosphate-buffered saline (PBS; 137 mM NaCl, 2.7 mM KCl, 6.5 mM $Na_2HPO_4$, 1.7 mM $KH_2PO_4$) containing 0.05% Tween-20 (Bio-Rad, 161-0781). Read Buffer T (Meso Scale Discovery, K151BHB-2) is added to each well, and then the plates are analyzed on the MSD SECTOR Imager. $IC_{50}$ values are calculated based on the signal of cells with compound treatment compared to those of the corresponding maximal and minimal signal wells.

Anti-IgM-Stimulated Human Peripheral Blood B-Lymphocytes Cytokine Release Assay

Human primary peripheral blood B cells (Negatively selected, CD 19$^+$, AllCells, PB010) are seeded at 1×10$^5$ cells/well onto 96-well microtiter cluster plates (Costar, 3790) in RPMI 1640 medium (ATCC, 30-2001) containing 10% FBS (Heat Inactivated, Gibco, 10082), 1% Penicillin/Streptomycin (Cellgro, 30-002-CI), 1% L-glutamine (Cellgro, 25-015-CI), and 50 μM β-mercaptoethanol (Gibco, 21985-0233). Serial dilutions of compound in a final concentration of 0.3% DMSO (vehicle) are added to the cells and incubated at 37° C., 5% $CO_2$ for 2 h. Duplicate wells are used for each compound concentration. Minimum signal wells received 30 μM PI-103, a pan-PI3K inhibitor. Cells in all wells are then stimulated with anti-IgM (Jackson Immunoresearch, 109-006-129) for an additional 4 h at 37° C., 5% $CO_2$. Cells are then transferred onto 96-well filter plates (Corning Costar, 3504), and supernatants collected by vacuum filtration. The supernatants are frozen at −80° C. until time of assay. According to the manufacturer's instructions, supernatants are assayed for cytokine levels using the Human Pro-inflammatory 9-Plex Tissue Culture Kit (GM-CSF, IFN-gamma, IL-10, IL-12 p70, IL-2, IL-6, IL-8, TNF-alpha; Meso Scale Discovery, K15007B-1). Briefly, supernatants are added onto pre-blocked assay plates and incubated at room temperature for 2 h with vigorous shaking at 600 rpm. Detection antibodies are then added onto the supernatants and incubated at room temperature for an additional 2 h with vigorous shaking at 600 rpm. Plates are washed three times with phosphate-buffered saline (PBS; 137 mM NaCl, 2.7 mM KCl, 6.5 mM $Na_2HPO_4$, 1.7 mM $KH_2PO_4$) containing 0.05% Tween-20 (Bio-Rad, 161-0781) and electrochemiluminescence detected using the MSD SI2400 plate reader. $IC_{50}$ values are calculated based on the calculated cytokine concentration with compound treatment minus the minimum signal compared to the DMSO vehicle control.

CpG ODN-Stimulated Human Peripheral Blood B-Lymphocytes Cytokine Release Assay

Human primary peripheral blood B-cells (Negatively selected, CD19$^+$, AllCells, PB010) are seeded at 1×10$^5$ cells/well onto 96-well microtiter cluster plates (Corning, Costar 3790) in RPMI 1640 medium (ATCC, 30-2001) containing 10% FBS (Heat Inactivated, Gibco, 10082), 1% Penicillin/Streptomycin (Cellgro, 30-002-CI), 1% L-glutamine (Cellgro, 25-015-CI), and 50 μM beta-mercaptoethanol (Gibco, 21985-023). Serial dilutions of compound in a final concentration of 0.3% DMSO (vehicle) are added to the cells and incubated at 37° C., 5% CO2 for 2 h. Duplicate wells are used for each compound concentration. Minimum signal wells received 30 μM commercially available PI-103 (CAS 371935-74-9), a pan-PI3K inhibitor. Cells in all wells are then stimulated with CpG ODN (Imgenex, IMG-2209H) for an additional 4 h at 37° C., 5% $CO_2$. Cells are then transferred onto 96-well filter plates (Corning, Costar 3504), and supernatants collected by vacuum filtration. The supernatants are frozen at −80° C. until time of assay. According to the manufacturer's instructions, supernatants are assayed for cytokine levels using the Human Pro-inflammatory 9-Plex Tissue Culture Kit (GM-CSF, IFN-gamma, IL-1 beta, IL-10, IL-12 p70, IL-2, IL-6, IL-8, TNF-alpha; Meso Scale Discovery, K15007B-1). Briefly, supernatants are added onto pre-blocked assay plates and incubated at room temperature for 2 h with vigorous shaking at 600 rpm. Detection antibodies are then added onto the supernatants and incubated at room temperature for an additional 2 h with vigorous shaking at 600 rpm. Plates are washed three times with phosphate-buffered saline (PBS; 137 mM NaCl, 2.7 mM KCl, 6.5 mM $Na_2HPO_4$, 1.7 mM $KH_2PO_4$) containing 0.05% Tween-20 (Bio-Rad, 161-0781) and electrochemiluminescence detected using the MSD SI2400 plate reader. $IC_{50}$ values are calculated based on the calculated cytokine concentration with compound treatment minus the minimum signal compared to the DMSO vehicle control.

Anti-CD3-Mediated Human Peripheral Blood T-Lymphocytes Cytokine Release Assay

Human peripheral blood mononuclear cells (PBMCs) from healthy human donors are isolated using a sodium diatrizoate polysucrose gradient (Accuspin System Histopaque-1077, Sigma-Aldrich, A7054). Cells are then negatively selected according to manufacturer's instructions using the EasySep Human T cell Enrichment kit (Stem Cell Technologies, 19051). Cells are more than 95% pure. $CD3^+$ T cells are seeded at $1\times10^5$ cells/well onto 96-well microtiter cluster plates (Corning, Costar 3790) in RPMI 1640 medium (ATCC, 30-2001) containing 10% FBS (Heat Inactivated, Gibco, 10082), 1% Penicillin/Streptomycin (Cellgro, 30-002-CI), 1% L-glutamine (Cellgro, 25-015-CI), and 50 µM beta-mercaptoethanol (Gibco, 21985-023). Serial dilutions of compound in a final concentration of 0.3% DMSO (vehicle) are added to the cells and incubated at 37° C., 5% $CO_2$ for 2 h. Duplicate wells are used for each compound concentration. Minimum signal wells received 30 µM commercially available PI-103 (CAS 371935-74-9), a pan-PI3K inhibitor. Cells in all wells are then seeded onto anti-human CD3-coated 96-well microtiter plates (BD Biosciences, 354725) for an additional 4 h at 37° C., 5% $CO_2$. Cells are then transferred onto 96-well filter plates (Corning, Costar 3504), and supernatants collected by vacuum filtration. The supernatants are frozen at −80° C. until time of assay. According to the manufacturer's instructions, supernatants are assayed for cytokine levels using the Human TH 1/TH2 10-Plex Tissue Culture Kit (IFN-gamma, IL-1beta, IL-10, IL-12 p70, IL-13, IL-2, IL-4, IL-5, IL-8, TNF-alpha; Meso Scale Discovery, K15010B-1). Briefly, supernatants are added onto pre-blocked assay plates and incubated at room temperature for 2 h with vigorous shaking at 600 rpm. Detection antibodies are then added onto the supernatants and incubated at room temperature for an additional 2 h with vigorous shaking at 600 rpm. Plates are washed three times with phosphate-buffered saline (PBS; 137 mM NaCl, 2.7 mM KCl, 6.5 mM $Na_2HPO_4$, 1.7 mM $KH_2PO_4$) containing 0.05% Tween-20 (Bio-Rad, 161-0781) and electrochemiluminescence detected using the MSD SI2400 plate reader. $IC_{50}$ values are calculated based on the calculated cytokine concentration with compound treatment minus the minimum signal compared to the DMSO vehicle control.

LPS-Stimulated Peripheral Blood Mononuclear Cell Cytokine Release Assay

Human primary peripheral blood mononuclear cells (PBMC, AllCells, PB001) are seeded at $2\times10^5$ cells/well onto 96-well microtiter cluster plates (Corning, Costar 3790) in RPMI 1640 medium (ATCC, 30-2001) containing 10% FBS (Heat Inactivated, Gibco, 10082), 1% Penicillin/Streptomycin (Cellgro, 30-002-CI), 1% L-glutamine (Cellgro, 25-015-CI), and 50 µM β-mercaptoethanol (Gibco, 21985-023). Serial dilutions of compound in a final concentration of 0.3% DMSO (vehicle) are added to the cells and incubated at 37° C., 5% $CO_2$ for 2 h. Duplicate wells are used for each compound concentration. Minimum signal wells received 30 µM commercially available PI-103 (CAS 371935-74-9), a pan-PI3K inhibitor. Cells in all wells are then stimulated with lipopolysaccharide (LPS, Sigma, L4391) for an additional 6 h at 37° C., 5% $CO_2$. Cells are then transferred onto 96-well filter plates (Corning, Costar 3504), and supernatants collected by vacuum filtration. The supernatants are frozen at −80° C. until time of assay. According to the manufacturer's instructions, supernatants are assayed for cytokine levels using the Human Pro-inflammatory 9-Plex Tissue Culture Kit (GM-CSF, IFN-gamma, IL-1beta, IL-10, IL-12 p70, IL-2, IL-6, IL-8, TNF-alpha; Meso Scale Discovery, K15007B-1). Briefly, supernatants, either undiluted or diluted 1:2, are added onto pre-blocked assay plates and incubated at room temperature for 2 hours with vigorous shaking at 600 rpm. Detection antibodies are then added onto the supernatants and incubated at room temperature for an additional 2 h with vigorous shaking at 600 rpm. Plates are washed three times with phosphate-buffered saline (PBS; 137 mM NaCl, 2.7 mM KCl, 6.5 mM $Na_2HPO_4$, 1.7 mM $KH_2PO_4$) containing 0.05% Tween-20 (Bio-Rad, 161-0781) and electrochemiluminescence detected using the MSD SI2400 plate reader. $IC_{50}$ values are calculated based on the calculated cytokine concentration with compound treatment minus the minimum signal compared to the DMSO vehicle control.

Primary Human B- and T-Lymphocyte BrdU Proliferation Assay

Human primary B-lymphocytes (B cells, AllCells, PB010) are seeded at $1\times10^5$ cells/well onto 96-well microtiter cluster plates (Corning, Costar 3790) and human primary T-lymphocytes (T cells, AllCells, PB009-1) are seeded at $2\times10^5$ cells/well onto anti-human CD3-coated 96-well microtiter plates (BD Biosciences, 354725) in RPMI-1640 medium (ATCC, 30-2001) containing 10% FBS (Heat Inactivated, Gibco, 10082), 1% Penicillin/Streptomycin (Cellgro, 30-002-CI), 1% L-glutamine (Cellgro, 25-015-CI), and 50 µM beta-mercaptoethanol (Gibco, 21985-023). The human primary B cells are stimulated with either anti-human IgM (Jackson Immunoresearch, 109-006-129) at a final concentration of 25 µg/mL or with CpG ODN (Imgenex, IMG-2209H) at a final concentration of 2 µg/mL. Both B and T cells are treated immediately after stimulation with a serial dilution of compound in medium (containing a final concentration of 0.3% DMSO). Triplicate wells are used for each compound concentration in B cells, and duplicate wells are used for each compound concentration in T cells. The control wells received 0.3% DMSO media. The minimum signal wells received 30 µM of commercially available PI-103 (CAS 371935-74-9), a pan-PI3K inhibitor. The cultures are incubated at 37° C., 5% $CO_2$ for 72 h (B cells) or 96 h (T cells). To assay the cells, they are labeled with 20 µM bromodeoxyuridine (BrdU, Sigma, B5002-500MG), transferred to 96-well filter plates (Costar 3504), and then fixed with FixDenat solution (70% ethanol+0.1M NaOH). Anti-BrdU-POD (1:2,000; Roche, 11585860001) conjugate is added to the cells, after which the plates are washed 3 times with phosphate-buffered saline (PBS; 137 mM NaCl, 2.7 mM KCl, 6.5 mM $Na_2HPO_4$, 1.7 mM $KH_2PO_4$). Substrate solution made from 1 part peroxide (Thermo Scientific, 37075A) and 1 part luminol (Thermo Scientific, 37075B) is added, and the plates are read for luminescence (0.1 s) using the Victor Wallac luminometer. $IC_{50}$ values are calculated based on the cell proliferation with compound treatment minus the minimum signal compared to the DMSO vehicle control.

MC/9 Mouse Mast Cell β-Hexosaminidase Degranulation Assay

MC/9 cells (ATCC, CRL-8306) are seeded at $1\times10^6$ cells/mL onto tissue-culture flasks (Nunc, 144903) in DMEM (Cellgro, 10-013-CV) containing 10% FBS (Heat-Inactivated, Gibco, 10082), 1.5 g/L sodium bicarbonate, 0.05 mM 2-mercaptoethanol, 10% Rat T-STIM (BD, 354115), and 1% Penicillin/Streptomycin (Cellgro, 30-002-CI). Cells are incubated with 200 ng/mL anti-DNP IgE (Sigma, D8406) overnight at 37° C. in 5% $CO_2$. Cells are washed twice with Tyrode's buffer (135 mM NaCl, 5 mM KCl, 5.6 mM glucose, 1.8 mM $CaCl_2$. 1 mM $MgCl_2$, 20 mM HEPES, and 0.5 mg/mL BSA; pH 7.3) and seeded at $2\times10^5$ cells/well in 96-well microtiter plates (Costar, 3904) in 70 µL of Tyrode's buffer. 30 µL of serially diluted test compounds in Tyrode's buffer with a final concentration of 0.3% DMSO (vehicle) are added to the cells and incubated for 75 min. Cells are stimulated with 200 ng/mL DNP-HSA (Sigma, A6661) for 45 min. Background wells are cells in 0.3% DMSO without DNP-HSA stimulation. Minimal signal wells are treated with commercially available PI-103 (CAS 371935-74-9), 10 µM) and maximal signal wells are in 0.3% DMSO, both stimulated with DNP-HSA. The final volume per well is 110 µL. After stimulation, cells are spun down at 400×g for 4 min. 50 µL of supernatant is carefully collected and transferred to a 96-well plate (Nunc, 260895) and incubated with 75 µL of 1 mM p-nitrophenyl acetyl-D-glucosamine (Sigma, N9376) in citrate buffer (pH 4.5) for 2 h at 37° C. The reaction is stopped by adding 75 µL of 2 M NaOH. Wells are measured for absorbance at wavelength of 405 nm with correction at 630 nm using a spectrophotometer (Molecular Devices, SpectraMax Plus). The average background well values are subtracted from all wells. $IC_{50}$ values are calculated based on the absorbance of cells with compound treatment compared to those of the corresponding maximal and minimal signal wells.

Example 3

Pharmacodynamic Xenograft Tumor Models

Female and male athymic nude mice (NCr) 5-8 weeks of age and weighing approximately 20-25 g are used in the following models. Prior to initiation of a study, the animals are allowed to acclimate for a minimum of 48 h. During these studies, animals are provided food and water ad libitum and housed in a room conditioned at 70-75° F. and 60% relative humidity. A 12 h light and 12 h dark cycle is maintained with automatic timers. All animals are examined daily for compound-induced or tumor-related deaths.

Tumor weight (TW) in the above models is determined by measuring perpendicular diameters with a caliper, using the following formula:

Tumor Weight(mg)=[tumor volume=length(mm)× width$^2$(mm$^2$)]/2

These data are recorded and plotted on a tumor weight vs. days post-implantation line graph and presented graphically as an indication of tumor growth rates. Percent inhibition of tumor growth (TGI) is determined with the following formula:

$$\left[1-\left(\frac{(X_f - X_0)}{(Y_f - X_0)}\right)\right]*100$$

where:
X$_0$=average TW of all tumors on group day
X$_f$=TW of treated group on Day f
Y$_f$=TW of vehicle control group on Day f
If tumors regress below their starting sizes, then the percent tumor regression is determined with the following formula:

$$\left(\frac{X_0 - X_f}{X_0}\right)*100$$

Tumor size is calculated individually for each tumor to obtain a mean±SEM value for each experimental group. Statistical significance is determined using the 2-tailed Student's t-test (significance defined as P<0.05).

The foregoing invention has been described in some detail by way of illustration and example, for purposes of clarity and understanding. The invention has been described with reference to various specific embodiments and techniques. However, it should be understood that many variations and modifications may be made while remaining within the spirit and scope of the invention. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled. All patents, patent applications and publications cited in this application are hereby incorporated by reference in their entirety for all purposes to the same extent as if each individual patent, patent application or publication were so individually denoted.

What is claimed is:
1. A compound of Formula II-B1 or II-B2

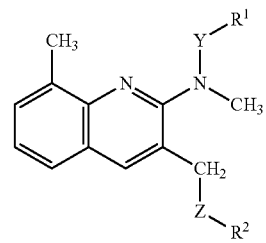

II-B1

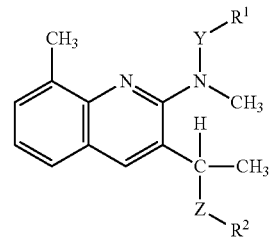

II-B2 or a stereoisomer or mixture of stereoisomers thereof, optionally as a pharmaceutically acceptable salt thereof, wherein:

Y is absent or is a ($C_1$-$C_6$)alkylene wherein up to two carbon atoms of the ($C_1$-$C_6$)alkylene are replaced by O, NH, N—($C_1$-$C_6$)alkyl, —NH—(C=O)—, —N($C_1$-$C_6$) alkyl-(C=O)—, or —(C=O)—;

Z is absent or is NH, N($C_1$-$C_6$)alkyl, NH($C_1$-$C_6$)alkylene, —NH—(C=O)—, —N($C_1$-$C_6$)alkyl-(C=O)—, S, SO, $SO_2$, or O;

$R^1$ is halo, hydroxy, cyano, optionally substituted aryl, optionally substituted heteroaryl, optionally substituted heterocycloalkyl, ($C_1$-$C_6$)alkyl, ($C_1$-$C_6$)alkoxy, ($C_1$-$C_6$)

alkyl-OH, NH₂, —NH—(C₁-C₆)alkyl, —NH—((C₁-C₆)alkyl)₂, —NH—(C=O)—R⁵, —(C=O)NR⁶R⁷, or —NH—(SO₂)—R⁸;

R² is NH₂, optionally substituted cycloalkyl, optionally substituted heterocycloalkyl, or optionally substituted heteroaryl,

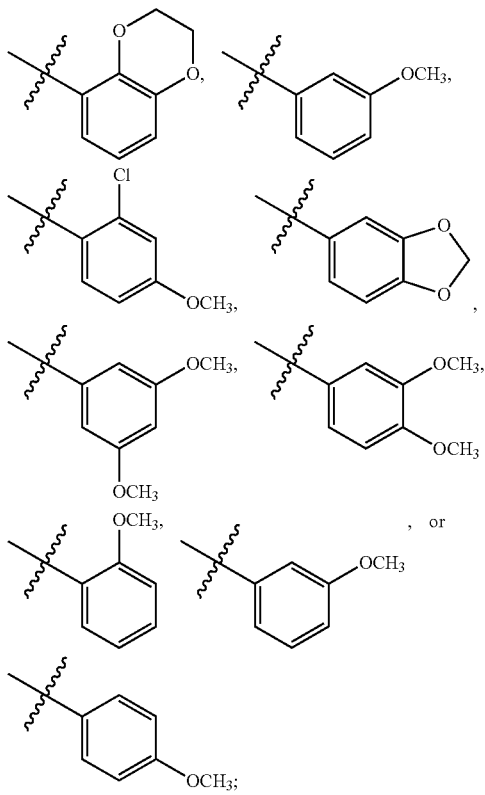

R⁵ is H, (C₁-C₆)alkyl, optionally substituted cycloalkyl, optionally substituted heterocycloalkyl, optionally substituted aryl, or optionally substituted heteroaryl;

R⁶ and R⁷ are each independently H, (C₁-C₆)alkyl, optionally substituted cycloalkyl, optionally substituted heterocycloalkyl, optionally substituted aryl, optionally substituted heteroaryl, or R⁶ and R⁷, together with the atoms to which they are attached, can be taken together to form an optionally substituted 3, 4, 5, 6, or 7-membered ring;

R⁸ is (C₁-C₆)alkyl, optionally substituted cycloalkyl, optionally substituted heterocycloalkyl, optionally substituted aryl, or optionally substituted heteroaryl.

2. The compound of claim 1, wherein Z is absent or is NH, N(C₁-C₆)alkyl, —NH—(C=O)—, —N(C₁-C₆)alkyl-(C=O)—, O, or S.

3. The compound of claim 2, wherein Y is (C₁-C₆) alkylene, wherein up to two carbon atoms of the (C₁-C₆) alkylene are replaced by NH, N(C₁-C₆)alkyl, —NH—(C=O)—, —N(C₁-C₆)alkyl—(C=O)—, or —(C=O)—.

4. The compound of claim 1, wherein Z is absent or is —NH—, —NH—(C=O)—, or S.

5. The compound of claim 4, wherein R¹ is selected from the group consisting of

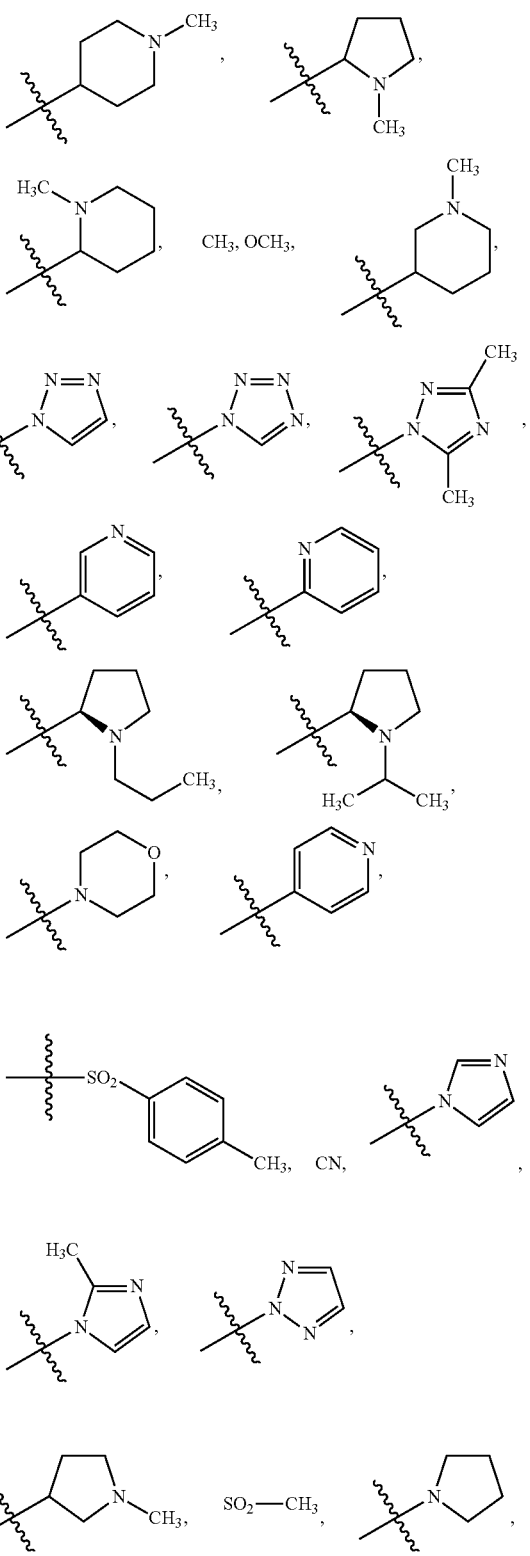

NH₂, and OH.

6. The compound of claim 5, wherein R² is NH₂, purinyl, pyrazinyl, pyrazolopyrimidinyl, benzodioxinyl, phenyl, morpholinyl, oxadiazolyl, cyclopropyl, or pyridinyl, any of which may be optionally substituted.

7. The compound of claim 6, wherein R² is NH₂,

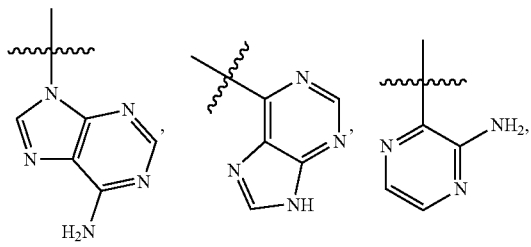

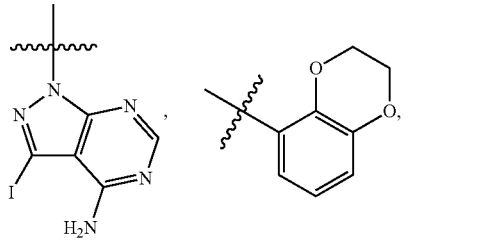

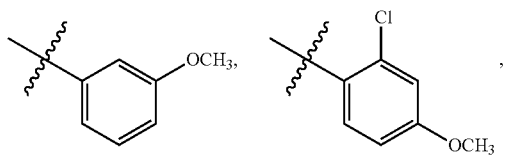

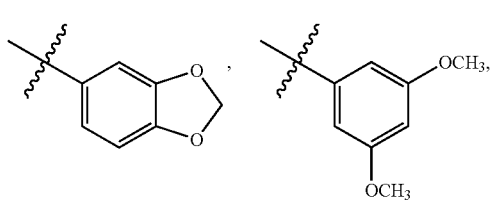

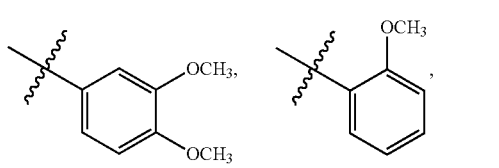

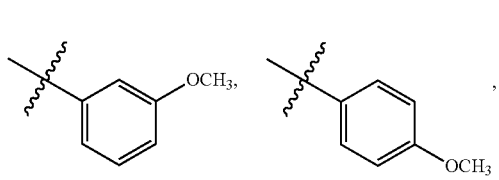

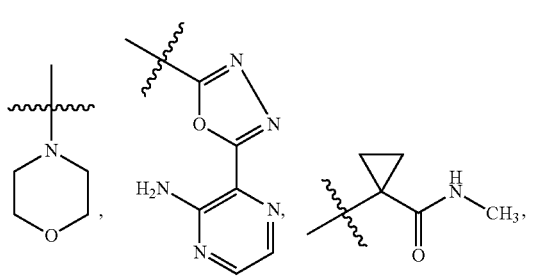

-continued

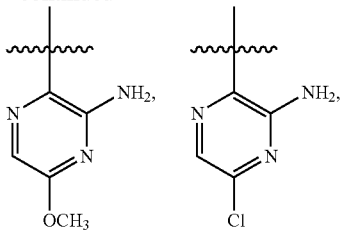

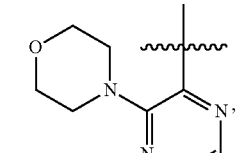

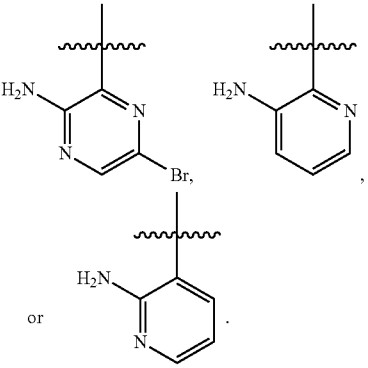

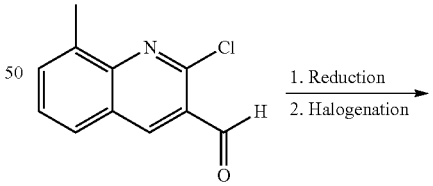

, or

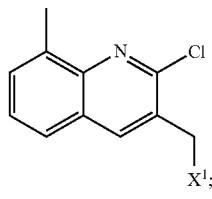

.

8. A pharmaceutical formulation comprising a compound of claim 1 and a pharmaceutically acceptable carrier.

9. A method of inhibiting PI3K delta comprising contacting the PI3K delta with an effective amount of a compound of claim 1.

10. A process for making a compound of Formula II-B, comprising:

(a) converting a compound of formula II-1 to a compound of formula II-2 via reduction to the alcohol and conversion of the alcohol to the halide, wherein X¹ is halo (b) converting a compound of formula II-2 to a compound of formula II-3 via azide formation and subsequent reduction

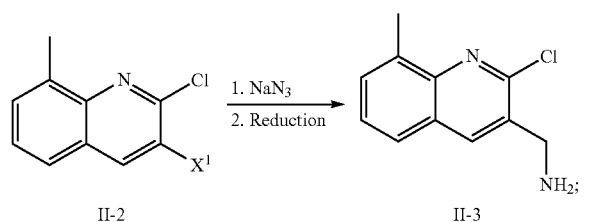

II-2　　II-3

(c) converting a compound of formula II-3 to a compound of formula II-4 via reaction with $R^2$—$X^2$, wherein $X^2$ is halo

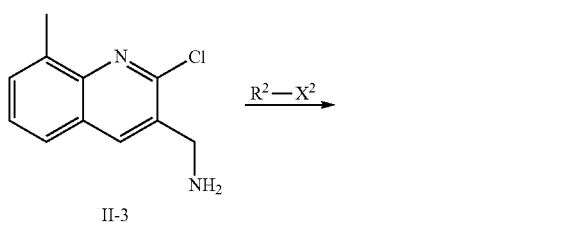

II-3 and (d) converting a compound of formula II-4 to a compound of formula II-B via reaction with $CH_3NH$—Y—$R^1$;

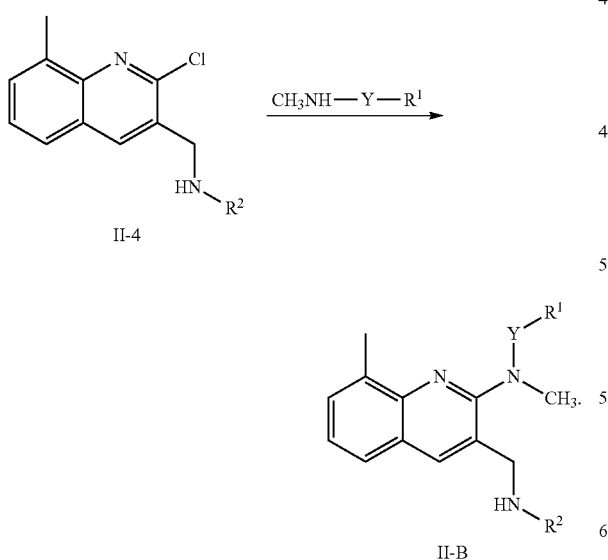

II-4

II-B

11. A process for making a compound of Formula II-A, comprising:

(a) converting the carboxylic acid of formula II-5 to an amide of formula II-6

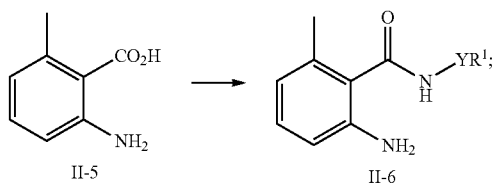

II-5　　II-6

(b) converting a compound of formula II-6 to a compound of formula II-7 via treatment with 2-haloacetyl chloride, wherein $X^1$ is halo

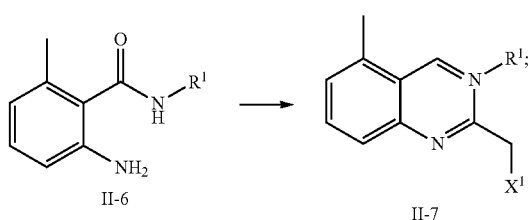

II-6　　II-7

(c) converting a compound of formula II-7 to a compound of formula II-8 via via azide formation and subsequent reduction

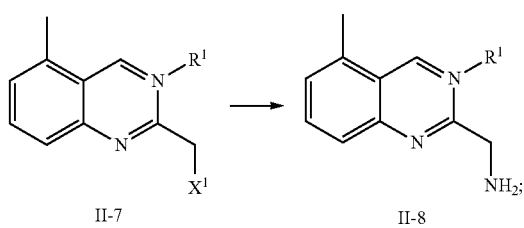

II-7　　II-8

(d) converting a compound of formula II-8 to a compound of formula II-A via reaction with $R^2$—$CO_2H$

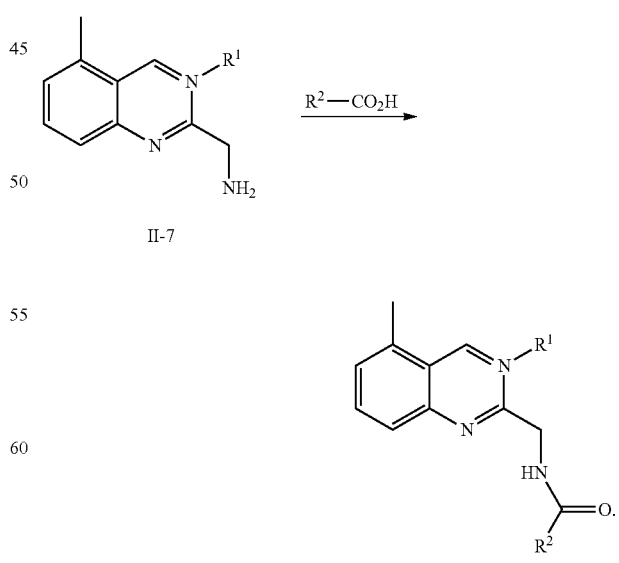

II-7

II-A

12. A compound which is:

| Compound | Structure | Name |
|---|---|---|
| 1 | 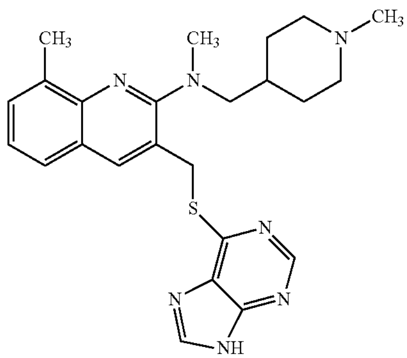 [SMILES: Cc1cccc2cc(CSc3ncnc4[nH]cnc34)c(N(C)CC3CCN(C)CC3)nc12] | N,8-dimethyl-N-[(1-methylpiperidin-4-yl)methyl]-3-[(9H-purin-6-ylthio)methyl]quinolin-2-amine |
| 2 | 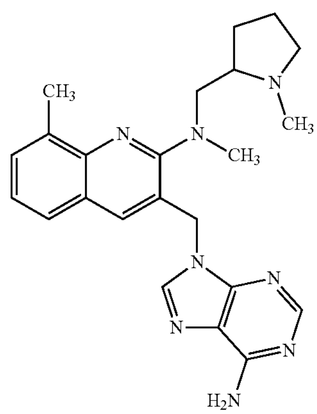 [SMILES: Cc1cccc2cc(Cn3cnc4c(N)ncnc43)c(N(C)CC3CCCN3C)nc12] | 3-[(6-amino-9H-purin-9-yl)methyl]-N,8-dimethyl-N-[(1-methylpyrrolidin-2-yl)methyl]quinolin-2-amine |
| 3 | 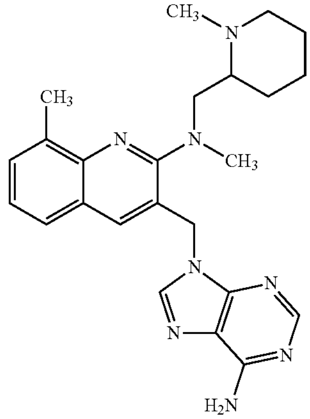 [SMILES: Cc1cccc2cc(Cn3cnc4c(N)ncnc43)c(N(C)CC3CCCCN3C)nc12] | 3-[(6-amino-9H-purin-9-yl)methyl]-N,8-dimethyl-N-[(1-methylpiperidin-2-yl)methyl]quinolin-2-amine |

-continued

| Compound | Structure | Name |
|---|---|---|
| 4 | 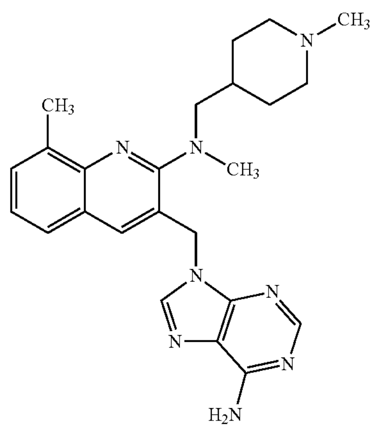 [SMILES: Cc1cccc2cc(Cn3cnc4c(N)ncnc43)c(N(C)CC3CCN(C)CC3)nc12] | 3-[(6-amino-9H-purin-9-yl)methyl]-N,8-dimethyl-N-[(1-methylpiperidin-4-yl)methyl]quinolin-2-amine |
| 5 | 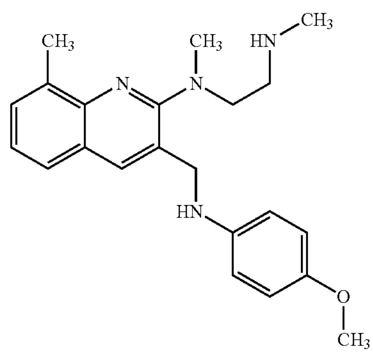 [SMILES: CNCCN(C)c1nc2c(C)cccc2cc1CNc1ccc(OC)cc1] | N,N'-dimethyl-N-[8-methyl-3-({[4-(methyloxy)phenyl]amino}methyl)quinolin-2-yl]ethane-1,2-diamine |
| 21 | 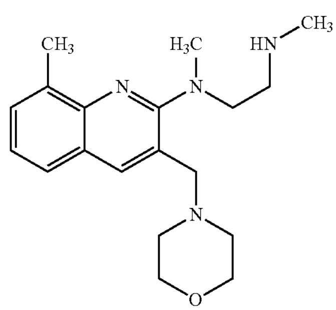 [SMILES: CNCCN(C)c1nc2c(C)cccc2cc1CN1CCOCC1] | N,N'-dimethyl-N-[8-methyl-3-(morpholin-4-ylmethyl)quinolin-2-yl]ethane-1,2-diamine |
| 22 | 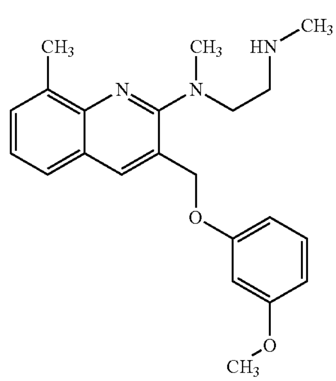 [SMILES: CNCCN(C)c1nc2c(C)cccc2cc1COc1cccc(OC)c1] | N,N'-dimethyl-N-[8-methyl-3-({[3-(methyloxy)phenyl]oxy}methyl)quinolin-2-yl]ethane-1,2-diamine |

| Compound | Structure | Name |
|---|---|---|
| 23 | 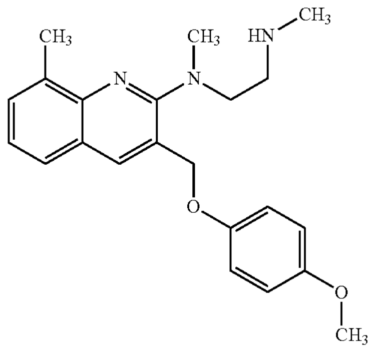 [SMILES: CNCCN(C)c1nc2c(C)cccc2cc1COc1ccc(OC)cc1] | N,N'-dimethyl-N-[8-methyl-3-({[4-(methyloxy)phenyl]oxy}methyl)quinolin-2-yl]ethane-1,2-diamine |
| 24 | 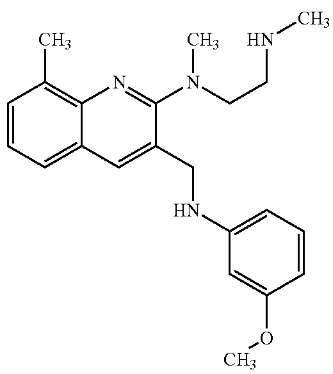 [SMILES: CNCCN(C)c1nc2c(C)cccc2cc1CNc1cccc(OC)c1] | N,N'-dimethyl-N-[8-methyl-3-({[3-(methyloxy)phenyl]amino}methyl)quinolin-2-yl]ethane-1,2-diamine |
| 25 | 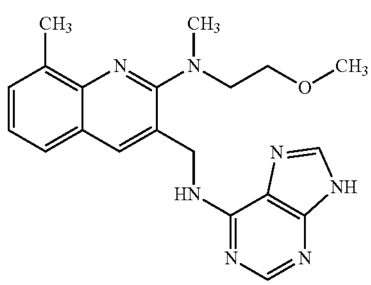 [SMILES: COCCN(C)c1nc2c(C)cccc2cc1CNc1ncnc2[nH]cnc12] | N,8-dimethyl-N-[2-(methyloxy)ethyl]-3-[(9H-purin-6-ylamino)methyl]quinolin-2-amine |
| 26 | 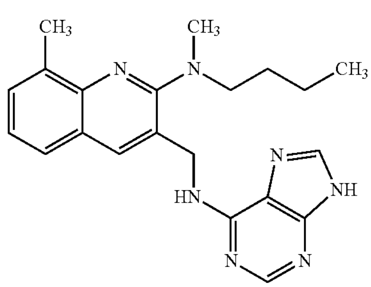 [SMILES: CCCCN(C)c1nc2c(C)cccc2cc1CNc1ncnc2[nH]cnc12] | N-butyl-N,8-dimethyl-3-[(9H-purin-6-ylamino)methyl]quinolin-2-amine |

| Compound | Structure | Name |
|---|---|---|
| 28 | 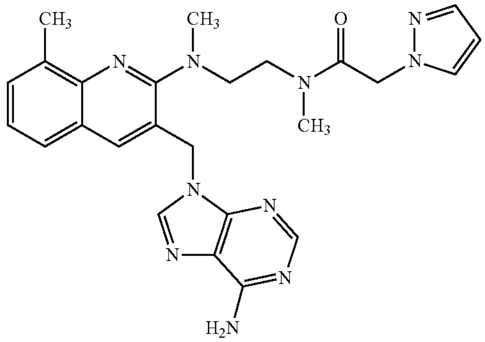 [SMILES: Cc1cccc2cc(Cn3cnc4c(N)ncnc43)c(N(C)CCN(C)C(=O)Cn3cccn3)nc12] | N-{2-[{3-[(6-amino-9H-purin-9-yl)methyl]-8-methylquinolin-2-yl}(methyl)amino]ethyl}-N-methyl-2-(1H-pyrazol-1-yl)acetamide |
| 29 | 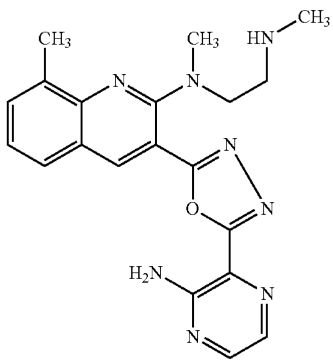 [SMILES: CNCCN(C)c1nc2c(C)cccc2cc1-c1nnc(-c2nccnc2N)o1] | N-{3-[5-(3-aminopyrazin-2-yl)-1,3,4-oxadiazol-2-yl]-8-methylquinolin-2-yl}-N,N'-dimethylethane-1,2-diamine |
| 30 | 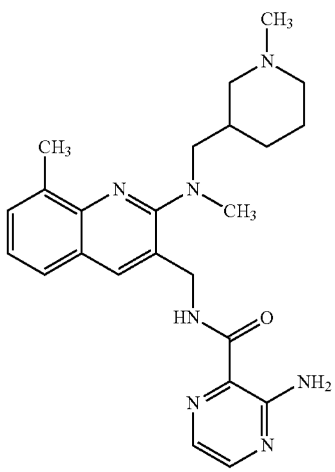 [SMILES: Cc1cccc2cc(CNC(=O)c3nccnc3N)c(N(C)CC3CCCN(C)C3)nc12] | 3-amino-N-[(8-methyl-2-{methyl[(1-methylpiperidin-3-yl)methyl]amino}quinolin-3-yl)methyl]pyrazine-2-carboxamide |
| 31 | 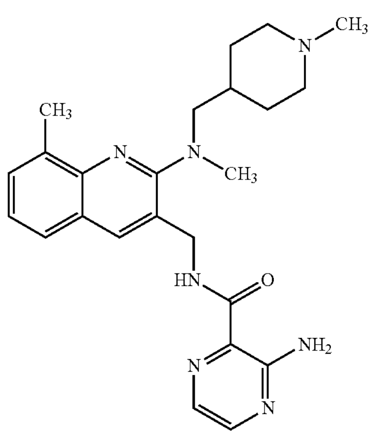 [SMILES: Cc1cccc2cc(CNC(=O)c3nccnc3N)c(N(C)CC3CCN(C)CC3)nc12] | 3-amino-N-[(8-methyl-2-{methyl[(1-methylpiperidin-4-yl)methyl]amino}quinolin-3-yl)methyl]pyrazine-2-carboxamide |

-continued

| Compound | Structure | Name |
|---|---|---|
| 32 | 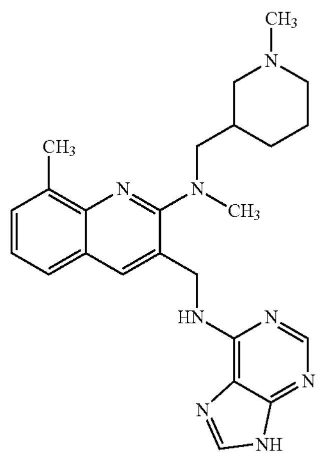 [SMILES: Cc1cccc2cc(CNc3ncnc4[nH]cnc34)c(N(C)CC3CCCN(C)C3)nc12] | N,8-dimethyl-N-[(1-methylpiperidin-3-yl)methyl]-3-[(9H-purin-6-ylamino)methyl]quinolin-2-amine |
| 33 | 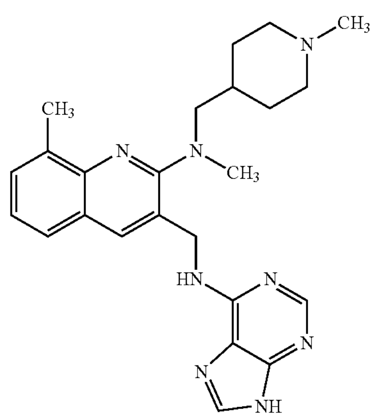 [SMILES: Cc1cccc2cc(CNc3ncnc4[nH]cnc34)c(N(C)CC3CCN(C)CC3)nc12] | N,8-dimethyl-N-[(1-methylpiperidin-4-yl)methyl]-3-[(9H-purin-6-ylamino)methyl]quinolin-2-amine |
| 34 | 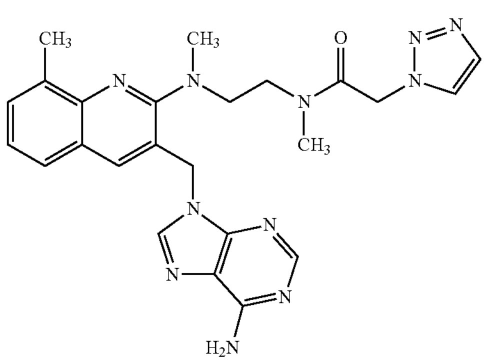 [SMILES: Cc1cccc2cc(Cn3cnc4c(N)ncnc43)c(N(C)CCN(C)C(=O)Cn3ccnn3)nc12] | N-{2-[{3-[(6-amino-9H-purin-9-yl)methyl]-8-methylquinolin-2-yl}(methyl)amino]ethyl}-N-methyl-2-(1H-1,2,3-triazol-1-yl)acetamide |
| 35 | 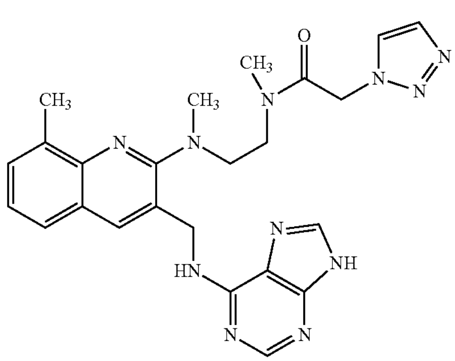 [SMILES: Cc1cccc2cc(CNc3ncnc4[nH]cnc34)c(N(C)CCN(C)C(=O)Cn3ccnn3)nc12] | N-methyl-N-[2-(methyl{8-methyl-3-[(9H-purin-6-ylamino)methyl]quinolin-2-yl}amino)ethyl]-2-(1H-1,2,3-triazol-1-yl)acetamide |

| Compound | Structure | Name |
|---|---|---|
| 36 | 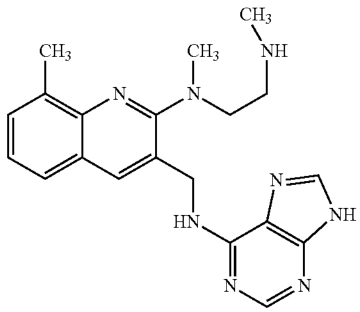 [SMILES: CNCCN(C)c1nc2c(C)cccc2cc1CNc1ncnc2[nH]cnc12] | N,N'-dimethyl-N-{8-methyl-3-[(9H-purin-6-ylamino)methyl]quinolin-2-yl}ethane-1,2-diamine |
| 38 | 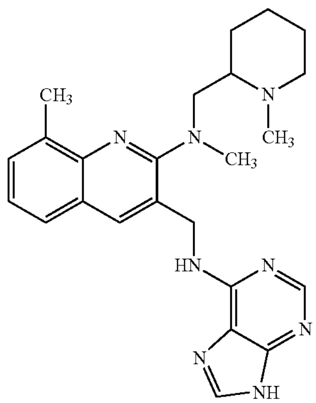 [SMILES: Cc1cccc2cc(CNc3ncnc4[nH]cnc34)c(N(C)CC3CCCCN3C)nc12] | N,8-dimethyl-N-[(1-methylpiperidin-2-yl)methyl]-3-[(9H-purin-6-ylamino)methyl]quinolin-2-amine |
| 39 | 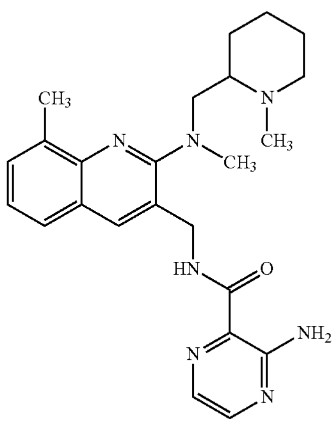 [SMILES: Cc1cccc2cc(CNC(=O)c3nccnc3N)c(N(C)CC3CCCCN3C)nc12] | 3-amino-N-[(8-methyl-2-{methyl [(1-methylpiperidin-2-yl)methyl]amino}quinolin-3-yl)methyl]pyrazine-2-carboxamide |
| 40 | 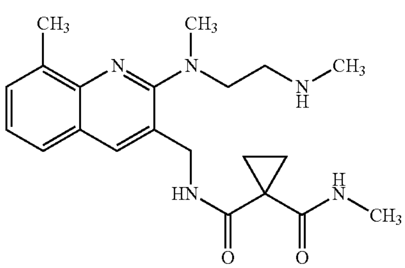 [SMILES: CNCCN(C)c1nc2c(C)cccc2cc1CNC(=O)C1(C(=O)NC)CC1] | N-methyl-N'-[(8-methyl-2-{methyl[2-(methylamino)ethyl]amino}quinolin-3-yl)methyl]cyclopropane-1,1-dicarboxamide |

-continued

| Compound | Structure | Name |
|---|---|---|
| 42 | 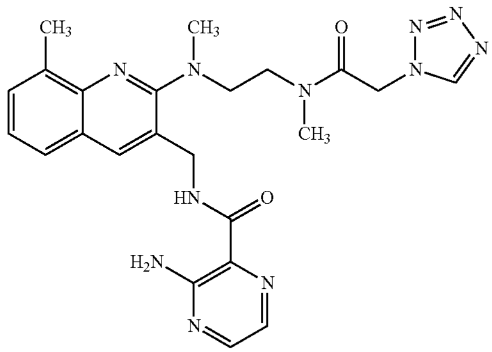 [SMILES: Cc1cccc2cc(CNC(=O)c3nccnc3N)c(N(C)CCN(C)C(=O)Cn3cnnn3)nc12] | 3-amino-N-{[8-methyl-2-(methyl{2-[methyl(1H-tetrazol-1-ylacetyl)amino]ethyl}amino)quinolin-3-yl]methyl}pyrazine-2-carboxamide |
| 43 | 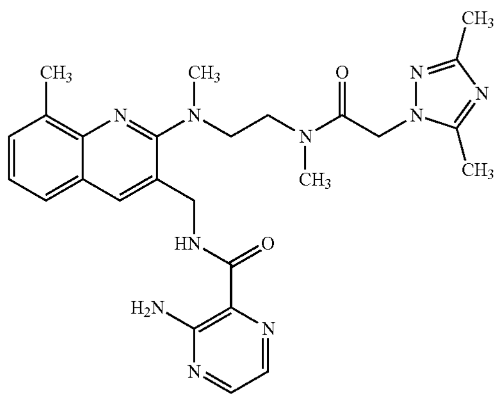 [SMILES: Cc1nc(C)n(CC(=O)N(C)CCN(C)c2nc3c(C)cccc3cc2CNC(=O)c2nccnc2N)n1] | 3-amino-N-({2-[(2-{[(3,5-dimethyl-1H-1,2,4-triazol-1-ylacetyl](methyl)amino}ethyl)(methyl)amino]-8-methylquinolin-3-yl}methyl)pyrazine-2-carboxamide |
| 46 | 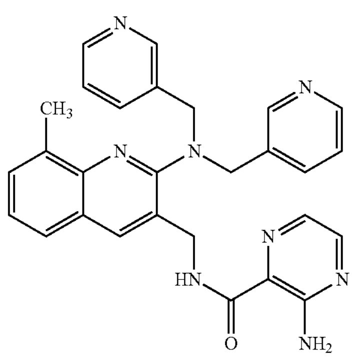 [SMILES: Cc1cccc2cc(CNC(=O)c3nccnc3N)c(N(Cc3cccnc3)Cc3cccnc3)nc12] | 3-amino-N-({2-[bis(pyridin-3-ylmethyl)amino]-8-methylquinolin-3-yl}methyl)pyrazine-2-carboxamide |
| 47 | 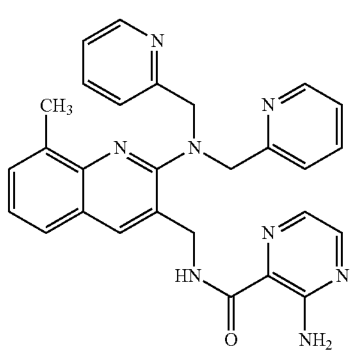 [SMILES: Cc1cccc2cc(CNC(=O)c3nccnc3N)c(N(Cc3ccccn3)Cc3ccccn3)nc12] | 3-amino-N-({2-[bis(pyridin-2-ylmethyl)amino]-8-methylquinolin-3-yl}methyl)pyrazine-2-carboxamide |

-continued

| Compound | Structure | Name |
|---|---|---|
| 49 | 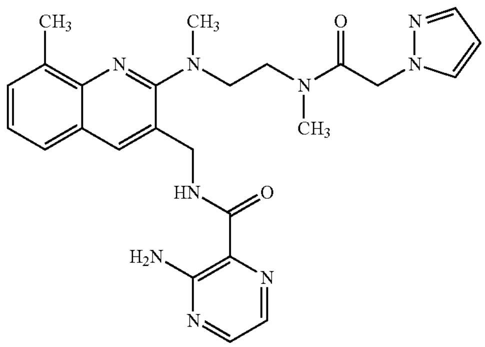 [SMILES: Cc1cccc2cc(CNC(=O)c3nccnc3N)c(N(C)CCN(C)C(=O)Cn3cccn3)nc12] | 3-amino-N-{[8-methyl-2-(methyl{2-[methyl(1H-pyrazol-1-ylacetyl)amino]ethyl}amino)quinolin-3-yl]methyl}pyrazine-2-carboxamide |
| 51 | 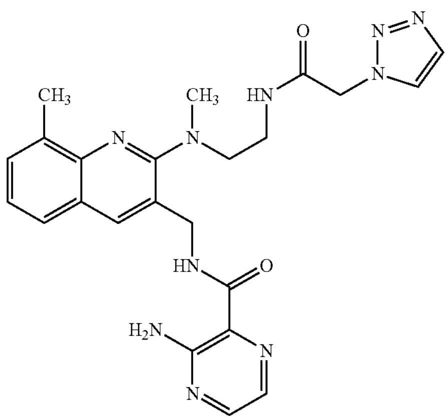 [SMILES: Cc1cccc2cc(CNC(=O)c3nccnc3N)c(N(C)CCNC(=O)Cn3ccnn3)nc12] | 3-amino-N-{[8-methyl-2-(methyl{2-[(1H-1,2,3-triazol-1-ylacetyl)amino]ethyl}amino)quinolin-3-yl]methyl}pyrazine-2-carboxamide |
| 67 | 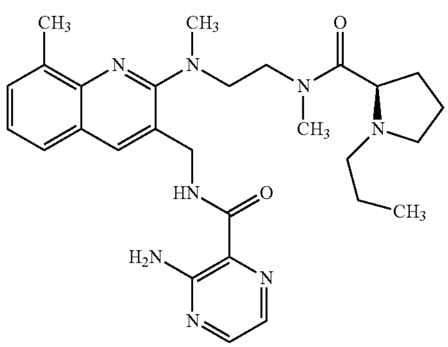 [SMILES: CCCN1CCC[C@@H]1C(=O)N(C)CCN(C)c1nc2c(C)cccc2cc1CNC(=O)c1nccnc1N] | 3-amino-N-{[8-methyl-2-(methyl{2-[methyl(1-propyl-D-proly)amino]ethyl}amino)quinolin-3-yl]methyl}pyrazine-2-carboxamide |
| 68 | 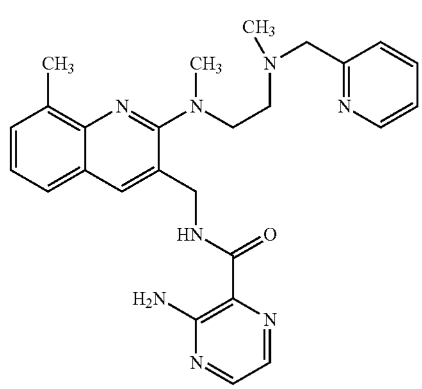 [SMILES: Cc1cccc2cc(CNC(=O)c3nccnc3N)c(N(C)CCN(C)Cc3ccccn3)nc12] | 3-amino-N-{[8-methyl-2-(methyl{2-[methyl(pyridin-2-ylmethy)amino]ethyl}amino)quinolin-3-yl]methyl}pyrazine-2-carboxamide |

-continued

| Compound | Structure | Name |
|---|---|---|
| 73 | 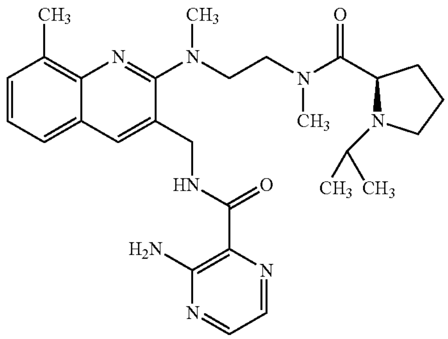 [SMILES: Cc1cccc2cc(CNC(=O)c3nccnc3N)c(N(C)CCN(C)C(=O)[C@H]3CCCN3C(C)C)nc12] | 3-amino-N-({8-methyl-2-[methyl(2-{methyl[1-(1-methylethyl)-D-prolyl] amino}ethyl)amino]quinolin-3-yl}methyl)pyrazine-2-carboxamide |
| 76 | 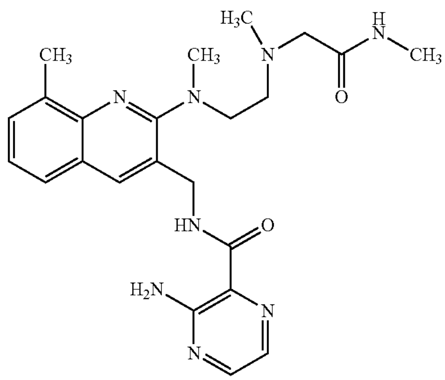 [SMILES: CNC(=O)CN(C)CCN(C)c1nc2c(C)cccc2cc1CNC(=O)c1nccnc1N] | 3-amino-N-({8-methyl-2- [methyl(2-{methyl [2-(methylamino)-2-oxoethyl]amino}ethyl)amino]quinolin-3-yl)methyl)pyrazine-2-carboxamide |
| 77 | 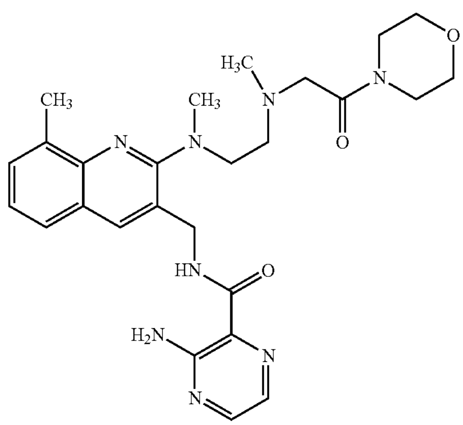 [SMILES: Cc1cccc2cc(CNC(=O)c3nccnc3N)c(N(C)CCN(C)CC(=O)N3CCOCC3)nc12] | 3-amino-N-{[8-methyl-2-(methyl{2-[methyl(2-morpholin-4-yl-2-oxoethyl]amino}ethyl)amino]quinolin-3-yl]methyl}pyrazine-2-carboxamide |
| 78 | 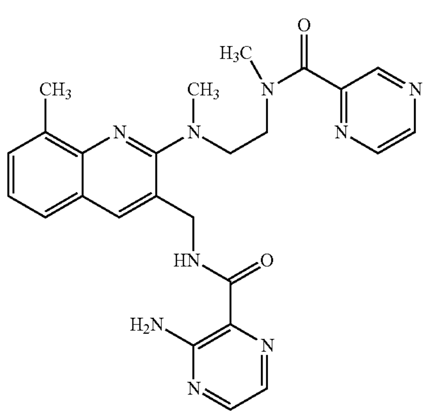 [SMILES: Cc1cccc2cc(CNC(=O)c3nccnc3N)c(N(C)CCN(C)C(=O)c3cnccn3)nc12] | 3-amino-N-{[8-methyl-2-(methyl (2-[methyl(pyrazin-2-ylcarbonyl)amino]ethyl}amino) quinolin-3-yl]methyl}pyrazine-2-carboxamide |

| Compound | Structure | Name |
|---|---|---|
| 79 | 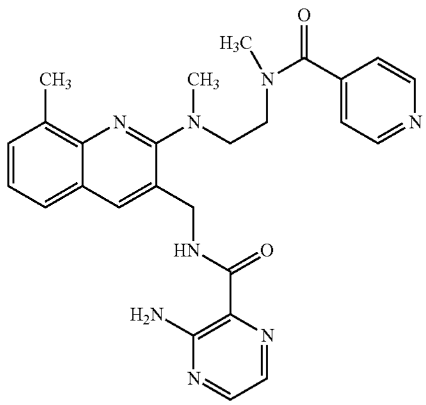 [SMILES: Cc1cccc2cc(CNC(=O)c3nccnc3N)c(N(C)CCN(C)C(=O)c3ccncc3)nc12] | 3-amino-N-{[8-methyl-2-(methyl{2-[methyl(pyridin-4-ylcarbonyl)amino]ethyl}amino)quinolin-3-yl]methyl}pyrazine-2-carboxamide |
| 80 | 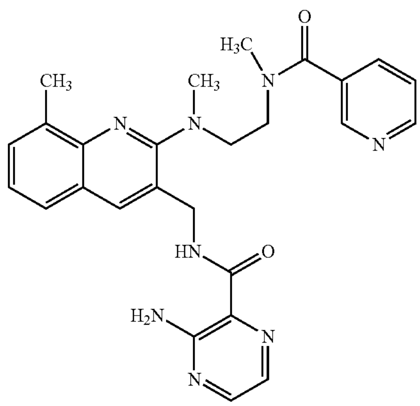 [SMILES: Cc1cccc2cc(CNC(=O)c3nccnc3N)c(N(C)CCN(C)C(=O)c3cccnc3)nc12] | 3-amino-N-+{[8-methyl-2-(methyl{2-[methyl(pyridin-3-ylcarbonyl)amino]ethyl}amino)quinolin-3-yl]methyl}pyrazine-2-carboxamide |
| 81 | 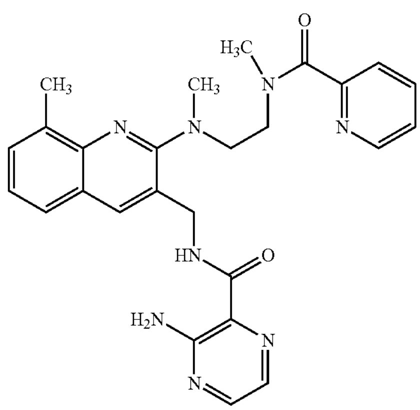 [SMILES: Cc1cccc2cc(CNC(=O)c3nccnc3N)c(N(C)CCN(C)C(=O)c3ccccn3)nc12] | 3-amino-N-{[8-methyl-2-(methyl{2-[methyl(pyridin-2-ylcarbonyl)amino]ethyl}amino)quinolin-3-yl]methyl}pyrazine-2-carboxamide |
| 82 | 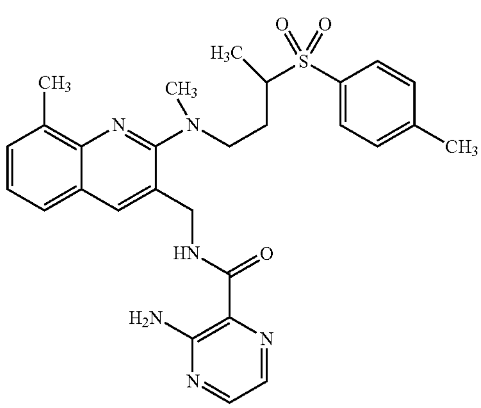 [SMILES: Cc1ccc(S(=O)(=O)C(C)CCN(C)c2nc3c(C)cccc3cc2CNC(=O)c2nccnc2N)cc1] | 3-amino-N-({8-methyl-2-[methyl(2-{methyl[(4-methylphenyl)sulfonyl]amino}ethyl)amino]quinolin-3-yl)methyl)pyrazine-2-carboxamide |

| Compound | Structure | Name |
|---|---|---|
| 83 | 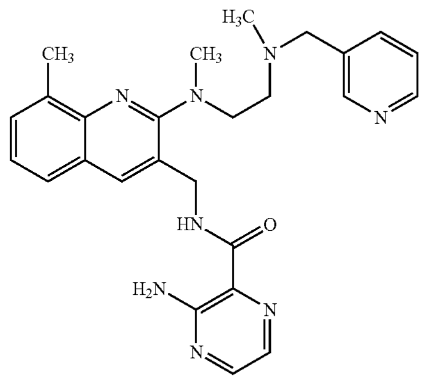 [SMILES: Cc1cccc2cc(CNC(=O)c3nccnc3N)c(N(C)CCN(C)Cc3cccnc3)nc12] | 3-amino-N-{[8-methyl-2-(methyl{2-[methyl(pyridin-3-ylmethyl)amino]ethyl}amino)quinolin-3-yl]methyl}pyrazine-2-carboxamide |
| 84 | 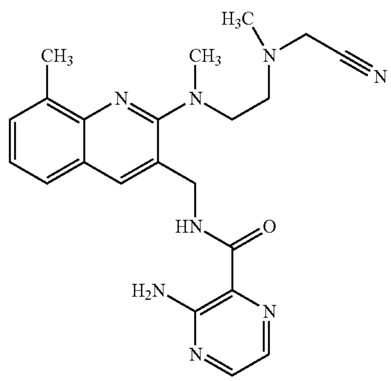 [SMILES: Cc1cccc2cc(CNC(=O)c3nccnc3N)c(N(C)CCN(C)CC#N)nc12] | 3-amino-N-({2-[{2-[(cyanomethyl)(methyl)amino]ethyl}(methyl)amino]-8-methylquinolin-3-yl}methyl)pyrazine-2-carboxamide |
| 85 | 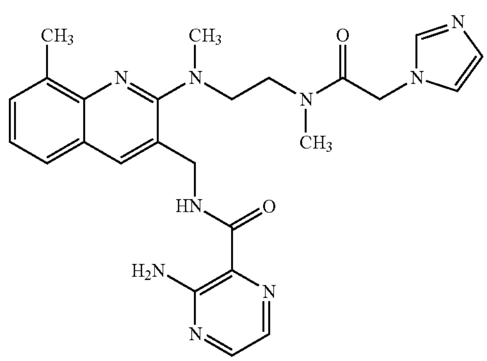 [SMILES: Cc1cccc2cc(CNC(=O)c3nccnc3N)c(N(C)CCN(C)C(=O)Cn3ccnc3)nc12] | 3-amino-N-({2-[{2-[(1H-imidazol-1-ylacetyl)(methyl)amino]ethyl}(methyl)amino]-8-methylquinolin-3-yl}methyl)pyrazine-2-carboxamide |
| 86 | 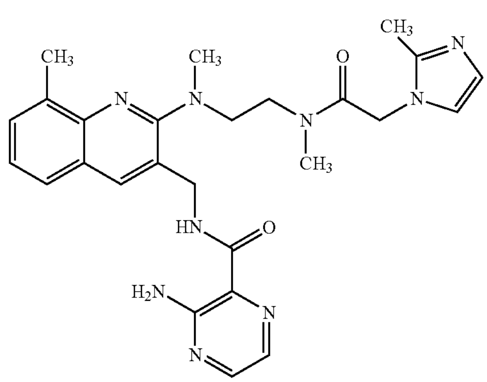 [SMILES: Cc1cccc2cc(CNC(=O)c3nccnc3N)c(N(C)CCN(C)C(=O)Cn3ccnc3C)nc12] | 3-amino-N-({8-methyl-2-[methyl(2-{methyl[(2-methyl-1H-imidazol-1-yl)acetyl]amino}ethyl)amino]quinolin-3-yl}methyl)pyrazine-2-carboxamide |

| Compound | Structure | Name |
|---|---|---|
| 87 | 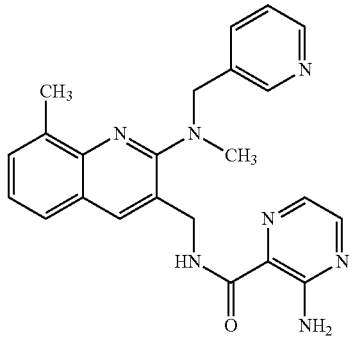 [SMILES: Cc1cccc2cc(CNC(=O)c3nccnc3N)c(N(C)Cc3cccnc3)nc12] | 3-amino-N-({8-methyl-2-[methyl(pyridin-3-ylmethyl)amino]quinolin-3-yl}methyl)pyrazine-2-carboxamide |
| 88 | 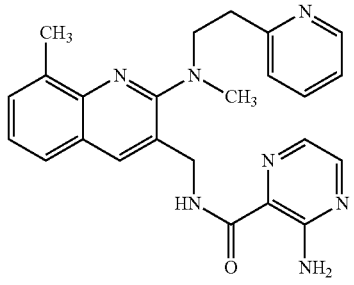 [SMILES: Cc1cccc2cc(CNC(=O)c3nccnc3N)c(N(C)CCc3ccccn3)nc12] | 3-amino-N-({8-methyl-2-[methyl(2-pyridin-2-ylethy)amino]quinolin-3-yl}methyl)pyrazine-2-carboxamide |
| 89 | 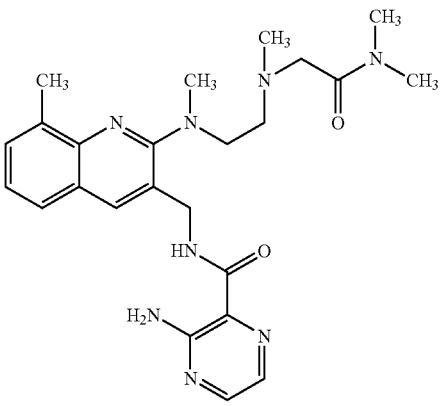 [SMILES: Cc1cccc2cc(CNC(=O)c3nccnc3N)c(N(C)CCN(C)CC(=O)N(C)C)nc12] | 3-amino-N-({2-[(2-{[2-(dimethylamino)-2-oxoethyl}(methyl)amino}ethyl)(methyl)amino]-8-methylquinolin-3-yl}methyl)pyrazine-2-carboxamide |
| 90 | 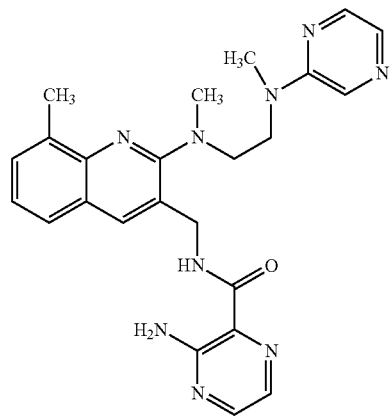 [SMILES: Cc1cccc2cc(CNC(=O)c3nccnc3N)c(N(C)CCN(C)c3cnccn3)nc12] | 3-amino-N-{[8-methyl-2-(methyl{2-[methyl(pyrazin-2-yl)amino]ethyl}amino)quinolin-3-yl]methyl}pyrazine-2-carboxamide |

-continued

| Compound | Structure | Name |
|---|---|---|
| 94 | 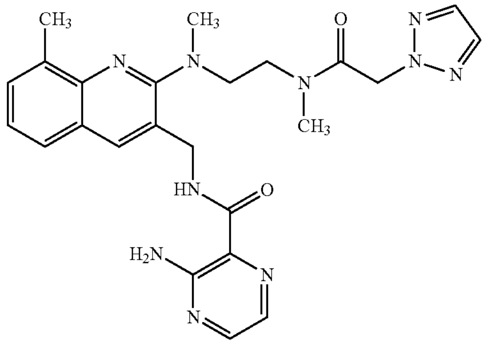 [SMILES: Cc1cccc2cc(CNC(=O)c3nccnc3N)c(N(C)CCN(C)C(=O)Cn3nccn3)nc12] | 3-amino-N-{[8-methyl-2-(methyl{2-[methyl(2H-1,2,3-triazol-2-ylacetyl)aminoethyl}amino)quinolin-3-yl]methyl}pyrazine-2-carboxamide |
| 95 | 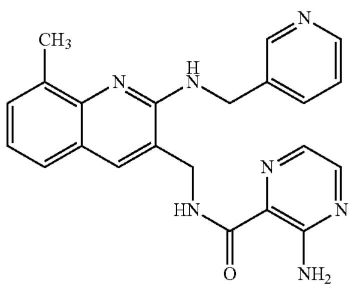 [SMILES: Cc1cccc2cc(CNC(=O)c3nccnc3N)c(NCc3cccnc3)nc12] | 3-amino-N-({8-methyl-2-[(pyridin-3-ylmethyl)amino]quinolin-3-yl}methyl)pyrazine-2-carboxamide |
| 96 | 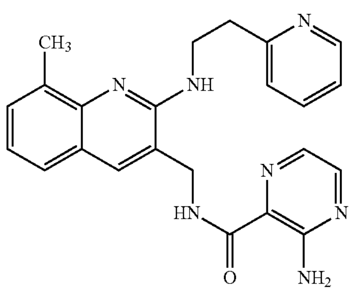 [SMILES: Cc1cccc2cc(CNC(=O)c3nccnc3N)c(NCCc3ccccn3)nc12] | 3-amino-N-({8-methyl-2-[(2-pyridin-2-ylethyl)amino]quinolin-3-yl}methyl)pyrazine-2-carboxamide |
| 97 | 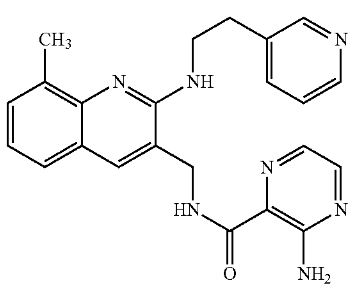 [SMILES: Cc1cccc2cc(CNC(=O)c3nccnc3N)c(NCCc3cccnc3)nc12] | 3-amino-N-({8-methyl-2-[(2-pyridin-3-ylethyl)amino]quinolin-3-yl}methyl)pyrazine-2-carboxamide |
| 98 | 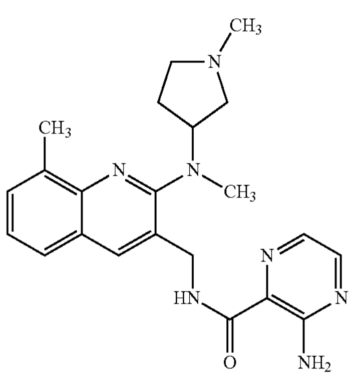 [SMILES: Cc1cccc2cc(CNC(=O)c3nccnc3N)c(N(C)C3CCN(C)C3)nc12] | 3-amino-N-({8-methyl-2-[methyl(1-methylpyrrolidin-3-yl)amino]quinolin-3-yl}methyl)pyrazine-2-carboxamide |

-continued

| Compound | Structure | Name |
|---|---|---|
| 99 | 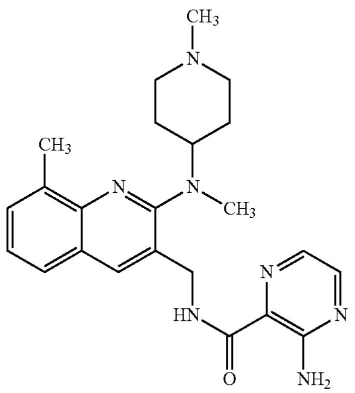 [SMILES: Cc1cccc2cc(CNC(=O)c3nccnc3N)c(N(C)C3CCN(C)CC3)nc12] | 3-amino-N-({8-methyl-2-[methyl(1-methylpiperidin-4-yl)amino]quinolin-3-yl}methyl)pyrazine-2-carboxamide |
| 100 | 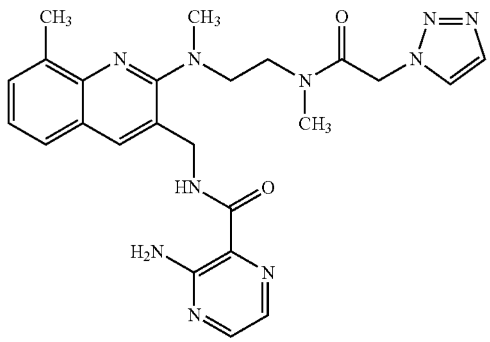 [SMILES: Cc1cccc2cc(CNC(=O)c3nccnc3N)c(N(C)CCN(C)C(=O)Cn3ccnn3)nc12] | 3-amino-N-{[8-methyl-2-(methyl{2-[methyl(1H-1,2,3-triazol-1-ylacetyl)amino]ethyl}amino)quinolin-3-yl]methyl}pyrazine-2-carboxamide |
| 101 | 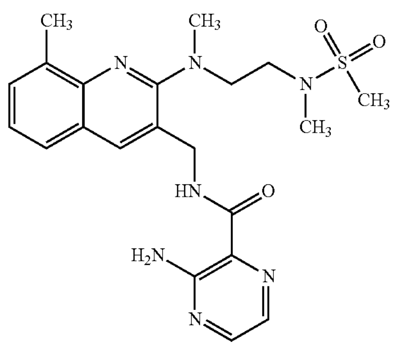 [SMILES: Cc1cccc2cc(CNC(=O)c3nccnc3N)c(N(C)CCN(C)S(C)(=O)=O)nc12] | 3-amino-N-{[8-methyl-2-(methyl{2-[methyl(methylsulfonyl)amino]ethyl}amino)quinolin-3-yl]methyl}pyrazine-2-carboxamide |
| 102 | 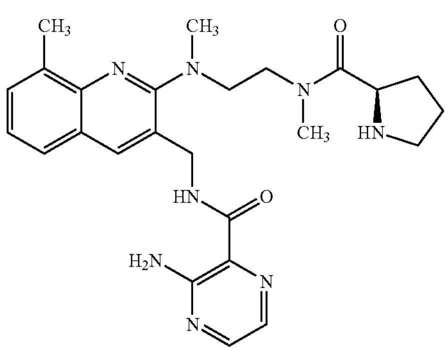 [SMILES: Cc1cccc2cc(CNC(=O)c3nccnc3N)c(N(C)CCN(C)C(=O)[C@H]3CCCN3)nc12] | 3-amino-N-{[8-methyl-2-(methyl{2-[methyl(D-prolyl)amino]ethyl}amino)quinolin-3-yl]methyl}pyrazine-2-carboxamide |

| Compound | Structure | Name |
|---|---|---|
| 103 | 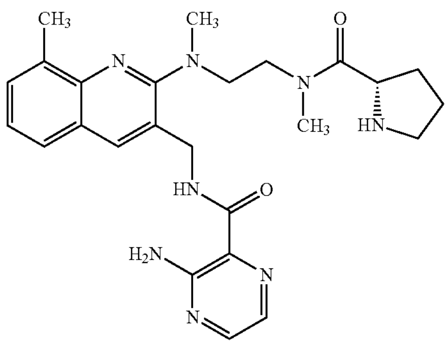 [SMILES: Cc1cccc2cc(CNC(=O)c3nccnc3N)c(N(C)CCN(C)C(=O)[C@@H]3CCCN3)nc12] | 3-amino-N-{[8-methyl-2-(methyl{2-[methyl(L-prolyl)amino]ethyl}amino)quinolin-3-yl]methyl}pyrazine-2-carboxamide |
| 104 | 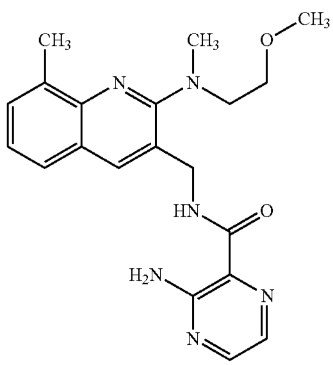 [SMILES: COCCN(C)c1nc2c(C)cccc2cc1CNC(=O)c1nccnc1N] | 3-amino-N-[(8-methyl-2-{methyl[2-(methyloxy)ethyl]amino}quinolin-3-yl)methyl]pyrazine-2-carboxamide |
| 109 | 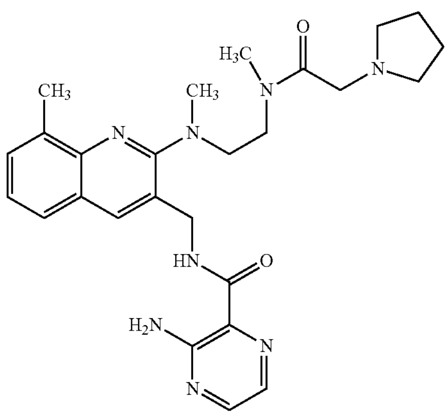 [SMILES: Cc1cccc2cc(CNC(=O)c3nccnc3N)c(N(C)CCN(C)C(=O)CN3CCCC3)nc12] | 3-amino-N-{[8-methyl-2-(methyl{2-[methyl(pyrrolidin-1-ylacetyl)amino]ethyl}amino)quinolin-3-yl]methyl}pyrazine-2-carboxamide |
| 110 | 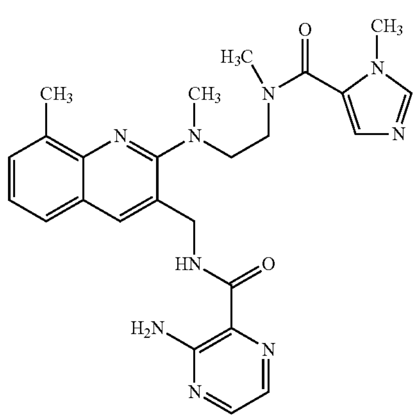 [SMILES: Cc1cccc2cc(CNC(=O)c3nccnc3N)c(N(C)CCN(C)C(=O)c3cncn3C)nc12] | 3-amino-N-({8-methyl-2-[methyl(2-{methyl[(1-methyl-1H-imidazol-5-yl)carbonyl]amino}ethyl)amino]quinolin-3-yl}methyl)pyrazine-2-carboxamide |

-continued

| Compound | Structure | Name |
| --- | --- | --- |
| 113 | 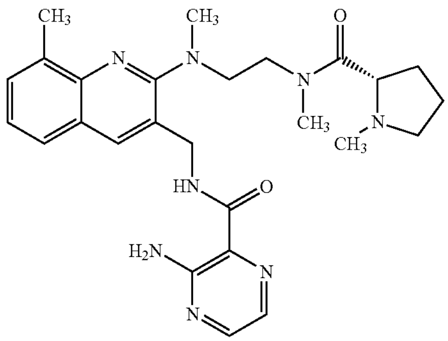 [SMILES: Cc1cccc2cc(CNC(=O)c3nccnc3N)c(N(C)CCN(C)C(=O)[C@@H]3CCCN3C)nc12] | 3-amino-N-{[8-methyl-2-(methyl{2-[methyl(1-methyl-L-prolyl)amino]ethyl}amino)quinolin-3-yl]methyl}pyrazine-2-carboxamide |
| 114 | 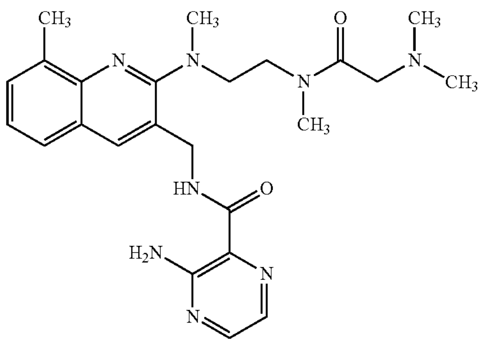 [SMILES: Cc1cccc2cc(CNC(=O)c3nccnc3N)c(N(C)CCN(C)C(=O)CN(C)C)nc12] | 3-amino-N-({2-[{2-[(N,N-dimethylglycyl)(methypamino]ethyl}(methypamino]-8-methylquinolin-3-yl}methyl)pyrazine-2-carboxamide |
| 115 | 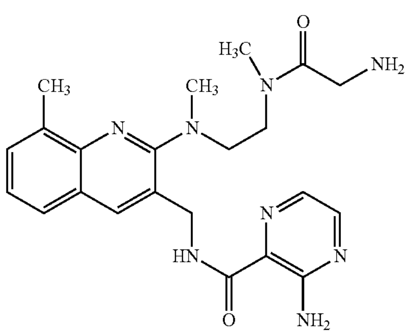 [SMILES: Cc1cccc2cc(CNC(=O)c3nccnc3N)c(N(C)CCN(C)C(=O)CN)nc12] | 3-amino-N-({2-[{2-[glycyl(methyl)amino]ethyl}(methyl)amino]-8-methylquinolin-3-yl}methyl)pyrazine-2-carboxamide |
| 116 | 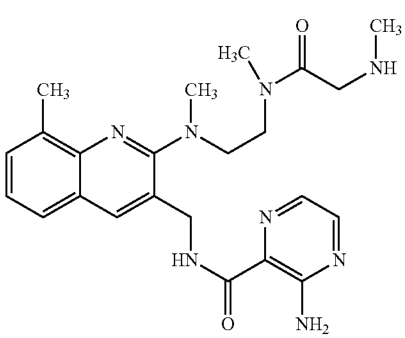 [SMILES: CNCC(=O)N(C)CCN(C)c1nc2c(C)cccc2cc1CNC(=O)c1nccnc1N] | 3-amino-N-{[8-methyl-2-(methyl{2-[methyl(N-methylglycyl)amino]ethyl}amino)quinolin-3-yl]methyl}pyrazine-2-carboxamide |

-continued

| Compound | Structure | Name |
|---|---|---|
| 121 | 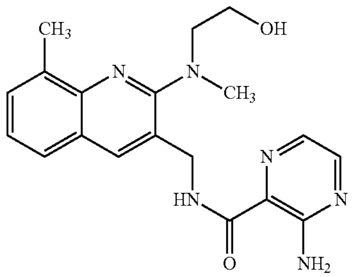 [SMILES: Cc1cccc2cc(CNC(=O)c3nccnc3N)c(N(C)CCO)nc12] | 3-amino-N-({2-[(2-hydroxyethyl)(methyl)amino]-8-methylquinolin-3-yl}methyl)pyrazine-2-carboxamide |
| 125 | 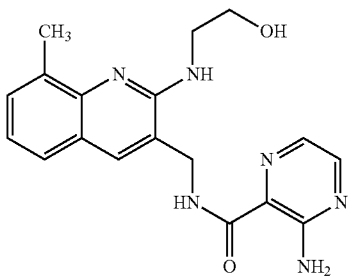 [SMILES: Cc1cccc2cc(CNC(=O)c3nccnc3N)c(NCCO)nc12] | 3-amino-N-({2-[(2-hydroxyethyl)amino]-8-methylquinolin-3-yl}methyl)pyrazine-2-carboxamide |
| 128 | 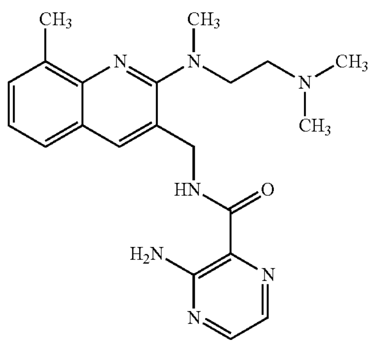 [SMILES: Cc1cccc2cc(CNC(=O)c3nccnc3N)c(N(C)CCN(C)C)nc12] | 3-amino-N-[(2-{[2-(dimethylamino)ethyl](methyl)amino}-8-methylquinolin-3-yl)methyl]pyrazine-2-carboxamide |
| 129 | 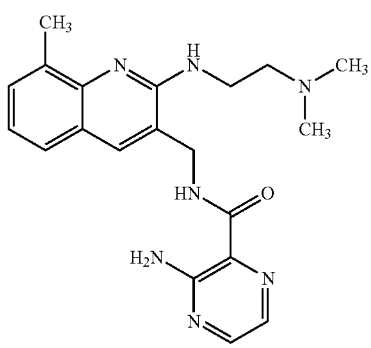 [SMILES: Cc1cccc2cc(CNC(=O)c3nccnc3N)c(NCCN(C)C)nc12] | 3-amino-N-[(2-{[2-(dimethylamino)ethyl]amino}-8-methylquinolin-3-yl)methyl]pyrazine-2-carboxamide |
| 130 | 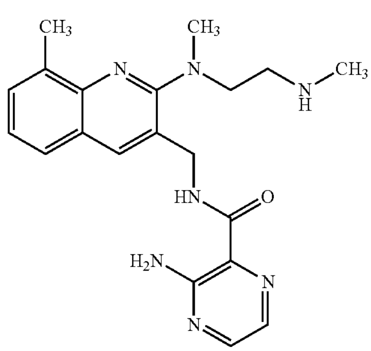 [SMILES: CNCCN(C)c1nc2c(C)cccc2cc1CNC(=O)c1nccnc1N] | 3-amino-N-[(8-methyl-2-{methyl[2-(methylamino)ethyl]amino}quinolin-3-yl)methyl]pyrazine-2-carboxamide |

-continued

| Compound | Structure | Name |
|---|---|---|
| 133 | 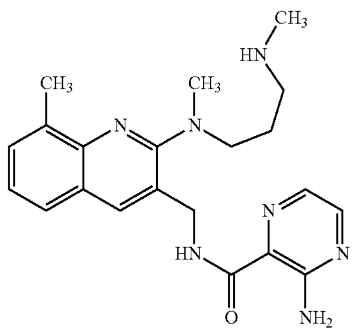 [SMILES: CNCCCN(C)c1nc2c(C)cccc2cc1CNC(=O)c1nccnc1N] | 3-amino-N-[(8-methyl-2-{methyl[3-(methylamino)propyl]amino}quinolin-3-yl)methyl]pyrazine-2-carboxamide |
| 136 | 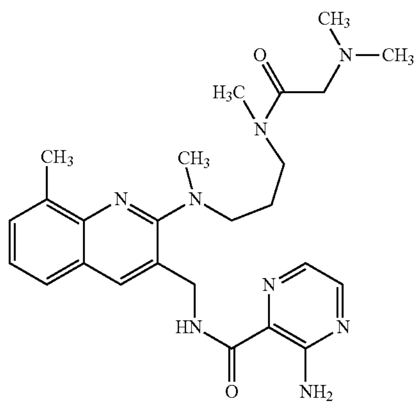 [SMILES: Cc1cccc2cc(CNC(=O)c3nccnc3N)c(N(C)CCCN(C)C(=O)CN(C)C)nc12] | 3-amino-N-({2-[{3-[(N,N-dimethylglycyl)(methyl)amino]propyl}(methyl)amino]-8-methylquinolin-3-yl}methyl)pyrazine-2-carboxamide |
| 138 | 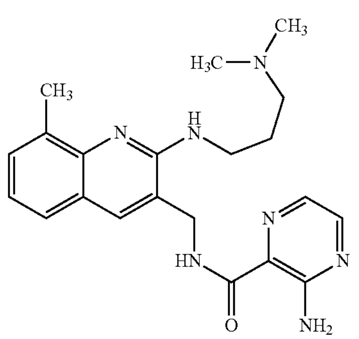 [SMILES: Cc1cccc2cc(CNC(=O)c3nccnc3N)c(NCCCN(C)C)nc12] | 3-amino-N-[(2-{[3-(dimethylamino)propyl]amino}-8-methylquinolin-3-yl)methyl]pyrazine-2-carboxamide |
| 149 | 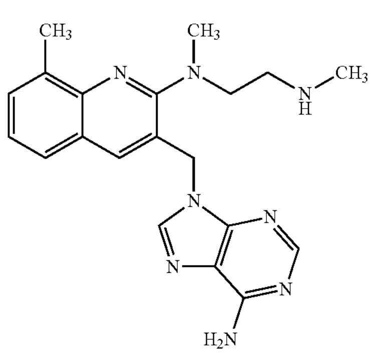 [SMILES: CNCCN(C)c1nc2c(C)cccc2cc1Cn1cnc2c(N)ncnc21] | N-{3-[(6-amino-9H-purin-9-yl)methyl]-8-methylquinolin-2-yl}-N,N'-dimethylethane-1,2-diamine |

-continued

| Compound | Structure | Name |
|---|---|---|
| 153 | 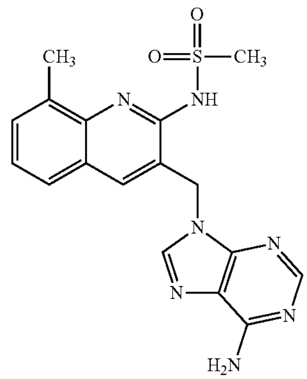 [SMILES: Cc1cccc2cc(Cn3cnc4c(N)ncnc43)c(NS(C)(=O)=O)nc12] | N-{3-[(6-amino-9H-purin-9-yl)methyl]-8-methylquinolin-2-yl}methanesulfonamide |
| 156 | 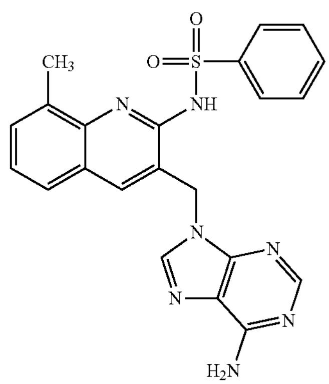 [SMILES: Cc1cccc2cc(Cn3cnc4c(N)ncnc43)c(NS(=O)(=O)c3ccccc3)nc12] | N-{3-[(6-amino-9H-purin-9-yl)methyl]-8-methylquinolin-2-yl}benzenesulfonamide |
| 164 | 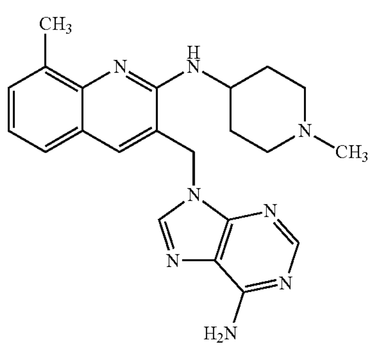 [SMILES: Cc1cccc2cc(Cn3cnc4c(N)ncnc43)c(NC3CCN(C)CC3)nc12] | 3-[(6-amino-9H-purin-9-yl)methyl]-8-methyl-N-(1-methylpiperidin-4-yl)quinolin-2-amine |
| 165 | 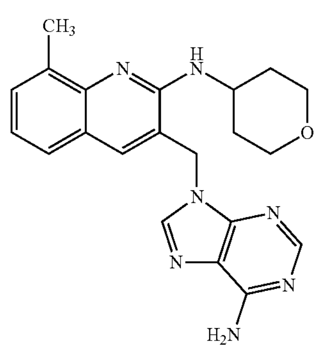 [SMILES: Cc1cccc2cc(Cn3cnc4c(N)ncnc43)c(NC3CCOCC3)nc12] | 3-[(6-amino-9H-purin-9-yl)methyl]-8-methyl-N-(tetrahydro-2H-pyran-4-yl)quinolin-2-amine |

-continued
| Compound | Structure | Name |
|---|---|---|
| 167 | 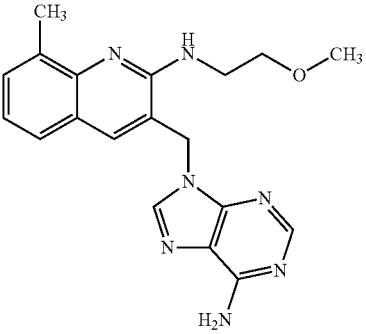 [SMILES: COCCNc1nc2c(C)cccc2cc1Cn1cnc2c(N)ncnc21] | 3-[(6-amino-9H-purin-9-yl)methyl]-8-methyl-N-[2-(methyloxy)ethyl]quinolin-2-amine. |
13. A method for treating inflammation, comprising administering to a mammal in need of such treatment a therapeutically effective amount of a compound of claim 1.
14. The method of claim 13, wherein the inflammation is mediated by PI3K delta.
* * * * *